US006225042B1

(12) United States Patent
Cai et al.

(10) Patent No.: US 6,225,042 B1
(45) Date of Patent: May 1, 2001

(54) ANTIGEN PRESENTING SYSTEM AND METHODS FOR ACTIVATION OF T-CELLS

(75) Inventors: Zeling Cai, San Diego; Jonathan Sprent, Leucadia; Anders Brunmark, San Diego; Michael Jackson, Del Mar; Per A. Peterson, Rancho Santa Fe, all of CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 09/039,982

(22) Filed: Mar. 16, 1998

Related U.S. Application Data

(62) Division of application No. 08/400,338, filed on Mar. 8, 1995, now abandoned.

(51) Int. Cl.[7] .............................. A01N 1/02; C12P 21/06; C12N 5/10; C12N 15/12
(52) U.S. Cl. .............................. 435/2; 435/69.1; 435/325; 435/348; 435/372.3; 435/395; 435/320.1
(58) Field of Search .............................. 435/2, 325, 348, 435/372.3, 395, 320.1, 69.1; 424/184.1, 93.71

(56) References Cited

U.S. PATENT DOCUMENTS 5,314,813 * 5/1994 Peterson et al. .
5,397,703 * 3/1995 De Boer et al. .
5,731,160 * 3/1998 Melief et al. .

FOREIGN PATENT DOCUMENTS

WO 9317095 * 9/1993 (WO).

OTHER PUBLICATIONS

Godeau et al. J. Biog Chem. 267: 24223, 1992.*
Malefyt et al. Eur. J. Immunol. 23: 418,1993.*
Fraser et al. Immunology Today 14: 357, 1993.*
Bellone et al. Eur. J. Immunology 24: 2691, 1994.*
Chen, C. et al. Immunology Today 13: 483–486, Oct. 1993.*
Chen C. et al. Cell 71: 1093–1102, Dec. 1992.*
Geppert, T. D. et al. Immunological Reviews 117: 5–66, 1990.*
Paul, W. E. (Ed.) Fundamental Immunology, 2nd Edition, Raven Press, New York, NY, pp. 363–365 and 434–435, 1989.*
Schwartz, R. H. Cell 71: 1065–1068, Dec. 1992.
*Baculovirus Expression Vectors: A Laboratory Manual* (O'Reilly, Miller and Luckow, Oxford U. Press, New York, 1994, p. 216.
Galleno and Sick, in *Gene Expression Systems: Using Nature for the Art of Expression*, ed. JM Fernandez and JP Hoeffler, Academic Press, San Diego, 1999, p. 352.

* cited by examiner

Primary Examiner—Christina Y. Chan
Assistant Examiner—F. Pierre VanderVegt
(74) Attorney, Agent, or Firm—Olson & Hierl, Ltd.

(57) ABSTRACT

The present invention relates to methods for activating T lymphocytes using a synthetic matrix, and for specifically activating T lymphocytes reactive to a specific peptide.

5 Claims, 9 Drawing Sheets

ANTIGEN PRESENTING SYSTEM AND METHODS FOR ACTIVATION OF T-CELLS

This application is a division of application Ser. No. 08/400,338, filed Mar. 8, 1995 (now abandoned).

This invention was made with the support of the Government of the United States of America, and the Government of the United States of America has certain rights in the invention.

TECHNICAL FIELD

The present invention relates to materials and methods of activating T-cells with specificity for particular antigenic peptides, the use of activated T-cells in vivo for the treatment of a variety of disease conditions, and compositions appropriate for these uses.

BACKGROUND

The efficiency with which the immune system cures or protects individuals from infectious disease has always been intriguing to scientists, as it has been believed that it might be possible to activate the immune system to combat other types of diseases. Such diseases include cancer, AIDS, hepatitis and infectious disease in immunosuppressed patients. While various procedures involving the use of antibodies have been applied in those types of diseases, few if any successful attempts using cytotoxic T-cells have been recorded. Theoretically, cytotoxic T-cells would be the preferable means of treating the types of disease noted above. However, no procedures have been available to specifically activate cytotoxic T-cells.

Cytotoxic T-cells, or CD8 cells as they are presently known, represent the main line of defense against viral infections. CD8 lymphocytes specifically recognize and kill cells which are infected by a virus. Thus, the cost of eliminating a viral infection is the accompanying loss of the infected cells. The T-cell receptors on the surface of CD8 cells cannot recognize foreign antigens directly. In contrast to antibodies, antigen must first be presented to the receptors.

The presentation of antigen to CD8 T-cells is accomplished by major histocompatibility complex (MHC) molecules of the Class I type. The major histocompatibility complex (MHC) refers to a large genetic locus encoding an extensive family of glycoproteins which play an important role in the immune response. The MHC genes, which are also referred to as the HLA (human leucocyte antigen) complex, are located on chromosome 6 in humans. The molecules encoded by MHC genes are present on cell surfaces and are largely responsible for recognition of tissue transplants as "non-self". Thus, membrane-bound MHC molecules are intimately involved in recognition of antigens by T-cells.

MHC products are grouped into three major classes, referred to as I, II, and III. T-cells that serve mainly as helper cells express CD4 and primarily interact with Class II molecules, whereas CD8-expressing cells, which mostly represent cytotoxic effector cells, interact with Class I molecules.

Class I molecules are membrane glycoproteins with the ability to bind peptides derived primarily from intracellular degradation of endogenous proteins. Complexes of MHC molecules with peptides derived from viral, bacterial and other foreign proteins comprise the ligand that triggers the antigen responsiveness of T-cells. In contrast, complexes of MHC molecules with peptides derived from normal cellular products play a role in "teaching" the T-cells to tolerate self-peptides, in the thymus. Class I molecules do not present entire, intact antigens; rather, they present peptide fragments thereof, "loaded" onto their "peptide binding groove".

For many years, immunologists have hoped to raise specific cytotoxic cells targeting viruses, retroviruses and cancer cells. While targeting against viral diseases in general may be accomplished in vivo by vaccination with live or attenuated vaccines, no similar success has been achieved with retroviruses or with cancer cells. Moreover, the vaccine approach has not had the desired efficacy in immunosuppressed patients. At least one researcher has taken the rather non-specific approach of "boosting" existing CD8 cells by incubating them in vitro with IL-2, a growth factor for T-cells. However, this protocol (known as LAK cell therapy) will only allow the expansion of those CD8 cells which are already activated. As the immune system is always active for one reason or another, most of the IL-2 stimulated cells will be irrelevant for the purpose of combatting the disease. In fact, it has not been documented that this type of therapy activates any cells with the desired specificity. Thus, the benefits of LAK cell therapy are controversial at best, and the side effects are typically so severe that many studies have been discontinued.

Several novel molecules which appear to be involved in the peptide loading process have recently been identified. It has also been noted that Class I molecules without bound peptide (i.e., "empty" molecules) can be produced under certain restrictive circumstances. These "empty" molecules are often unable to reach the cell surface, however, as Class I molecules without bound peptide are very thermolabile. Thus, the "empty" Class I molecules disassemble during their transport from the interior of the cell to the cell surface.

The presentation of Class I MHC molecules bound to peptide alone has generally ineffective in activating CD8 cells. In nature, the CD8 cells are activated by antigen-presenting cells which present not only a peptide-bound Class I MHC molecule, but also a costimulatory molecule. Such costimulatory molecules include B7 which is now recognized to be two subgroups designated as B7.1 and B7.2. It has also been found that cell adhesion molecules such as integrins assist in this process.

When the CD8 T-cell interacts with an antigen-presenting cell having the peptide bound by a Class I MHC and costimulatory molecule, the CD8 T-cell is activated to proliferate and becomes an armed effector T-cell. See, generally, Janeway and Travers, *Immunobiology*, published by Current Biology Limited, London (1994), incorporated by reference.

Accordingly, what is needed is a means to activate T-cells so that they proliferate and become cytotoxic. It would be useful if the activation could be done in vitro and the activated cytotoxic T-cells reintroduced into the patient. It would also be desirable if the activation could be done by a synthetic antigen-presenting matrix comprised of a material such as cells which not only presents the selected peptide, but also presents other costimulatory factors which increase the effectiveness of the activation.

It would also be advantageous if it was possible to select the peptide so that substantially only those CD8 cells cytotoxic to cells presenting that peptide would be activated.

BRIEF SUMMARY OF THE INVENTION

The present invention relates to a synthetic antigen-presenting system for presenting an MHC molecule complexed to a peptide and an assisting molecule to a T-cell to activate the T-cell.

In one embodiment, the system relates to a synthetic antigen-presenting matrix having a support and at least the extracellular portion of a Class I MHC molecule capable of binding to a selected peptide operably linked to the support. The matrix also includes at -east an extracellular portion of an assisting molecule operably linked to the support. The two extracellular portions are present in sufficient numbers to activate a population of T-cell lymphocytes against the peptide when the peptide is bound to the extracellular portion of the MHC molecule.

It has been found that an antigen-presenting matrix having both an MHC molecule or a portion of a MHC molecule together with an assisting molecule, or at least an extracellular portion of an assisting molecule, provides a synergistic reaction in activating T-cell lymphocytes against the peptide. Examples of assisting molecules are costimulatory molecules such as B7.1 and B7.2 or adhesion molecules such as ICAM-1 and LFA-3. It has been found that a specifically effective synergistic reaction results from an antigen-presenting matrix having MHC molecules bound with a peptide, a costimulatory molecule, and an adhesion molecule.

The support used for the matrix can take several different forms. Examples for the support include solid support such as metals or plastics, porous materials such as resin or modified cellulose columns, microbeads, microtiter plates, red blood cells and liposomes.

Another type of support is a cell fragment, such as a cell membrane fragment or an entire cell. In this embodiment, the matrix is actually cells which have been transfected to present MHC molecules and assisting molecules on the cell surface. This is done by producing a cell line containing at least one expressible Class I MHC nucleotide sequence for the MHC heavy chain, preferably a cDNA sequence, operably linked to a first promoter and an expressible β-2 microglobulin nucleotide sequence operably linked to a second promoter. The MHC heavy chain and the β-2 microglobulin associate together form the MHC molecule which binds to the peptide. The MHC protein binds with the antigenic peptide and presents it on the surface of the cell. The cell also includes a gene for a nucleotide sequence of an assisting molecule operably linked to a third promoter. The assisting molecule is also presented on the surface of the cell. These molecules are presented on the surface of the cell in sufficient numbers to activate a population of T-cell lymphocytes against the peptide when the peptide is bound to the complexes.

The cell line is synthetic in that at least one of the genes described above is not naturally present in the cells from which the cell line is derived. It is preferable to use a poikilotherm cell line because MHC molecules are thermolabile. A range of species are useful for this purpose. See, for example, U.S. Pat. No. 5,314,813 to Petersen et al. which discusses numerous species for this use and is incorporated by reference. It is preferred to use eukaryotic cells and insect cells in particular.

In one embodiment, it is particularly preferred to have at least two assisting molecules, one being a costimulatory molecule and the other being an adhesion molecule. It has been found that this combination has a synergistic effect, giving even greater T-cell activation than either of the individual molecules combined. It has also been found to be advantageous and preferable to have at least one of the transfected genes under control of an inducible promoter.

Using the present invention, it is possible to introduce the peptide to the cell while it is producing MHC molecules and allow the peptide to bind the MHC molecules while they are still within the cell. Alternatively, the MHC molecules can be expressed as empty molecules on the cell surface and the peptide introduced to the cells after the molecules are expressed on the cell surface. In this latter procedure, the use of poikilotherm cells is particularly advantageous because empty MHC molecules, those not yet complexed or bound with peptides, are thermolabile.

Class I MHC molecules have been expressed in insect cells such as *Drosophila melanogaster* (fruit fly) cells. Since Drosophila does not have all the components of a mammalian immune system, the various proteins involved in the peptide loading machinery should be absent from such cells. The lack of peptide loading machinery allows the Class I molecules to be expressed as empty molecules at the cell surface.

Another advantage of using insect cells such as the Drosophila system is that Drosophila cells prefer a temperature of 28° C. rather than 37° C. This fact is very important, because empty Class I molecules are thermolabile and tend to disintegrate at 37° C. By incubating the Class I-expressing Drosophila cells with peptides that can bind to the Class I molecule, it is possible to get virtually every Class I molecule to contain one and the same peptide. The cells are accordingly very different from mammalian cells, where the Class I molecules contain many different types of peptides, most of which are derived from our own, innocuous cellular proteins.

The present invention also relates to methods for producing activated CD8 cells in vitro. One method comprises contacting, in vitro, CDS cells with one of the antigen-presenting matrices described above for a time period sufficient to activate, in an antigen-specific manner, the CD8 cells. The method may further comprise (1) separating the activated CD8 cells from the antigen-presenting matrix; (2) suspending the activated CD8 cells in an acceptable carrier or excipient; and (3) administering the suspension to an individual in need of treatment. The antigens may comprise native or undegraded proteins or polypeptides, or they may comprise antigenic polypeptides which have been cleaved into peptide fragments comprising at least 8 amino acid residues prior to incubation with the human Class I MHC molecules.

In another variation, the invention relates to methods treating conditions in patients and specifically killing target cells in a human patient. The method comprises (1) obtaining a fluid sample containing resting or naive CD8 cells from the patient; (2) contacting, in vitro, the CD8 cells with an antigen-presenting matrix for a time period sufficient to activate, in an antigen-specific manner, the CD8 cells; and (3) administering the activated CD8 cells to the patient. The invention also relates to the method of treating a medical condition by administration of an antigen-presenting matrix in a suitable suspension. In various embodiments the condition may comprise cancer, tumors, neoplasia, viral or retroviral infection, autoimmune or autoimmune-type conditions. In one embodiment, the method of administering the matrix comprises intravenous injection.

BRIEF DESCRIPTION OF THE DRAWINGS

In FIG. 1, pRmHa-2 construction is shown; in FIG. 2, pRmHa-3 construction is shown; and in FIG. 3, the pRmHa-3 vector is illustrated, showing the restriction, polylinker, promoter, and polyadenylation sites, as well as a site at which a nucleotide sequence may be inserted for expression;

DETAILED DESCRIPTION OF THE INVENTION

Figure 1:
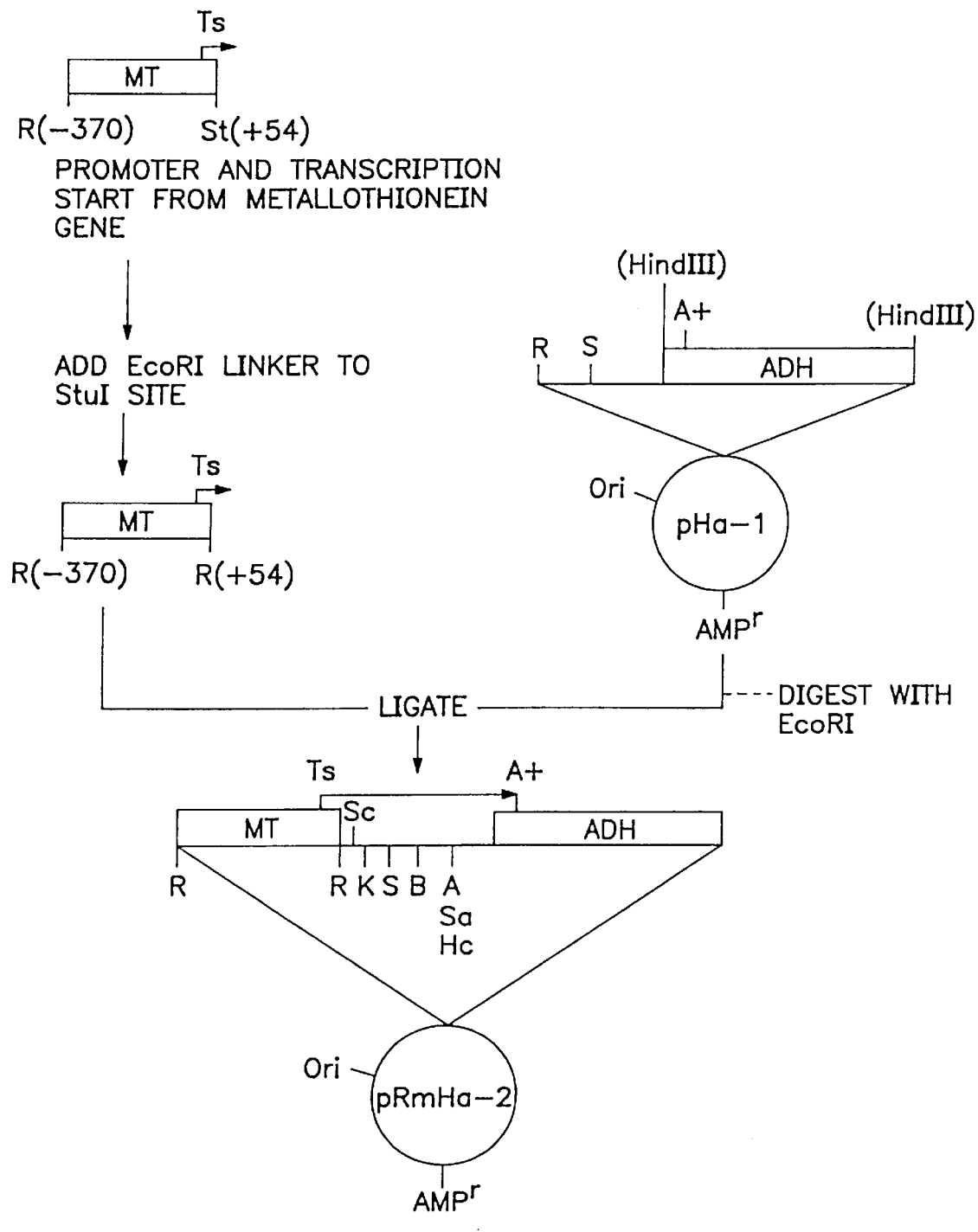
FIGS. 1–3 diagram the construction of expression plasmids pRmHa-2 and pRmHa-3.

The present invention relates to a synthetic antigen-presenting system which can be used to activate T-cell lymphocytes. The system activates cytotoxic CD8 cells which then proliferate and then are activated to seek out and destroy target cells. The present invention can be used to activate T-cells in vitro and the activated T-cells are then returned to the patient from which they were originally derived or may be used in vivo activation of T-cells.

The synthetic antigen-presenting system of the present invention has two major components. The first component is at least the extracellular portion of the Class I MHC molecule which is capable of binding to a selected peptide. The second major component is at least the extracellular portion of an assisting molecule which assists in the activation of T-cells. In each case, an extracellular portion is used, but it in certain embodiments, the entire molecules are used.

For ease of description, MHC molecules will be discussed generally, with the understanding that an extracellular portion of the MHC molecule may be used. The portion of the MHC molecule necessary for the present invention is the part which binds to the selected peptide and presents the peptide to the T-cell.

The peptide is selected to activate the appropriate T-cell, depending on the treatment to be conducted. For example, in the treatment of particular cancers, certain antigenic peptides are presented on the surface of the cancer cells which will react with activated T-cells. Thus, it is appropriate to use a peptide selected to activate the appropriate T-cells which will then bind with and destroy the cancer cells.

The present invention allows the MHC molecules to be produced by cells with the peptide already complexed with the MHC molecule or to produce empty MHC molecules which do not yet have a peptide complexed with them. This latter embodiment is particularly useful since it allows the peptide to be chosen after the MHC molecules are prepared.

A Class I MHC molecule includes a heavy chain, sometimes referred to as an alpha chain, and a $\beta$-2 microglobulin. As discussed herein, the extracellular portion of the Class I MHC molecule is made up of an extracellular portion of an MHC heavy chain together with the $\beta$-2 microglobulin.

In preparing the extracellular portions of MHC to be linked to a support, soluble molecules are prepared as discussed below. These molecules generally lack the transmembrane and cytoplasmic domain in the MHC molecule.

The assisting molecule helps facilitate the activation of the T-cell when it is presented with a peptide/MHC molecule complex. The present invention includes two major categories of assisting molecules. The first category is composed of costimulatory molecules such as B7.1 (previously known as B7 and also known as CD80) and B7.2 (also known as CD86) which binds to CD28 on T-cells.

The other major category of assisting molecules of the present invention are adhesion molecules. These include the various ICAM molecules, which include ICAM-1, ICAM-2, ICAM-3 and LFA-3. It has been found that the combination of a peptide bound to an MHC molecule used in conjunction with one of these assisting molecules activates the T-cells to an extent previously not seen.

An even greater synergistic reaction has been achieved by using a peptide-bound MHC molecule in conjunction with both a costimulatory molecule and an adhesion molecule.

In accordance with the present invention, the MHC molecule and the assisting molecule are operably linked to a support such that the MHC and assisting molecules are present in sufficient numbers to activate a population of T-cells lymphocytes against the peptide when the peptide is bound to the extracellular portion of the MHC molecule. The peptide can be bound to the MHC molecule before or after the MHC molecule is linked to the support.

The support can take on many different forms. It can be a solid support such as a plastic or metal material, it can be a porous material such as commonly used in separation columns, it can be a liposome or red blood cell, or it can even be a cell or cell fragment. As discussed in more detail below, in the case where a cell serves as a support, the MHC and assisting molecules can be produced by the cell. The MHC molecule is then linked to the cell by at least the transmembrane domain if not also the cytoplasmic domain which would not be present in a soluble form of MHC.

The extracellular portions of MHC molecule and assisting molecule can be linked to a support by providing an epitope which reacts to an antibody immobilized on the support. In addition, the MHC or assisting molecules can be produced with or linked to $(His)_6$ which would react with nickel in forming part of the support. Other means to immobilize or link MHC molecules to a support are well known in the art.

As discussed above, the support can be a cell membrane or an entire cell. In such a case, an eukaryotic cell line is modified to become a synthetic antigen-presenting cell line for use with T-cell lymphocytes. For ease of description, antigen-presenting cells will also be called stimulator cells. Because empty MHC molecules are thermolabile, it is preferred that the cell culture be poikilotherm and various cell lines are discussed in detail below.

A culture of cells is first established. The culture is then transfected with an expressible Class I MHC heavy chain gene which is operably linked to a promoter. The gene is chosen so that it is capable of expressing the Class I MHC heavy chain. The cell line is also transfected with an expressible β-2 microglobulin gene which is operably linked to a second promoter. The gene is chosen such it is capable of expressing β-2 microglobulin that forms MHC molecules with the MHC heavy chain. In the case of soluble extracellular portions of MHC molecules to be used with solid supports and the like, a truncated MHC heavy chain gene is used as discussed in more detail below.

The culture is also transfected with an expressible assisting molecule gene operably linked to a third promoter. The assisting molecule gene is capable of being expressed as an assisting molecule which interacts with the molecule on the T-cell lymphocytes. As discussed below, each of these genes can be transfected using various methods, but the preferred method is to use more than one plasmid.

The cell line transfected is chosen because it lacks at least one of the genes being introduced. It has been found that insect cells are advantageous not only because they are poikilothermic, but because they lack these genes and the mechanisms which would otherwise produce MHC molecules bound to peptides. This allows for greater control over the production of peptide-bound MHC molecules, and the production of empty MHC molecules. The MHC heavy chain is preferably from a different species, more preferably, a homeotherm such as mammals and, optimally, humans.

The preferred cell line is a stable poikilotherm cell line that has the first promoter being inducible to control the expression of the MHC heavy chain. It is preferred that the cell assembles empty MHC molecules and presents them on the cell surface so that the peptides can be chosen as desired.

The resulting MHC molecules bind to the peptide and are present in sufficient numbers with the assisting molecules on the surface of the cell to activate a population of T-cell lymphocytes against the peptide when the peptide is bound to the MHC cells.

In a further embodiment, a second assisting molecule gene is also transfected into the cell culture. In this case, the first assisting molecule gene can be for a costimulatory molecule and the second assisting molecule gene can be for an adhesion molecule.

It is preferred that at least one of the genes and, in particular, the MHC heavy chain gene be linked to an inducible promoter. This allows control over the production of MHC molecules so that they are only produced at a time when the peptide of interest is available and presented in the culture to react with the produced MHC molecules. This minimizes undesirable MHC molecule/peptide complexes.

Where the cell line already produces one or more of the desired molecules, it is only necessary to transfect the culture with an expressible gene for the gene which is lacking in the cells. For example, if the cells already present the MHC molecules on their surface, it is only necessary to transfect the culture with an expressible gene for the assisting molecule.

The peptide can be introduced into the cell culture at the time the cells are producing MHC molecules. Through methods such as osmotic shock, the peptides can be introduced in the cell and bind to the produced MHC molecules. Alternatively, particularly in the case poikilotherm cell lines, the MHC molecules will be presented empty on the cell surface. The peptide can then be added to the culture and bound to the MHC molecules as desired.

After the cells are produced having MHC and assisting molecules on their surfaces, they can be lyophilized and the fragments of the cells used to activate the population of T-cell lymphocytes.

Transfected cultures of cells can be used to produced extracellular portions of MHC molecules and assisting molecules. The use of extracellular portions in conjunction with supports such as solid supports has certain advantages of production. Where living cells are used to provide a synthetic antigen-presenting cell, at least three genes, two to produce the MHC molecule and one for the assisting molecule must be introduced to the cell. Often, additional genes such as for antibiotic resistance are also transfected.

Where a solid support system is being used, one cell line can produce the extracellular portions of MHC molecules while another cell line produces the extracellular portion of the assisting molecule. The MHC molecule portions and the assisting molecule portions can then be harvested from their respective cultures. The molecules are then linked to an appropriate support in sufficient numbers to activate a population of T-cell lymphocytes against a peptide when the peptide is bound to the extracellular portion of the MHC molecule. From a production standpoint, two different cultures can be used, but it is also possible to use the same culture, however, requiring that the culture be transfected with the additional gene for the extracellular portion of the assisting molecule.

A further modification of this embodiment is to provide a third culture of cells which is transfected with an expressible second assisting molecule gene. In this example, the second culture of cells produces extracellular portions of the costimulatory molecule while the third culture of cells produce an extracellular portion of an adhesion molecule. The adhesion molecule is portions are harvested and linked to the support.

The present invention also relates to a method for activating CD8 T-cells against a selected peptide. The method relates to providing a cell line presenting MHC molecules binding a peptide and assisting molecules on their surfaces. Naive CD8 T-cells can be obtained by removal from a patient to be treated. The cultured cells are then contacted with the CD8 T-cells for a sufficient period of time to activate the CD8 T-cell lymphocytes resulting in proliferation and transforming the T-cells into armed effector cells.

The activated CD8 T-cells can then be separated from the cell line and put into a suspension in an acceptable carrier and administered to the patient. An alternative method involves the use of the synthetic antigen-presenting matrix to activate the CD8 cells.

It is preferred that human genes are used and, therefore, human molecule analogs are produced. As shown in prior U.S. Pat. No. 5,314,813, murine systems provide particularly useful models for testing the operation of T-cell activation and demonstrate the applicability of the process for human systems. See also Sykulev et al., *Immunity* 1: 15–22 (1994).

1. Human Class I MHC Molecules

Class I MHC molecules comprise a heavy chain and a β-microglobulin protein. A human Class I MHC heavy chain of the present invention is selected from the group comprising HLA-A, HLA-B, HLA-C, HLA-E, HLA-F, and HLA-G, and more preferably, from the group comprising HLA-A, HLA-B, and HLA-C. The heavy chains are useful in either soluble or insoluble form. In the soluble ("sol") form, a stop codon is engineered into the nucleotide sequence encoding the HLA molecule of choice preceding the transmembrane domain.

While it is possible to isolate nucleotide sequences encoding human Class I MHC heavy chains from known, established cell lines carrying the appropriate variants—e.g., transformed cell lines JY, BM92, WIN, MOC, and MG—it is more practical to synthesize the nucleotide sequence from a portion of the gene via polymerase chain reaction (PCR), using the appropriate primers. This method has been successfully used to clone full-length HLA cDNA; for example, the sequences for HLA-A25, HLA-A2, HLA-B7, HLA-B57, HLA-B51, and HLA-B37 are deposited in the GenBank database under accession nos. M32321, M32322, M32317, M32318, M32319 and M32320, respectively. Known, partial and putative HLA amino acid and nucleotide sequences, including the consensus sequence, are published (see, e.g., Zemmour and Parham, *Immunogenetics* 33: 310–320 (1991)), and cell lines expressing HLA variants are known and generally available as well, many from the American Type Culture Collection ("ATCC"). Therefore, using PCR, it is possible to synthesize human Class I MHC-encoding nucleotide sequences which may then be operatively linked to a vector and used to transform an appropriate cell and expressed therein.

Particularly preferred methods for producing the Class I MHC heavy chain, β-2 microglobulin proteins and assisting molecules of the present invention rely on the use of preselected oligonucleotides as primers in a polymerase chain reaction (PCR) to form PCR reaction products as described herein. Gene preparation is typically accomplished by primer extension, preferably by primer extension in a polymerase chain reaction (PCR) format.

If the genes are to be produced by (PCR) amplification, two primers, i.e., a PCR primer pair, must be used for each coding strand of nucleic acid to be amplified. (For the sake of simplicity, synthesis of an exemplary HLA heavy chain variant sequence will be discussed, but it is expressly to be understood that the PCR amplification method described is equally applicable to the synthesis of β-2 microglobulin, costimulatory molecules, adhesion molecules, and all HLA variants, including those whose complete sequences are presently unknown.)

The first primer becomes part of the antisense (minus or complementary) strand and hybridizes to a nucleotide sequence conserved among HLA (plus or coding) strands. To produce coding DNA homologs, first primers are therefore chosen to hybridize to (i.e. be complementary to) conserved regions within the MHC genes, preferably, the consensus sequence or similar, conserved regions within each HLA group—i.e., consensus sequences within HLA-A, HLA-B, HLA-C, and the less-polymorphic groups, HLA-E, -F, and -G.

Second primers become part of the coding (plus) strand and hybridize to a nucleotide sequence conserved among minus strands. To produce the HLA-coding DNA homologs, second primers are therefore chosen to hybridize with a conserved nucleotide sequence at the 5' end of the HLA-coding gene such as in that area coding for the leader or first framework region. In the amplification of the coding DNA homologs the conserved 5' nucleotide sequence of the second primer can be complementary to a sequence exogenously added using terminal deoxynucleotidyl transferase as described by Loh et al., *Science* 243: 217–220 (1989). One or both of the first and second primers can contain a nucleotide sequence defining an endonuclease recognition site. The site can be heterologous to the immunoglobulin gene being amplified and typically appears at or near the 5' end of the primer.

The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acid Res.* 17: 711–722 (1989). Amplification systems based on transcription have been described by Gingeras et al., in *PCR Protocols. A Guide to Methods and Applications*, pp 245–252, Academic Press, Inc., San Diego, Calif. (1990).

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). Various preferred methods and primers used herein are described hereinafter and are also described in Nilsson, et al., *Cell* 58: 707 (1989), Ennis, et al., *PNAS USA* 87: 2833–7 (1990), and Zemmour, et al., *Immunogenetics* 33: 310–20 (1991), for example. In particular, it is preferred to design primers from comparison of 5' and 3' untranslated regions of HLA alleles (e.g., -A, -B, -C, -E, -F, or -G alleles), with selection of conserved sequences. Restriction sites may also be incorporated into the 5' and 3' primers to enable the amplification products to be subcloned into sequencing or expression vectors. It may also be helpful to place a 4-base spacer sequence proximal to the restriction site to improve the efficiency of cutting amplification products with enzymes.

The following primers are preferred for amplification of HLA-A, -B, -C, -E, -F, and -G cDNA, preferably in separate reactions. Resulting cDNAs may then be cloned and sequenced as described herein. These primers are appropriate for use in amplifying all known and presently unknown types of HLA.

HLA A

```
5' primer:  5' CC ACC ATG GCC GTC ATG GCG CCC 3'    (SEQ ID NO 1)

3' primer:  5' GG TCA CAC TTT ACA AGC TCT GAG 3'    (SEQ ID NO 2)
```

-continued

HLA B

5' primer:  5' CC ACC ATG CTG GTC ATG GCG CCC 3'    (SEQ ID NO 3)

3' primer:  5' GG ACT CGA TGT GAG AGA CAC ATC 3'    (SEQ ID NO 4)

HLA C

5' primer:  5' CC ACC ATG CGG GTC ATG GCG CCC 3'    (SEQ ID NO 5)

3' primer:  5' GG TCA GGC TTT ACA AGC GAT GAG 3'    (SEQ ID NO 6)

HLA E

5' primer:  5' CC ACC ATG CGG GTA GAT GCC CTC C 3'    (SEQ ID NO 7)

3' primer:  5' GG TTA CAA GCT GTG AGA CTC AGA 3'    (SEQ ID NO 8)

HLA F

5' primer:  5' CC ACC ATG GCG CCC CGA AGC CTC 3'    (SEQ ID NO 9)

3' primer:  5' GG TCA CAC TTT ATT AGC TGT GAG A 3'    (SEQ ID NO 10)

HLA G

5' primer:  5' CC ACC ATG GCG CCC CGA ACC CTC 3'    (SEQ ID NO 11)

3' primer:  5' GG TCA CAA TTT ACA AGC CGA GAG 3'    (SEQ ID NO 12)

In preferred embodiments only one pair of first and second primers is used per amplification reaction. The amplification reaction products obtained from a plurality of different amplifications, each using a plurality of different primer pairs, are then combined. However, the present invention also relates to DNA homolog production via co-amplification (using two pairs of primers), and multiplex amplification (using up to about 8, 9 or 10 primer pairs).

In preferred embodiments, the PCR process is used not only to produce a variety of human Class I-encoding DNA molecules, but also to induce mutations which may emulate those observed in the highly-polymorphic HLA loci, or to create diversity from a single parental clone and thereby provide a Class I MHC molecule-encoding DNA "library" having a greater heterogeneity. In addition to the mutation inducing variations described in the above referenced U.S. Pat. No. 4,683,195 and such as discussed in U.S. Pat. No. 5,314,813.

2. DNA Expression Vectors

A vector of the present invention is a nucleic acid (preferably DNA) molecule capable of autonomous replication in a cell and to which a DNA segment, e.g., gene or polynucleotide, can be operatively linked so as to bring about replication of the attached segment. One of the nucleotide segments to be operatively linked to vector sequences encodes at least a portion of a mammalian Class I MHC heavy chain. Preferably, the entire peptide-coding sequence of the MHC heavy chain is inserted into the vector and expressed; however, it is also feasible to construct a vector which also includes some non-coding MHC sequences as well. Preferably, non-coding sequences of MHC are excluded. Alternatively, a nucleotide sequence for a soluble ("sol") form of an Class I MHC heavy chain may be utilized; the "sol" form differs from the non-sol form in that it contains a "stop" codon inserted at the end of the alpha 3 domain or prior to the transmembrane domain. Another preferred vector includes a nucleotide sequence encoding at least a portion of a mammalian β-2 microglobulin molecule operatively linked to the vector for expression. Still another preferred vector includes a nucleotide sequence encoding at least a portion of a mammalian assisting molecule operably linked to the vector for expression. It is also feasible to construct a vector including nucleotide sequences encoding a Class I MHC heavy chain and a β-2 microglobulin and an assisting molecule, or some combination of these.

A preferred vector comprises a cassette that includes one or more translatable DNA sequences operatively linked for expression via a sequence of nucleotides adapted for directional ligation. The cassette preferably includes DNA expression control sequences for expressing the polypeptide or protein that is produced when a translatable DNA sequence is directionally inserted into the cassette via the sequence of nucleotides adapted for directional ligation. The cassette also preferably includes a promoter sequence upstream from the translatable DNA sequence, and a polyadenylation sequence downstream from the mammalian MHC heavy chain sequence. The cassette may also include a selection marker, albeit it is preferred that such a marker be encoded in a nucleotide sequence operatively linked to another expression vector sequence.

The choice of vector to which a cassette of this invention is operatively linked depends directly, as is well known in the art, on the functional properties desired, e.g., vector replication and protein expression, and the host cell to be transformed, these being limitations inherent in the art of constructing recombinant DNA molecules.

In various embodiments, a vector is utilized for the production of polypeptides useful in the present invention, including MHC variants and antigenic peptides. Exemplary vectors include the plasmids pUC8, pUC9, pUC18, pBR322, and pBR329 available from BioRad Laboratories (Richmond, Calif.), pPL and pKK223 available from Pharmacia (Piscataway, N.J.), and pBS and M13mp19 (Stratagene, La Jolla, Calif.). Other exemplary vectors include pCMU (Nilsson, et al., *Cell* 58: 707 (1989)). Other appropriate vectors may also be synthesized, according to known methods; for example, vectors pCMU/$K^b$ and PCMUII used in various applications herein are modifications of pCMUIV (Nilsson, et al., supra).

In addition, there is preferably a sequence upstream of the translatable nucleotide sequence encoding a promoter sequence. Preferably, the promoter is conditional (e.g., inducible). A preferred conditional promoter used herein is a metallothionein promoter or a heat shock promoter.

Vectors may be constructed utilizing any of the well-known vector construction techniques. Those techniques, however, are modified to the extent that the translatable nucleotide sequence to be inserted into the genome of the host cell is flanked "upstream" of the sequence by an appropriate promoter and, in some variations of the present invention, the translatable nucleotide sequence is flanked "downstream" by a polyadenylation site. This is particularly preferred when the "host" cell is an insect cell and the nucleotide sequence is transmitted via transfection. Transfection may be accomplished via numerous methods, including the calcium phosphate method, the DEAE-dextran method, the stable transfer method, electroporation, or via the liposome mediation method. Numerous texts are available which set forth known transfection methods and other procedures for introducing nucleotides into cells; see, e.g., *Current Protocols in Molecular Biolocy*, John Wiley & Sons, N.Y. (1991).

The vector itself may be of any suitable type, such as a viral vector (RNA or DNA), naked straight-chain or circular DNA, or a vesicle or envelope containing the nucleic acid material and any polypeptides that are to be inserted into the cell. With respect to vesicles, techniques for construction of lipid vesicles, such as liposomes, are well known. Such liposomes may be targeted to particular cells using other conventional techniques, such as providing an antibody or other specific binding molecule on the exterior of the liposome. See, e.g., A. Huang, et al., *J. Biol. Chem.* 255: 8015–8018 (1980). See, e.g., Kaufman, *Meth. Enzymol.* 185: 487–511 (1990).

In a preferred embodiment, the vector also contains a selectable marker. After expression, the product of the translatable nucleotide sequence may then be purified using antibodies against that sequence. One example of a selectable marker is neomycin resistance. A plasmid encoding neomycin resistance, such as phshsneo, phsneo, or pcopneo, may be included in each transfection such that a population of cells that express the gene(s) of choice may be ascertained by growing the transfectants in selection medium.

Figure 3:
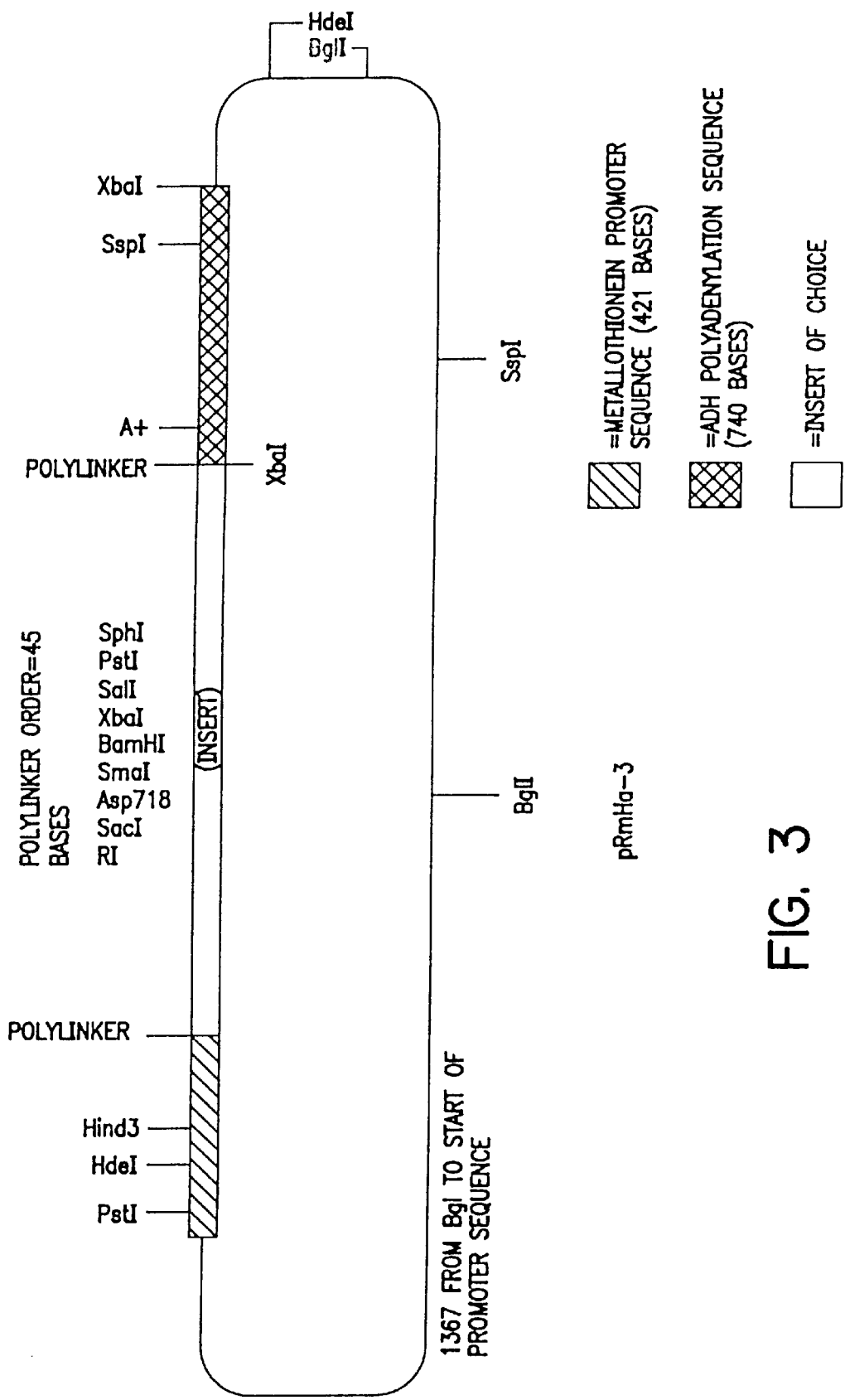

A preferred vector for use according to the present invention is a plasmid; more preferably, it is a high-copy-number plasmid. It is also desirable that the vector contain an inducible promoter sequence, as inducible promoters tend to limit selection pressure against cells into which such vectors (which are often constructed to carry non-native or chimeric nucleotide sequences) have been introduced. It is also preferable that the vector of choice be best suited for expression in the chosen host. If the host cell population is a Drosophila cell culture, then a compatible vector includes vectors functionally equivalent to those such as p25-lacZ (see Bello and Couble, *Nature* 346: 480 (1990)) or pRmHa-1, -2, or -3 (see Bunch, et al., *Nucl. Acids Res.* 16: 1043–1061 (1988)). In the preferred embodiment, the vector is pRmHa-3, which is shown in FIG. 3. This vector includes a metallothionein promoter, which is preferably upstream of the site at which the MHC sequence is inserted, and the polyadenylation site is preferably downstream of said MHC sequence. Insect cells and, in particular, Drosophila cells are preferred hosts according to the present invention. Drosophila cells such as Schneider 2 (S2) cells have the necessary trans-acting factors required for the activation of the promoter and are thus even more preferred.

Figure 2:
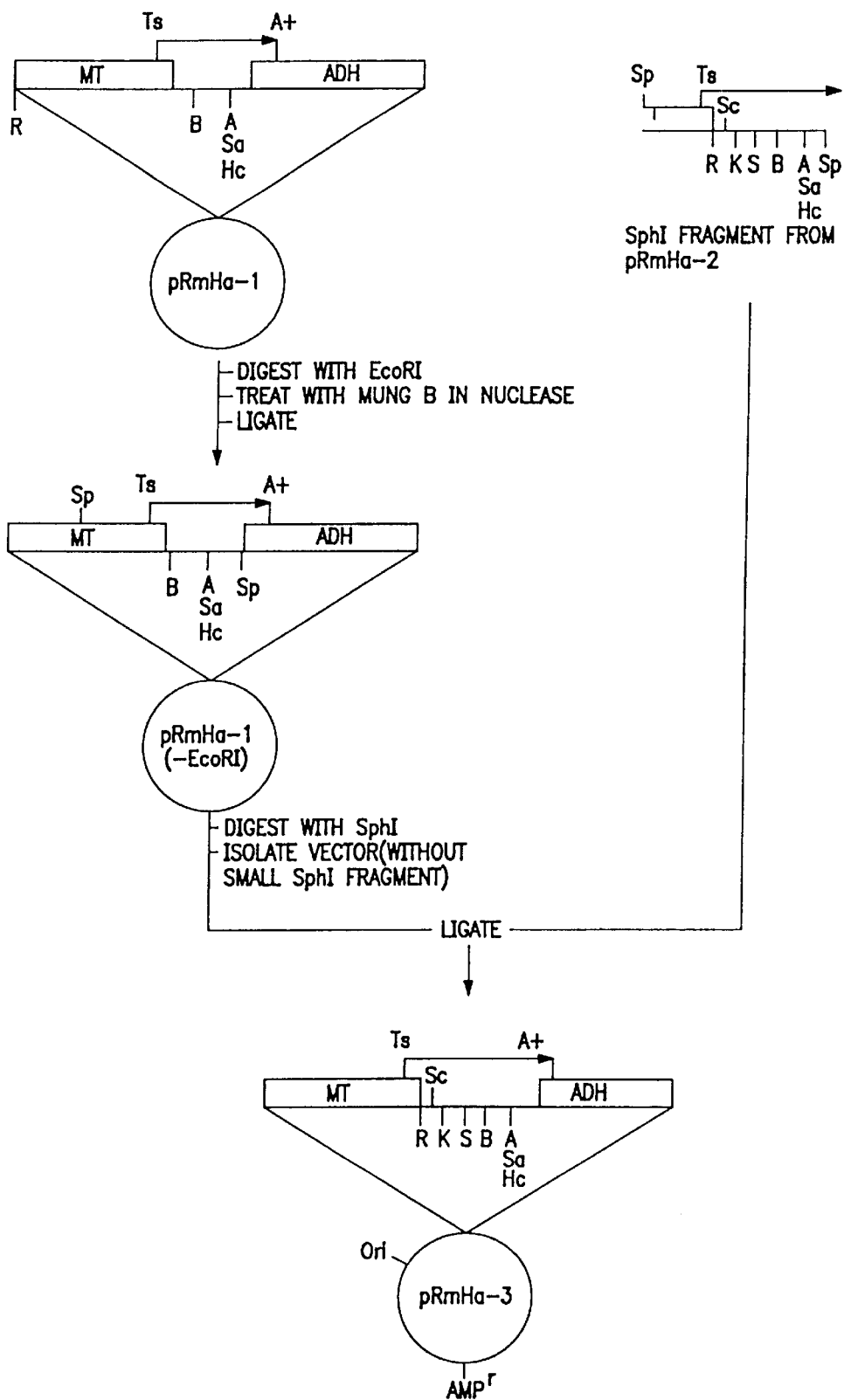

The expression vector pRmHa-3 is based on the bacterial plasmid pRmHa-1 (FIG. 2), the latter of which is based on plasmid pUC18 and is deposited with the American Type Culture Collection (ATCC, Rockville, Md.), having the accession number 37253. The pRmHa-3 vector contains the promoter, the 5' untranslated leader sequence of the metallothionein gene (sequences 1–421, SEQ ID NO 13) with the R1 and Stu sites removed; see FIG. 3). It also contains the 3' portion of the Drosophila ADH gene (sequence #6435–7270, SEQ ID NO 14) including the polyadenylation site. Therefore, cloned DNA will be transcriptionally regulated by the metallothionein promoter and polyadenylated. Construction of the pRmHa-1 plasmid is described in Bunch, et al., *Nucl. Acids Res.* 16: 1043–1061 (1988). Construction of the pRmHa-3 and pRmHa-2 plasmids (the latter of which has a metallothionein promoter sequence that may be removed as an Eco RI fragment) is illustrated in FIGS. 1, 2, and 3. With regard to pRmHa-3, a preferred plasmid for use according to the present invention, Pst I, Sph I and Hind III are in the promoter fragment and therefore are not unique. Xba is in the ADH fragment (4 bases from its 3' end) and is also not unique. The following restriction sites are, however, unique in pRma-3: Eco RI, Sac I, Kpn I, Sma I, Bam HI, Sal I, Hinc 2, and Acc I.

A cassette in a DNA expression vector of this invention is the region of the vector that forms, upon insertion of a translatable DNA sequence, a sequence of nucleotides capable of expressing, in an appropriate host, a fusion protein of this invention. The expression-competent sequence of nucleotides is referred to as a cistron. Thus, the cassette preferably comprises DNA expression control elements operatively linked to one or more translatable DNA sequences. A cistron is formed when a translatable DNA sequence is directionally inserted (directionally ligated) between the control elements via the sequence of nucleotides adapted for that purpose. The resulting translatable DNA sequence, namely the inserted sequence, is, preferably, operatively linked in the appropriate reading frame.

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

Thus, a DNA expression vector of this invention provides a system for cloning translatable DNA sequences into the cassette portion of the vector to produce a cistron capable of expressing a fusion protein of this invention.

3. Cell Lines

A preferred cell line of the present invention is capable of continuous growth in culture and capable of expressing mammalian Class I MHC molecules and assisting molecules on the surface of its cells. Any of a variety of transformed and non-transformed cells or cell lines are appropriate for this purpose, including bacterial, yeast, insect, and mammalian cell lines. (See, e.g., *Current Protocols in Molecular Biology*, John Wiley & Sons, N.Y. (1991), for summaries and procedures for culturing and using a variety of cell lines, e.g., *E. coli* and *S. cerevisiae*.)

Preferably, the cell line is a eukaryotic cell line. More preferably, the cell line is poikilothermic (i.e., less sensitive to temperature challenge than mammalian cell lines). More preferably, it is an insect cell line. Various insect cell lines are available for use according to the present invention, including moth (ATCC CCL 80), armyworm (ATCC CRL 1711), mosquito larvae (ATCC lines CCL 125, CCL 126, CRL 1660, CRL 1591, CRL 6585, CRL 6586) and silkworm (ATCC CRL 8851). In a preferred embodiment, the cell line is a Drosophila cell line such as a Schneider cell line (see Schneider, *J. Embryol. Exp. Morph.* 27: 353–365 (1972)); preferably, the cell line is a Schneider 2 (S2) cell line (S2/M3) adapted for growth in M3 medium (see Lindquist, et al., *Drosochila Information Service* 58: 163 (1982)).

Schneider cells may be prepared substantially as follows. *Drosophila melanogaster* (Oregon-R) eggs are collected over about a 4 hour interval and are dechlorinated in 2.5% aqueous sodium hypochlorite and surface-sterilized by immersion in 70% ethanol for 20 minutes, followed by an additional 20 minutes in 0.05% $HgCl_2$ in 70% ethanol. After being rinsed thoroughly in sterile distilled water, the eggs are transferred to petri dishes containing sterile Metricel black filters backed with Millipore prefilters, both previously wetted with culture medium. The eggs are placed overnight in a 22° C. incubator and removed for culturing when 20–24 hours old. The embryos are each cut into halves or thirds, then placed in 0.2% trypsin (1:250, Difco) in Rinaldini's salt solution (Rinaldini, *Nature* (London) 173: 1134–1135 (1954)) for 20–45 minutes at room temperature. From 100–300 embryos are used to initiate each culture.

After the addition of fetal bovine serum (FBS), the fragments are centrifuged at 100×g for 2–3 minutes, resuspended in 1.25 ml culture medium and seeded into glass T-9 flasks. The cultures are maintained at about 22–27° C.±0.5° C., with a gaseous phase of ambient air. Schneider's culture medium (Schneider, *J. Exp. Zool.* 156: 91–104 (1964); Schneider, *J. Embryol. Exp. Morph.* 15: 271–279 (1966)) containing an additional 500 mg bacteriological peptone per 100 ml medium and supplemented with 15% inactivated FBS is preferably used. The pH (preferably 6.7–6.8) is monitored with 0.01% phenol red. The cell lines are preferably maintained by subculturing every 3–7 days. The cells readily attach to the glass but not so firmly as to require trypsin treatment; typically, simple pipetting is adequate to flush most of the cells from the bottom of the flasks. The morphological appearance of the cells is described in Schneider, *J. Embryol. Exp. Morph.* 27: 353–365 (1972). They are essentially epithelial-like in appearance and range from about 5–11 μm in diameter and 11–35 μm in length. Small pockets containing rounded cells may be dispersed randomly throughout the other cells.

Preferably, the Schneider 2 (S2) cells are maintained in Schneider's Drosophila medium plus 10% FBS including penicillin (100 unit/ml) and streptomycin (100 mg/ml). It is preferable to keep the cells at a density of more than $0.5\times10^5$/ml, and to grow them at a 24–30° C. temperature range. The cells tend to double in fewer than 24 hours and grow to high cell density, i.e., about $2\times10^7$/ml or greater. The cells may also be frozen in 90% FBS and 10% DMSO, for later use or analysis. One may place the cells at −70° C. and then store in liquid nitrogen.

A preferred cell line according to the present invention, identified as Schneider 2 (S2) cells, has been deposited pursuant to Budapest Treaty requirements with the American Type Culture Collection (ATCC), Rockville, Md., on Feb. 18, 1992, and was assigned accession number CRL 10974.

Cells of the present invention are transfected with cDNAs encoding (human) MHC heavy chains, β-2 microglobulin and one or more assisting molecules, which have each been inserted into (i.e., operatively linked to) an expression vector. In a more preferred embodiment, the vector comprises Drosophila expression plasmid pRmHa-3, into which expressible nucleotide sequences encoding human Class I MHC heavy chains, human β-2 microglobulin or human assisting molecules have been inserted using techniques disclosed herein. Preferably, the cDNAs encoding MHC heavy chains, those encoding β-2 microglobulin and those encoding assisting molecules are operatively linked to separate expression plasmids and are cotransfected into the cultured cells. Alternatively, the cDNAs encoding MHC heavy chains, β-2 microglobulin and assisting molecules may be operatively linked to the same expression plasmid and cotransfected via that same plasmid. In another variation, cDNAs encoding MHC heavy chains, β-2 microglobulin, assisting molecules, and a cytokine such as IL-2 are operatively linked to expression plasmids and are cotransfected into a cell line of the present invention. Selection of HLA genes, construction of appropriate vectors and primer selection are described in greater detail above.

Successfully transformed cells, i.e., cells that contain an expressible human nucleotide sequence according to the present invention, can be identified via well-known techniques. For example, cells resulting from the introduction of a cDNA or rDNA of the present invention can be cloned to produce monoclonal colonies. Cells from those colonies can be harvested, lysed, and their DNA content examined for the presence of the rDNA using a method such as that described by Southern, *J. Mol. Biol.* 98: 503 (1975). In addition to directly assaying for the presence of rDNA, successful transformation or transfection may be confirmed by well-known immunological methods when the rDNA is capable of directing the expression of a subject chimeric polypeptide. For example, cells successfully transformed with an expression vector may produce proteins displaying particular antigenic properties which are easily determined using the appropriate antibodies. In addition, successful transformation/transfection may be ascertained via the use of an additional vector bearing a marker sequence, such as neomycin resistance, as described hereinabove.

It is also preferable that the culture be stabile and capable of sustained growth at reduced temperatures. For example, it is preferred that the culture be maintained at about room temperature, e.g., about 24–27° C. In other embodiments, the culture is maintained at higher temperatures, particularly during the process of activating CD8 cells. It is thus preferred that a culture according to the present invention be capable of withstanding a temperature challenge of about 30° C. to about 37° C. Addition of β-2 microglobulin to a culture stabilizes the Class I MHC to at least a 30° C. challenge; addition of β-2 microglobulin and peptides results in greater thermostability at higher temperatures, i.e., at 37° C.

In order to prepare the culture for expression of empty—or more preferably, peptide-loaded—MHC molecules, the culture may first require stimulation, e.g., via $CuSO_4$ induction, for a predetermined period of time. After a suitable induction period—e.g., about 12–48 hours, peptides may be added at a predetermined concentration (e.g., about 100 μg/ml). Peptides may be prepared as discussed below. After a further incubation period—e.g., for about 12 hours at 27° C.—the culture is ready for use in the activation of CD8 cells. While this additional incubation period may be shortened or perhaps omitted, the culture tends to become increasingly stable to temperature challenge if it is allowed to incubate for a time prior to addition of resting or naive CD8 cells. For example, cultures according to the present invention to which peptide has been added are capable of expressing significant amounts of peptide-loaded Class I MHC molecules even when incubated for extended periods of time at 37° C.

Nutrient media useful in the culturing of transformed host cells are well known in the art and can be obtained from numerous commercial sources. In embodiments wherein the host cell is mammalian, a "serum-free" medium is preferably used.

4. Human B-2 microglobulin and Assisting Molecules

In order to establish a cell line capable of producing therapeutically useful amounts of surface-expressed human Class I MHC molecules, it is preferable to cotransfect a cell line of the present invention with a vector operably linked to a nucleotide sequence encoding β-2 microglobulin in order to effect appropriate levels of expression of human MHC molecules in the cell line. While the nucleotide sequence encoding mammalian β-2 microglobulin such as mouse β-2 microglobulin increases the stability of the human Class I MHC molecules expressed in the cell lines of the present invention, it is preferable to cotransfect the cell line with a vector operably linked to an expressible nucleotide sequence encoding a human β-2 microglobulin.

As discussed above, a preferred vector according to the present invention includes a nucleotide sequence encoding at least a portion of a mammalian β-2 microglobulin molecule operatively linked to the vector for expression. The gene for the assisting molecules can be linked to the same or another vector. It is also feasible to construct a vector including nucleotide sequences encoding both a Class I MHC heavy chain and a β-2 microglobulin.

The sequencing and primers used for the assisting molecules are discussed in more detail below. However, the protocols are similar.

A human β-2 microglobulin cDNA sequence has been published (see Suggs, et al., *PNAS* 78: 6613–17, 1981) and the sequence was used as a template for a polymerase chain reaction (PCR) using the following primers:
5' primer:
5' GCTTGGATCCAGATCTACCAT-GTCTCGCTCCGTGGCCTTAGCTGTGCT CGCGC-TACTCTC 3' (SEQ ID NO 15)
3' primer
5' GGATCCGGATGGTTACATGTCGCGATC-CCACTTAAC 3' (SEQ ID NO 16)

The primers are used in a standard PCR reaction (see above and references cited therein). The reaction products are extracted with phenol, purified using a Geneclean kit (Bio 101, San Diego, Calif.), digested with Bam HI and cloned into the Bam HI site of pBS (Stratagene, La Jolla, Calif.). After verification of the sequence, this Bam HI fragment is cloned into the Bam HI site of an appropriate expression vector. In the preferred embodiment, human β-2 microglobulin cDNA is synthesized and operably linked to expression vector pRmHa-3.

5. Peptides

Virtually all cellular proteins in addition to viral antigens are capable of being used to generate relevant peptide fragments that serve as potential Class I MHC ligand. In most mammalian cells, then, any particular MHC peptide complex would represent only a small proportion of the total MHC encoded molecules found on the cell surface. Therefore, in order to produce surface-expressed human Class I MHC molecules that have an increased capacity to specifically activate CD8 cells, it is preferable to isolate and load peptide fragments of appropriate size and antigenic characteristics onto Class I molecules.

The peptides of the present invention bind to Class I MHC molecules. The binding occurs under biological conditions which can be created in vivo as well as in vitro. The exact nature of the binding of the peptides need not be known for practice of the invention.

In a preferred embodiment, the peptides to be loaded onto the Class I MHC molecules are antigenic. It is also preferred that the peptides be of a uniform size, preferably 8-mers or 9-mers, and most preferably, 8-mers. It is also preferable that the peptides prepared for loading onto the MHC molecules be of a single species; i.e., that all peptides loaded onto the MHC be identical in size and sequence. In this manner, it is possible to produce monoantigenic peptide-loaded MHC molecules.

Peptides may be presented to the cells via various means. Preferably, peptides are presented in a manner which allows them to enter an intracellular pool of peptides. For example, peptides may be presented via osmotic loading. Typically, peptides are added to the culture medium. The peptides may be added to the culture in the form of an intact polypeptide or protein which is subsequently degraded via cellular processes, e.g., via enzymatic degradation. Alternatively, the intact polypeptide or protein may be degraded via some other means such as chemical digestion (e.g. cyanogen bromide) or proteases (e.g. chymotrypsin) prior to its addition to the cell culture. In other embodiments, the peptides are presented in smaller segments which may or may not comprise epitopic amino acid sequences.

In a preferred embodiment, a sufficient amount of protein (s) or peptide(s) is added to the cell culture to allow the Class I MHC molecules to bind and subsequently present a large density of the peptide—preferably, with the same kind of peptide attached to each MHC—on the surface of human Class I MHC-expressing cells of the present invention. It is also preferred to allow the human Class I MHC heavy chains and human β-2 microglobulin to bind—i.e., to form heterodimers—prior to presenting peptide to the MHC molecules intracellularly.

In another embodiment of the invention, peptides are added to transfected cells of the present invention in order to enhance the thermostability of the MHC molecules expressed by the cells. As noted above, peptides are preferably added to the culture medium. Antigenic peptides that bind to the Class I molecules serve to thermostabilize the MHC molecules and also increase the cell surface expression. Cultures with added peptides which bind to the MHC molecules are thus significantly less susceptible to temperature challenge than cultures without added peptide.

In one embodiment of the present invention, antigenic peptides are presented to the transformed/transfected cell line in various forms. For example, an entire protein or other antigenic polypeptide may be degraded chemically or enzymatically, for example, and added to the cell line in this form. For example, a protein of interest is degraded with chymotrypsin and the resultant mixture of peptide "fragments" is added to a transformed or transfected cell culture; these cells are then allowed to "choose" the appropriate peptides (which are often smaller peptides, preferably 8 mers or 9 mers) to load onto the Class I MHC molecules. Alternatively, an entire protein or polypeptide sequence may be cloned into an appropriate vector and inserted into a procaryotic cell, whereby the cell generates significant amounts of the antigenic polypeptide which are then harvested, purified, and digested into peptides which are then added to the transformed/transfected eukaryotic cell culture. The cells again would be allowed to "choose" the peptides to load onto the expressed MHC.

6. Isolation of RestinQ or Precursor CD8 cells

Resting (or naive or precursor) CD8 cells—i.e., T-cells that have not been activated to target a specific antigen—are preferably extracted from the patient prior to incubation of the CD8 cells with the transformed cultures of the present invention. It is also preferred that precursor CD8 cells be harvested from a patient prior to the initiation of other treatment or therapy which may interfere with the CD8 cells' ability to be specifically activated. For example, if one is intending to treat an individual with a neoplasia or tumor, it is preferable to obtain a sample of cells and culture same prior to the initiation of chemotherapy or radiation treatment.

Methods of extracting and culturing lymphocytes are well known. For example, U.S. Pat. No. 4,690,915 to Rosenberg describes a method of obtaining large numbers of lymphocytes via lymphocytopheresis. Appropriate culturing conditions used are for mammalian cells, which are typically carried out at 37° C.

Various methods are also available for separating out and/or enriching cultures of precursor CD8 cells. Some examples of general methods for cell separation include indirect binding of cells to specifically-coated surfaces. In another example, human peripheral blood lymphocytes (PBL), which include CD8 cells, are isolated by Ficoll-Hypaque gradient centrifugation (Pharmacia, Piscataway, N.J.). PBL lymphoblasts may be used immediately thereafter or may be stored in liquid nitrogen after freezing in FBS containing 10% DMSO (Sigma Chemical Co., St. Louis, Mo.), which conserves cell viability and lymphocyte functions.

Alternative methods of separating out and/or enriching cultures of precursor cells include both positive and negative selection procedures. For positive selection, after lymphocyte-enriched PBL populations are prepared from whole blood, sub-populations of CD8 lymphocytes are isolated therefrom by affinity-based separation techniques directed at the presence of the CD8 receptor antigen. These affinity-based techniques include flow microfluorimetry, including fluorescence-activated cell sorting (FACS), cell adhesion, and like methods. (See, e.g., Scher and Mage, in *Fundamental Immunology*, W. E. Paul, ed., pp. 767–780, River Press, N.Y. (1984).) Affinity methods may utilize anti-CD8 receptor antibodies as the source of affinity reagent. Alternatively, the natural ligand, or ligand analogs, of CD8 receptor may be used as the affinity reagent. Various anti-T-cell and anti-CD8 monoclonal antibodies for use in these methods are generally available from a variety of commercial sources, including the American Type Culture Collection (Rockville, Md.) and Pharmingen (San Diego, Calif.).

Negative selection procedures are utilized to effect the removal of non-CD8 from the CD8 population. This technique results in the enrichment of CD8 cells from the T- and B-cell population of leucophoresed patients. Depending upon the antigen designation, different antibodies may be appropriate. (For a discussion and review of nomenclature, antigen designation, and assigned antibodies for human leucocytes, including T-cells, see Knapp, et al., *Immunolocy Today* 10: 253–258 (1989) and Janeway et al., *Immunobiology*, supra.) For example, monoclonal antibodies OKT4 (anti-CD4, ATCC No. CRL 8002) OKT 5 (ATCC Nos. CRL 8013 and 8016), OKT 8 (anti-CD8, ATCC No. CRL 8014), and OKT 9 (ATCC No. CRL 8021) are identified in the ATCC Catalogue of Cell Lines and Hybridomas (ATCC, Rockville, Md.) as being reactive with human T lymphocytes, human T-cell subsets, and activated T-cells, respectively. Various other antibodies are available for identifying and isolating T-cell species.

In a further embodiment, CD8 cells can be isolated by combining both negative and positive selection procedures. (See, e.g. Cai and Sprent, *J. Exp. Med.* 179: 2005–2015 (1994)).

Preferably, the PBLs are then purified. For example, Ficoll gradients may be utilized for this purpose. The purified PBLs would then be mixed with syngeneic Drosophila cells preincubated with the appropriate antigenic peptides.

7. In Vitro Activation of CD8 Cells

In order to optimize the in vitro conditions for the generation of specific cytotoxic T-cells, the culture of antigen-presenting cells is maintained in an appropriate medium. In the preferred embodiment, the antigen-presenting cells are Drosophila cells, which are preferably maintained in serum-free medium (e.g. Excell 400).

Prior to incubation of the antigen-presenting cells with the cells to be activated, e.g., precursor CD8 cells, an amount of antigenic peptide is added to the antigen-presenting cell culture, of sufficient quantity to become loaded onto the human Class I molecules to be expressed on the surface of the antigen-presenting cells. According to the present invention, a sufficient amount of peptide is an amount that will allow about 200 to about 500,000 and preferably about 200 to 1,000 or more, human Class I MHC molecules loaded with peptide to be expressed on the surface of each antigen-presenting cell. Preferably, the antigen-presenting cells are incubated with >20 µg/ml peptide.

Resting or precursor CD8 cells are then incubated in culture with the appropriate antigen-presenting cells for a time period sufficient to activate and further enrich for a population of CD8 cells. Preferably, the CD8 cells shall thus be activated in an antigen-specific manner. The ratio of resting or precursor CD8 (effector) cells to antigen-presenting cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:antigen-presenting cell (e.g. Drosophila cell) ratio is preferably in the range of about 30:1 to 300:1. For example, in one embodiment, $3 \times 10^7$ human PBL and $1 \times 10^5$ live Drosophila cells were admixed and maintained in 20 ml of RPMI 1640 culture medium.

The effector/antigen-presenting culture may be maintained for as long a time as is necessary to activate and enrich for a population of a therapeutically useable or effective number of CD8 cells. In general terms, the optimum time is between about one and five days, with a plateau"—i.e. a "maximum" specific CD8 activation level—generally being observed after five days of culture. In one embodiment of the present invention, in vitro activation of CD8 cells is detected within a brief period of time after transfection of a cell line. In one embodiment, transient expression in a transfected cell line capable of activating CD8 cells is detectable within 48 hours of transfection. This clearly indicates that either stable or transient cultures of transformed cells expressing human Class I MHC molecules are effective in activating CD8 cells.

Preferably, the enrichment and concordant activation of CD8 cells is optimal within one week of exposure to antigen-presenting cells. Thereafter, in a preferred embodiment, the enriched and activated CD8 cells are further purified by isolation procedures including site restriction, resetting with antibody-red blood cell preparations, column chromatography and the like. Following the purification, the resulting CD8 cell preparation is further expanded by maintenance in culture for a period of time to obtain a population of $10^9$ activated CD8 cells. This period may vary depending on the replication time of the cells but may generally be 14 days. Activation and expansion of CD8 cells has been described by Riddell et al., *Curr. Opin. Immunol.*, 5: 484–491 (1993).

8. Separation of CD8 Cells from Drosophila Cells

Activated CD8 cells may be effectively separated from the stimulator (e.g., Drosophila) cells using one of a variety of known methods. For example, monoclonal antibodies specific for the stimulator cells, for the peptides loaded onto the stimulator cells, or for the CD8 cells (or a segment thereof) may be utilized to bind their appropriate complementary ligand. Antibody-tagged cells may then be extracted from the stimulator-effector cell admixture via appropriate means, e.g., via well-known immunoprecipitation or immunoassay methods.

9. Administration of Activated CD8 Cells

Effective, cytotoxic amounts of the activated CD8 cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8 cells are utilized for adult humans, compared to about $5\times10^6$–$5\times10^7$ cells used in mice.

Preferably, as discussed above, the activated CD8 cells are harvested from the Drosophila cell culture prior to administration of the CD8 cells to the individual being treated. It is important to note, however, that unlike other present and proposed treatment modalities, the present method uses a cell culture system (i.e., Drosophila cells) that are not tumorigenic. Therefore, if complete separation of Drosophila cells and activated CD8 cells is not achieved, there is no inherent danger known to be associated with the administration of a small number of Drosophila cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8 cells via intravenous infusion is appropriate.

10. HLA Typing

As noted previously, HLA haplotypes/allotypes vary from individual to individual and, while it is not essential to the practice of the present invention, it is often helpful to determine the individual's HLA type. The HLA type may be determined via standard typing procedures and the PBLs purified by Ficoll gradients. The purified PBLs would then be mixed with syngeneic Drosophila cells preincubated with the appropriate antigenic peptides—e.g., in therapeutic applications relating to viral infections, cancers, or malignancies, peptides derived from viral- or cancer-specific proteins.

Continuing to use viral or malignant conditions as an example, in those instances in which specific peptides of a particular viral- or cancer-specific antigen have been characterized, the synthesized peptides encoding these epitopes will preferably be used. In cases in which the preferred antigenic peptides have not been precisely determined, protease digests of viral- or cancer-specific proteins may be used. As a source for such antigen, cDNA encoding viral- or cancer-specific proteins is cloned into a bacterial expression plasmid and used to transform bacteria, e.g., via methods disclosed herein.

After HLA typing, if Drosophila cells expressing the preferred HLA are not available, cDNAs encoding the preferred HLA may be cloned via use of the polymerase chain reaction. The primers disclosed in section B.1. above (SEQ ID NO 1 through SEQ ID NO 12) may be used to amplify the appropriate HLA-A, -B, -C, -E, -F, or -G cDNAs in separate reactions which may then be cloned and sequenced as described in the methods disclosed for HLA A2.1 below. Stable cell lines expressing the cloned HLA may then be established in the Drosophila cells. Alternatively, a population of insect cells transiently expressing a bulk population of cloned recombinant molecules from the PCR reaction may be used for in vitro CD8 activation.

EXAMPLES

The following examples are intended to illustrate, but not limit, the present invention.

Example 1
Expression of Human Class I MHC Molecules
A. Preparation of pRmHa-3 Expression Vector The pRmHa-3 expression vector for use in expressing MHC proteins in Drosophila Schneider 2 (S2) cells as described in this invention was constructed by ligating a Sph I linearized pRmHa-1 DNA expression vector with a DNA fragment resulting from a Sph I restriction digest of a pRmHa-2 expression vector.as described below. The ligating of pRmHa-1 with the pRmHa-2 fragment in this manner was performed to remove one of two Eco RI restriction endonuclease cloning sites present in pRmHa-1. Thus, the resultant pRmHa-3 expression vector contained only one Eco RI restriction site in the multiple cloning site (polylinker) into which various MHC-encoding DNA fragments were inserted as described in the Examples.

1. Preparation of pRmHa-1 Expression Vector

The pRmHa-1 expression vector, containing a metallothionein promoter, metal response consensus sequences (designated MT) and an alcohol dehydrogenase (ADH) gene containing a polyadenylation signal isolated from *Drosophila melanogaster*, was constructed as described by Bunch et al., *Nucl. Acids Res.* 16: 1043–61 (1988). A schematic of the final pRmHa-1 construct is shown in FIG. 2. The plasmid expression vector, pUC18, having the ATCC accession number 37253, was used as the source vector from which subsequent vectors described herein were derived. The pUC18 plasmid contains the following restriction sites from 5' to 3' in the multiple cloning site, all of which are not illustrated in the schematic representations of the pUC18-derived vectors in FIG. 1: Eco RI; Sac I; Kpn I; Sma I and Sma I located at the same position; Bam HI; Xba I; Sal I, Acc I and Hinc II located at the same position; Pst I; Sph I and Hind III. The pUC18 vector was first digested with Hind III to form a linearized pUC18. Blunt ends were then created by filling in the Hind III ends with DNA polymerase I large fragment as described by Maniatis et al., *Molecular Cloning: A Laboratory Manual*, eds. Cold Spring Harbor Laboratory, New York (1982).

The resultant linearized blunt-ended pUC18 vector was ligated with a 740 base pair (bp) Hinf I fragment from the *Drosophila melanogaster* ADH gene containing a polyadenylation signal. The ligated ADH allele was first isolated from the plasmid pSACI, described by Goldberg et al., *PNAS USA* 77: 5794–5798 (1980), by digestion with Hinf I followed by blunt ending with KLENOW fragment (large fragment of DNA polymerase I) resulting in the nucleotide sequence listed in SEQ ID NO 14. The pSACI vector containing the ADH allele was constructed by subcloning into pBR322 (ATCC accession number 31344) a 4.7 kilobase (kb) Eco RI fragment of Drosophila DNA selected from a bacteriophage labda library containing random, high molecular weight (greater than 15 kb). The 5' Hinf I restriction site occurred naturally in the ADH gene at position 1770 as described by Kreitman, *Nature* 304: 412–417 (1983). The 3' Hinf I site was derived from the pUCl8 vector into which the ADH gene had been cloned. This position was four bases 3' to the Xba I site at position 2500 of the ADH gene. The ADH segment extended from the 35 bp upstream of the polyadenylation/cleavage sequence in the 3' untranslated portion of the ADH mRNA to 700 bp downstream of the polyadenylation signal. The resultant pUC18-derived vector containing the ADH gene fragment was designated pHA-1 as shown in FIG. 1.

The 421 bp Eco RI/Stu I MT gene fragment was obtained from a clone containing DNA of approximately 15.3 kb in a *Drosophila melanogaster* genomic DNA library. The library, prepared with a Mbo I partial digestion of imaginal DNA, was cloned in the lambda derivative EMBL4. The fragment contained the MT promoter and metal response consensus elements of the Drosophila MT gene (Maroni et al., *Genetics* 112: 493–504 (1986)). This region, containing the promoter and transcription start site at nucleotide 1+, corresponded to position −370 to nucleotide position +54 of the MT gene (SEQ ID NO 13). The resultant fragment was then ligated into pHA-1 expression vector prepared above that was previously linearized with Eco RI and Sma I. The 3' blunt end in MT created by the Stu I digest was compatible with the blunt end in pHA-1 created by the Sma I digest. The resultant pUC18-derived vector containing a 5' Drosophila MT gene fragment and a 3' ADH gene fragment was designated pRmHa-1. The pRmHa-1 expression vector, shown in FIG. 2, contained the origin of replication (ori) and the beta-lactamase gene conferring resistance to ampicillin (Amp$^r$) from pUC18 as shown in FIG. 1 on the pHa-1 vector. The diagram of pRmHa-1 also shows the 5' to 3' contiguous positions of the MT gene fragment, the multiple cloning site and the ADH gene fragment. The pRmHa-1 vector was used as described in c. below in the construction of the pRmHa-3 expression vector.

2. Preparation of pRmHa-2 Expression Vector

The construction of pRmHa-2 is shown in FIG. 1. For constructing the pRmHa-2 expression vector, the MT fragment prepared above was inserted into the pUC18-derived vector pHA-1 as described for constructing pRmHa-1 above with a few modifications. An Eco RI linker was added to the Stu I site of the Eco RI/Stu I-isolated MT gene fragment prepared above to form a metallothionein fragment having Eco RI restriction sites on both ends. The resultant fragment was then ligated into the ADH fragment-containing pUC18 expression vector that was previously linearized with Eco RI. The resultant pUC18-derived vector containing a 5' Drosophila MT gene fragment and a 3' ADH gene fragment having two Eco RI restriction sites 5' to the multiple cloning site was designated pRmHa-2. The pRmHa-2 expression vector, shown in FIG. 1, contained the origin of replication (ori) and the beta-lactamase gene conferring resistance to ampicillin (Ampr) from pUC18. The diagram of pRmHa-2 also shows the 5' to 3' contiguous positions of the MT gene fragment, the multiple cloning site and the ADH gene fragment. The pRmHa-2 vector was used along with pRmHa-1 as described in c. below in the construction of the pRmHa-3 expression vector.

3. Preparation of pRmHa-3 Expression Vector

To prepare the pRmHa-3 expression vector that had only one Eco RI restriction site, a fragment from pRmHa-2 was ligated into pRmHa-1. For this construction, pRmHa-2, prepared in b. above, was first digested with Sph I. The resultant Sph I fragment beginning in the middle of the MT gene and extending to the Sph I site in the multiple cloning site was first isolated from the pRmHa-2 vector and then ligated into pRmHa-1 prepared in A.1. above. The pRmHa-1 vector was previously modified to remove the Eco RI restriction site 5' to the MT gene fragment then linearized with Sph I. This process is schematically illustrated in FIG. 2. To remove the Eco RI site in pRmHa-1, the vector was first digested with Eco RI to form a linearized vector, then blunt ended with Mung Bean nuclease and religated.

The pRmHa-1 vector lacking an Eco RI site was then digested with Sph I to remove the region corresponding to the Sph I fragment insert from pRmHa-2 and form a linearized pRmHa-1 vector. The Sph I fragment from pRmHa-2 was then ligated into the Sph I linearized pRmHa-1 to form the pRmHa-3 expression vector. A schematic of the pRmHa-3 vector is shown in FIG. 3. The relative positions of the various restriction sites from the pUC18 vector from which pRmHa-3 was derived are indicated on the figure. In addition, the relative positions and lengths of the MT and ADH gene fragments separated by the multiple cloning site (polylinker) into which the MHC gene of interest is cloned are indicated on the figure. The pRmHa-3 vector, being derived from pUC18, contains the pUC18 origin of replication and beta-lactamase gene conferring ampicillin resistance. Thus, MHC encoding DNA fragments as prepared in this invention and cloned into the multiple cloning site of pRmHa-3 were transcriptionally regulated by the MT promoter and polyadenylated via the ADH gene.

B. cDNA Synthesis

Detailed descriptions of the cDNA of Class I MHC molecules of various HLA groups can be found in U.S. Pat. No. 5,314,813 to Peterson et al. which has been incorporated by reference.

cDNAs encoding any preferred HLA may be cloned via use of the polymerase chain reaction. The primers disclosed in section B.1. above (SEQ ID NO 1 through SEQ ID NO 12) may be used to amplify the appropriate HLA-A, -B, -C, -E, -F, or -G cDNAs in separate reactions which may then be cloned and sequenced as described in the methods disclosed for HLA A2.1 above. Preparation of cDNA from human cells is carried out as described in Ennis, et al., *PNAS USA* 87: 2833–2837 (1990). Briefly, a blood sample is obtained from the individual and cells are collected after centrifugation and used to prepare total RNA. First strand cDNA is synthesized by using oligo(dT) and avian myeloblastosis virus reverse transcriptase. The resulting cDNA is used in a PCR amplification reaction utilizing the appropriate primer(s) as noted in section B.1. above, and a GeneAmp kit and thermal cycler (Perkin-Elmer/Cetus). Reaction conditions are preferably as follows. 100 ng cDNA template and 50 picomoles of each-oligonucleotide primer are used. Thirty cycles are run as follows: (a) one minute at 94° C.; (b) one minute at 60° C.; and (c) one minute, 30 seconds at 72° C. The PCR reaction is then heated to 100° C. for 10 minutes to kill the Taq polymerase and the ends of the DNA made blunt by T4 polymerase (Stratagene, San Diego, Calif.).

To synthesize HLA A2.2, cDNA encoding a complete A2.2 (see Holmes, et al., *J. Immunol.* 139: 936–41 (1987), for the published sequence) is cloned into an M13mp19 plasmid, a commercially available bacteriophage vector (Stratagene, La Jolla, Calif.). cDNA is synthesized by PCR using primers derived from the published sequence of A2. The cDNA is released from an M13mp19 clone as a Not I (overhang filled with KLENOW fragment (large fragment of DNA polymerase I)/Eco RI fragment. (KLENOW fragments are part of the *E. coli* DNA polymerase I molecule, produced by the treatment of *E. coli* DNA pol I with subtilisin. They are used to "fill out" 5' or 3' overhangs at the ends of DNA molecules produced by restriction nucleases.) The Not I/Eco RI fragment is inserted into pSP64T digested with Bg III (ends filled with KLENOW fragment (large fragment of DNA polymerase I) and Eco RI. pSP64T is an SP6 cloning vector designed to provide 5' and 3'flanking regions from an mRNA which is efficiently translated (β-globin) to any cDNA which contains its own initiation codon. This translation SP6 vector was constructed by digesting pSP64-Xβm with Bal I and Bst EII, filling in the staggered ends with T4 DNA polymerase and adding a Bgl II linker by ligation. Bal I cuts the β-globin cDNA two bases upstream of the ATG (start codon) and Bst EII cuts eight bases upstream of the TAA (stop codon). There is only one Bgl II site in pSP64T so that restriction enzymes cutting in the polylinker fragment, from Pst I to Eco RI can still be used to linearize the plasmid for transcription. (See Kreig and Melton, *Nucleic Acid Res.* 12: 7057–7070, (1984), which also describes the construction of the plasmid pSP64-Xβm.) The resulting plasmid is cleaved with Eco RI (end filled with Klenow) and Hind III which is cloned into the pCMUII polylinker between Hind III (5') and Stu I (3'). (See Paabo, et al., *EMBO J.* 5: 1921–1927 (1986).) The entire cDNA is removed as a Hind III (end filled with KLENOW fragment (large fragment of DNA polymerase I) Bam HI fragment which is cloned into pRmHa-3 cleaved with Sma I and Bam HI.

HLA A2.2 soluble form was prepared by engineering a stop codon into the above-described A2.2 cDNA immediately preceding the transmembrane domain. The modification is achieved by cleaving the A2.2 cDNA cloned in the eukaryotic expression vector pCMUII between Hind III 5' and Stu I 3' (see above) with Mbo II and Bam HI inserting the following oligonucleotides:

5' primer: 5' GGAGCCGTGACTGACTGAG 3' (SEQ ID NO 17)

3' primer: 5° CCCTCGGCACTGACTGACTCCTAG 3' (SEQ ID NO 18)

The resulting recombinant plasmid is cleaved with Hind III, the overhanging end filled with KLENOW fragment (large fragment of DNA polymerase I), then cut with Bam HI releasing a restriction fragment which is cloned into pRmHa-3 in the same way as A2.2 full length.

1. Construction of Murine ICAM-1 Expression Vector

Spleen cells were isolated from Balb/c mice. The spleen cells were stimulated with cona; mRNA was isolated using the FastTrack kit (Invitrogen, San Diego, Calif.) according to the manufacturers' instructions. cDNA was synthesized from the mRNA using AMV reverse transcriptase kit (Promega, Madison, Wis.) according to the manufacturers' instructions. Based on the published cDNA nucleotide sequence (Siu, G. et al., J. Immunol. 143, 3813–3820 (1989) the following oligonucleotides were synthesized as PCR primers:

5': TTTAGAATTCAC CATGGCTTCA ACCCGTGCCA AG (SEQ ID NO 46)

3': TTTAGTCGACTC AGGGAGGTGG GGCTTGTCC (SEQ ID NO 47)

The cDNA synthesized was subjected to PCR using these primers. The product was cleaved with the restriction enzymes Eco RI and Sal I and ligated into pRmHa-3, which had been digested with the restriction enzymes Eco RI and Sal I.

2. Construction of Murine B7.1 Expression Vector

Spleen calls were isolated from Balb/c mice and stimulated with conA. Messenger RNA was isolated using the FastTrack kit (Invitrogen, San Diego, Calif.) according to the manufacturer's instructions. cDNA was synthesized from the mRNA using AMV reverse transcriptase kit (Promega, Madison, Wis.) according to the manufacturer's instructions.

Based on the published cDNA nucleotide sequence (Freeman, et al., J. Exp. Med. 174: 625–631 (1991)) the following oligonucleotides were synthesized as PCR primers:

5': TTTAGAATTCAC CATGGCTTGC AATTGTCAGT TG (SEQ ID NO 48)

3': TTTAGTCGACCT AAAGGAAGAC GGTCTGTTC (SEQ ID NO 49)

The cDNA synthesized was subjected to PCR using these primers. The product was cleaved with the restriction enzymes Eco RI and Sal I and ligated into pRmHa-3, which had been digested with the restriction enzymes Eco RI and Sal I.

3. Construction of Murine B7.2 Expression Vector

IC-21 cells (obtained from ATCC) were propagated in RPMI 1640 medium containing 10% Fetal Calf Serum. mRNA was isolated from these cells using the FastTrack kit (Invitrogen, San Diego, Calif.) according to the manufacturer's instructions. cDNA was synthesized from the mRNA using AMV reverse transcriptase kit (Promega, Madison., Wis.) according to the manufacturer's instructions. Based on the published cDNA nucleotide sequence (Freeman, et al., J. Exp. Med. 178: 2185–2192 (1993)) the following oligonucleotides were synthesized as PCR primers:

5': TTTAGAATTCAC CATGGACCCC AGATGCACCA TGGG (SEQ ID NO 50)

3': TTTAGTCGACTC ACTCTGCATT TGGTTTTGCT GA (SEQ ID NO 51)

The cDNA synthesized was subjected to PCR using these primers. The product was cleaved with the restriction enzymes Eco RI and Sal I and ligated into pRmHa-3, which had been digested with the restriction enzymes Eco RI and Sal I.

The above expression constructs were transfected into Drosophila S2 cells using the calcium phosphate method as listed in Table 1. Stable cell lines were selected by including 500 μg/ml Geneticin in the cell culture medium.

TABLE 1

| Transfected Cells | | MHC I ($L^d$) μg | β2 μg | B7.1 (CD 80) μg | B7.2 μg | ICAM-1 (CD54) μg | phsneo μg |
|---|---|---|---|---|---|---|---|
| 1 | A | 12 | 12 | | | | 1 |
| 2 | B | 8 | 8 | 8 | | | 1 |
| 3 | C | 8 | 8 | | 8 | | 1 |
| 4 | C | 8 | 8 | | | 8 | 1 |
| 5 | D | 6 | 6 | 6 | | 6 | 1 |
| 6 | E | 6 | 6 | | 6 | 6 | 1 |
| 7 | F | 6 | 6 | 6 | 6 | | 1 |
| 8 | G | 4.8 | 4.8 | 4.8 | 4.8 | 4.8 | 1 |

Human accessory and costimulatory molecules were cloned from human cell lines demonstrated to express these proteins by FACS analysis with monoclonal antibodies specific for the particular proteins. Adhesion molecules belonging to the integrin family, ICAM-I (CD54) and LFA-3 (CD58), were cloned from human cell lines K562 and HL60, respectively. The K562 cells, originated from human chronic myelogenous leukemia, were obtained from ATCC (CCL-243) and cultured under conditions recommended (i.e., RPMI with 10% fetal calf serum at 37 degrees C. with 5% $CO_2$). HL60 cells, originated from a human promyelocytic leukemia, and were obtained from ATCC (CCL-240) and were cultured according to ATCC's recommendations. Costimulatory molecules B7.1 and B7.2 were also cloned from K562 and HL60 cells respectively.

4. cDNA

Messenger RNA samples were prepared from each cell line from RNA isolated by the modified guanidinium thiocyanate method (Chromczynski, et al. *Anal. Biochem.* 162: 156–159, 1987) followed by poly A+ RNA selection on oligo(dt)-cellulose columns (Sambrook, J., et al, *Molecular Cloning: A Laboratory Manual, Second Edition*, 6.22–6.34, Cold Spring Harbor laboratory, CSH, N.Y.), Induction of HL60 cells with vitamin D3 (usually required to express some cell surface molecules) was not required to obtain the B7.2 and LFA-3 molecules, the proteins were expressed in the absence of induction. cDNA was prepared using AMV reverse transcriptase kit according to the manufacturers' instructions (Promega, Madison Wis.).

5. PCR Primers

PCR primers were designed and synthesized after obtaining copies of the known sequences from the GENEWORKS database (Intelligenetics) and considering the ends needed to clone into the appropriate vectors. They are as follows with the top sequence of each protein the 5' primer and the bottom one the 3' primer:

B7.1 5'-ACCCTTGAAT CCATGGGCCA CACACGGAGG CAG-3' (SEQ ID NO 52)

5'-ATTACCGGAT CCTTATACAG GGCGTACACT TTCCCTTCT-3' (SEQ ID NO 53)

B7.2 5'-ACCCTTGAGC TCATGGATCC CCAGTGCACT ATG-3' (SEQ ID NO 54)

5'-ATTACCCCCG GGTTAAAAAC ATGTATCACT TTTGTCGCAT GA-3' (SEQ ID NO 55)

LFA-3 5'-ACCCTTGAGC TCATGGTTGC TGGGAGC-GAC GCGGGG-3' (SEQ ID NO 56)

3'-ATTACCGGAT CCTTAAAGAA CATTCATATA CAG-CACAATA CA-3' (SEQ ID NO 57)

ICAM-1 5'-ACCCTTGAAT TCATGGCTCC CAGCAGC-CCC CGGCCC-3' (SEQ ID NO 58)

3'-ATTACCGGAT CCTCAGGGAG GCGTGGCTTG TGTGTTCGG-3' (SEQ ID NO 59)

6. Expression of DNA Fragment

The cNDA preparations from each of the cell lines was used to clone the desired proteins. The polymerase chain reaction was used to generate cDNA fragments utilizing the appropriate PCR primer (see above). The appropriate DNA fragments were cloned into the Drosophila fly vector pRMHA-3. Plasmid preparations have been prepared from all of the preparations and are now ready for transfection into the fly cells.

Human β-2 microglobulin cDNA is prepared using a published partial cDNA sequence (see Suggs, et al., *PNAS* 78: 6613–17, 1981) is used as a template for a polymerase chain reaction (PCR) with the following primers:

5' primer
5' GCTTGGATCCAGATCTACCAT-GTCTCGCTCCGTGGCCTTAGCTGTGCTCGC GCTACTCTC 3'
(SEQ ID NO 15)

3' primer
5' GGATCCGGATGGTTACATGTCGCGATC-CCACTTAAC 3'
(SEQ ID NO 16)

The primers are used in a standard PCR reaction (see Nilsson, et al., *Cell* 58: 707 (1989)). The reaction products are extracted with phenol, purified using a Geneclean kit (Bio 101, San Diego, Calif.), digested with Bam HI and cloned into the Bam HI site of pBS (Stratagene, La Jolla, Calif.). After verification of the sequence, this Bam HI fragment is cloned into the Bam HI site of pRmHa-3.

As noted in the Examples, murine Class I cDNA was utilized in various instances. Murine Class I cDNA was prepared as follows.

H-2$K^b$: cDNA encoding a complete $K^b$ molecule is obtained from an expression plasmid pCMU/$K^b$ constructed as follows. A partial H-2$K^b$ cDNA missing the leader sequence and most of the alpha I domain is prepared according to the method of Reyes, et al., *PNAS* 79: 3270–74 (1982), producing pH202. This cDNA is used to generate a full-length molecule. The missing sequence is provided using a genomic clone encoding H-2$K^b$ (Caligan, et al., *Nature* 291: 35–39, 1981) as a template in a PCR reaction, using a 5' primer flanked by a Not I site, followed by 21 nucleotides encoding the last seven amino acids of the leader sequence and 18 nucleotides complementary to the beginning of the alpha I domain and a 3' primer complementary to the region encompassing the Sty I site. The resulting fragment is ligated with pH202 at the Sty I site. The 5' sequence encoding the remainder of the signal sequence is obtained form the Db cDNA (see below) as a Bam HI/Not I fragment. The entire coding sequence is cleaved from the expression plasmid as a Bam HI fragment and cloned into pRHma-3 cleaved with Bam HI.

H-2$L^d$: cDNA encoding a complete $L^d$ molecule is obtained from an expression plasmid pCMUIV/$L^d$ (see Joly and Oldstone, *Gene* 97: 213, 1991). The complete cDNA is cleaved from a eukaryotic expression vector pCMU IV/$L^d$ as a Bam HI fragment and cloned into pRmHa-3 as $K^b$.

As noted previously, the pCMU vector (pCMUIV) is derived from eukaryotic expression vector pC81G as described in Nilsson, et al., supra. Vector pC81G, in turn, is derived from pA81G (Paabo, et al., *Cell* 33: 445–453 (1983)) according to the method disclosed in Paabo, et al., *EMBO J.* 5: 1921–7 (1986).

H-2$D^b$: cDNA encoding a complete $D^b$ molecule is obtained from expression plasmid pCMUIV/$D^b$ (see Joly and Oldstone, *Science* 253: 1283–85, 1991). The complete cDNA is cleaved from a eukaryotic expression vector pCMUIV/D$^b$ as a Bam HI fragment and cloned into pRmHa-3 as K$^b$.

Murine β-2 microglobulin: full-length murine β-2 microglobulin cDNA is obtained as a Hind III (5') (filled with KLENOW fragment (large fragment of DNA polymerase I))/Bgl II (3') fragment from pSV2neo (ATCC No. 37149) mouse β-2 microglobulin cDNA and cloned into pRHma-3 cleaved with Sma I and Bam HI.

Vector phshsneo confers neomycin (G418) resistance and is a derivative of phsneo (pUChsneo) with an additional heat-shock promoter (hs) sequence, which may be synthesized from commercially-available pUC8 as described in Steller, et al., *EMBO J.* 4: 167 (1985). The heat shock promoter contained in these vectors is the hsp70 promoter. Other useful vectors conferring neomycin resistance (G418 resistance) include cosmid vector smart2 (ATCC 37588), which is expressed under the control of Drosophila hsp70 promoter, and plasmid vector pcopneo (ATCC 37409).

C. Insertion of Genes into Expression Vectors

The restriction products are subjected to electrophoresis on a 1% agarose gel (Maniatis, et al., *Molecular Cloning: A Laboratory Manual*, Cold Spring Harbor Laboratory (1982)). The restriction fragments encoding the cDNAs are excised from the gel and purified away from the agarose using "Geneclean", according to manufacturers' directions (Bio 101, San Diego, Calif.). The expression plasmid pRmHa-3 (FIG. 3) is cleaved with the appropriate restriction enzymes in One Phor All buffer according to the manufacturer's directions (Pharmacia, Piscataway, N.J.) and treated with alkaline phosphatase as described in the manufacturer's literature (Boehringer Mannheim, Indianapolis, Ind.). One hundred ng of cleaved and phosphatased pRmHa-3 vector is mixed with 300 ng of agarose gel purified Class I MHC heavy chain cDNA or β-2 microglobulin cDNA and ligated using T4 DNA ligase and One Phor all buffer as described in the manufacturers' literature. After incubation at 16° C. for five hours, the ligation mixture is used to transform competent *E. coli* JM83 (Maniatis, et al., supra (1982)).

Methods disclosed in Maniatis, et al., supra are used to prepare the cDNA needed. The presence of the MHC heavy chain cDNA and its orientation in the vector is determined by restriction mapping. Bacteria containing the vector with the cDNA in the correct orientation relative to the metallothionein promoter are used for large scale preparation of DNA using the alkaline lysis method and cesium chloride gradient purification. The amount of DNA obtained is determined spectrophotometrically.

D. Transfection and Labeling of S2 Cells

S2 cells are grown in Schneider medium (Gibco/BRL, Grand Island, NY) supplemented with 10% fetal calf serum (heat treated for one hour at 55° C.), 100 units/ml penicillin, 100 mg/ml streptomycin, and 1 mM glutamine. (For convenience, this supplemented medium is hereinafter referred to as Schneider medium.) Cells are grown at 27° C. and typically passaged every seven days by diluting 1:17 in fresh medium. Cells are converted to growth in serum free media (Excell 400 or 401 supplemented with 100 units/ml penicillin, 100 mg/ml streptomycin, 1 mM glutamine, and 500 g/ml G418 (JRH Biosciences, Lenexa, Kans.) by initial dilution at 50% Schneider/50% Excell 401. One week later, cells may be passaged into 10% Schneider medium/90% Excell 401 and one week later into 100% Excell 401. Cells are maintained in this medium and passaged every seven days by diluting 2:17 in fresh medium.

$15 \times 10^6$ S2 cells at a concentration of $10^6$ cells per ml are plated out in 85 mm petri dishes. Twelve hours later, calcium phosphate/DNA precipitates, prepared as described below (1 ml) are added dropwise to the cells. After 48 hours, the supernatant is carefully removed and the cells transferred to a 175 cm$^2$ flask in a total volume of 50 ml in Schneider medium containing 500 g/ml Geneticin (G418) (Gibco/BRL, Grand Island, N.Y.). After 21 days, 20 ml of the culture is removed to a fresh flask containing 30 ml of Schneider medium containing 500 μg/ml G418. Ten days later, a stable population of cells that weakly adhered to the flask and grew with a doubling time of approximately 24 hours is obtained and these cells are subsequently cultured and passaged in the selection media as described above. Frozen aliquots of these cells are prepared by collecting 5–20×10$^6$ cells by centrifugation and resuspending them in 1 ml of cell freezing media (93% fetal calf serum/7% dimethylsulfoxide). Aliquots are then placed at –70° C. for one week and subsequently transferred to liquid nitrogen storage.

Calcium phosphate precipitates are prepared as described by Paabo, et al. (*EMBO J.* 5: 1921–27 (1986)), except that 25 μg of DNA is used per transfection. The following combinations of DNA are used to prepare the indicated transfectant:

(a) MHC Class I heavy chain alone: 23 μg heavy chain expression vector DNA +2 μg of phshsneo DNA.

(b) MHC Class I heavy chain +β-2 microglobulin: 11.5 μg heavy chain expression vector DNA +11.5 μg of β-2 microglobulin (human or mouse) expression vector DNA +2 μg of phshsneo DNA.

Other combinations of mouse genes are presented in Table 1.

Twenty-four hours prior to metabolic labeling, cells are plated out at a cell density of 3–5×10$^6$ cells/ml (10 ml/85 mm petri dish) in Schneider medium containing 1 MM CuSO$_4$. Thirty minutes prior to labelling the medium is aspirated from the dishes and the cells are washed with 2×10 ml of PBS and then incubated in Graces insect medium minus methionine and cysteine (special order from Gibco/BRL, Grand Island, N.Y.) for 20 minutes, and then in 1 ml of this medium containing 0.1 mCi $^{35}$S Trans label (New England Nuclear; duPont, Boston, Mass.). After the labelling period, the labelling solution is aspirated and the cells are either lysed immediately on ice, with ice cold PBS/1% Triton X100 (1 ml) or after a chase period in the presence of methionine containing Schneider or Excell 400 medium (5 ml) (JRH Biosciences). The chase medium is collected if soluble Class I MHC molecules are being analyzed.

The following operations are all carried out with the lysates kept cold (less than 8° C.). The lysates were collected into Eppendorf tubes, centrifuged in a microfuge tube for 15 minutes at 13,000×g, transferred to a fresh tube containing 100 μl of a 10% slurry of protein A sepharose and placed on an end-over-end rotator for two hours. Following a further centrifugation in the microfuge for 15 minutes, the cell lysates are ready for analysis.

In experiments utilizing murine MHC, S2 cells were transfected with the murine MHC recombinants described above using the CaPO$_4$ precipitation method; each heavy chain is transfected either alone or as a 50:50 mix with the vector encoding β-2 microglobulin. A plasmid encoding neomycin resistance, phshsneo DNA, is included in each transfection such that a population of cells that stably expressed MHC Class I could be obtained by growing the transfectants in selection medium (Geneticin G418-sulphate, Gibco/BRL, Grand Island, N.Y.).

E. Peptide Generation

Antigenic peptides according to the present invention may be obtained from naturally-occurring sources or may be synthesized using known methods. In various examples disclosed herein, peptides are synthesized on an Applied Biosystems synthesizer, ABI 431A (Foster City, Calif.) and subsequently purified by HPLC.

Isolation or synthesis of "random" peptides may also be appropriate, particularly when one is attempting to ascertain a particular epitope in order to load an empty MHC molecule with a peptide most likely to stimulate precursor CD8 cells. One may produce a mixture of "random" peptides via use of proteasomes (see, e.g., Example 2.B.6) or by subjecting a protein or polypeptide to a degradative process—e.g., digestion with chymotrypsin—or peptides may be synthesized. While we have observed that the cell lines of the present invention are able to degrade proteins and polypeptides into smaller peptides capable of being loaded onto human Class I MHC molecules, it is preferable to introduce smaller peptides—e.g., 8-mers and 9-mers—directly into the cell culture to facilitate a more rapid loading and expression process.

If one is synthesizing peptides, e.g., random 8-, 9- and 18-amino acid peptides, all varieties of amino acids are preferably incorporated during each cycle of the synthesis. It should be noted, however, that various parameters—e.g., solvent incompatibility of certain amino acids—may result in a mixture which contains peptides lacking certain amino acids. The process should thus be adjusted as needed—i.e., by altering solvents and reaction conditions—to produce the greatest variety of peptides.

As noted hereinabove, murine heavy chains complexed with human $\beta$-2 microglobulin were stable at temperatures approximately 6–8 degrees higher than if complexed with murine $\beta$2. It was also observed that the stabilities imparted by peptide and xenogeneic $\beta$-2 microglobulin are additive. A large increase in the thermostability of the Class I molecules occurs if 8–9 mers are used, as compared to 12–25 mers; indeed, the difference between the stabilization imparted by the 8–9 mers compared with the larger peptides might be even greater than what was observed previously, for even though the peptides have been purified by HPLC, it is likely that there is some contamination of the larger peptides by 8–9 mers.

It is now shown that the thermostability of a Class I molecule is apparently dependent on: (1) the origin of $\beta$-2 microglobulin; (2) the presence of peptide; and (3) the length and sequence of this peptide.

Previous work (U.S. Pat. No. 5,314,813 to Peterson et al.; Jackson et al., *PNAS USA* 89: 12117–12121 (1992)) has shown that Class I MHC heavy chains can bind peptide either alone or when they are associated with $\beta$-2 microglobulin. Surface expression of peptide-loaded human Class I MHC, however, appears to be best facilitated by loading the molecules with peptide after the heavy chains have complexed with $\beta$-2 microglobulin.

1. Expression of Human MHC

Once we determined that the thermostability of is a Class I molecules is dependent on the origin of $\beta$-2 microglobulin, the presence of peptide, and the length and sequence of this peptide, we utilized this information in the creation of cell lines capable of specifically activating CD8 cells via the expression of peptide-loaded human Class I MHC molecules.

Thermolability appears to be an inherent property of Class I molecules; it has presumably evolved to ensure that Class I molecules which contain either no peptide or a peptide of poor binding properties (that confers little thermostability) self-destruct. In this way, the cell minimizes the number of empty Class I molecules on its surface, for such a situation would presumably be dangerous in that exogenously derived peptides could be bound and presented. Human Class I molecules expressed in insect cells with human $\beta$2 are not stable to extended incubation at 37° C.; neither are human Class I molecules expressed in the mutant cell line T2 which has been shown to be deficient in peptide loading onto the Class I molecules (Hosken and Bevan, *Science* 248: 367–70 (1990); Cerundolo, et al., *Nature* 345: 449–452 (1990)). Thus, it seems that the affinity between the heavy chain and $\beta$-2 microglobulin has been carefully conserved through co-evolution of the molecules such that empty Class I molecules, or those carrying poorly-binding peptides, self-destruct at the body temperature of the "host" organism.

Human Class I MHC molecules were expressed in S2 cells. Cell lines co-expressing human $\beta$-2 microglobulin and HLA A2.2Y, HLA A2.1, HLA B7, or HLA B27 were established using previously-described methods. Briefly, cDNAs encoding the above proteins were cloned into the Drosophila expression vector pRHma-3 and cotransfected with a human $\beta$-2 microglobulin-containing plasmid and phshsneo plasmid into S2 cells via methods disclosed herein. Three to four weeks later, the population of G418-resistanT-cells was diluted 1:5 with fresh selection media. Once a healthy growing population of cells was obtained, $CuSO_4$ was added to an aliquot of cells and 24 hours later, cells were analyzed via flow cytometry using a monoclonal antibody W6/32 (ATCC HB95, Bethesda, Md.) which recognizes a monomorphic determinant of human Class I heavy chains when they are in association with $\beta$-2 microglobulin. (See Barnstable, et al., *Cell* 14: 9 (1978).) High levels of surface expression of each of the human Class I molecules were induced by the addition of $CuSO_4$ (data not shown). These stable populations were sorted for high expressing cells using cytofluorimetry as described below. It is these sorted populations of cells which were used for all subsequent experiments.

Twenty-four hours prior to FACS analysis, $CuSO_4$ is added to the stably transfected S2 cells ($3–4\times10^6$ cells/ml) to a final concentration of 1 mM, thereby "switching on" expression from the transfected genes. Cells are plated out in 24-well cluster dishes (2 ml per well). Eight hours prior to FACS analysis, the $CuSO_4$ medium is replaced with fresh medium (1 ml) with or without peptide at a concentration of 50 $\mu$g/ml. 37° C. temperature challenges are carried out by transferring the dishes onto a flat surface in a 37° C. room at various time intervals prior to harvesting the cells for analysis.

To analyze surface expression of Class I MHC on the S2 cells, aliquots of cells ($5\times10^5$) are transferred into tubes on ice, collected by centrifugation (1,000×g for 4 minutes), resuspended in 3 ml of PBS/1% BSA, 0.02% sodium azide, collected by centrifugation and resuspended in PBS/BSA (0.5 ml) containing the appropriate primary antibody (ascites fluids Y3, 28:14:8S, 30.5.7, W6/32, diluted 1:200). Rabbit antisera are diluted 1:500 and B22.293 hybridoma supernatant is used directly. After a one hour incubation on ice, cells are washed twice in 3 ml of PBS/BSA and resuspended in 0.5 ml of PBS/BSA containing FITC labelled secondary antibody (Cappell, Durham, N.C.) and 1 ng/ml propidium iodide. After a 30 minute incubation on ice, cells are washed once with PBS/BSA and resuspended in this buffer at a concentration of $1\times10^6$/ml. Samples are then analyzed by FACS 440 (Becton Dickinson). Dead cells stained with propidium iodide, are excluded by including a live gate in the analysis.

For cell sorting, the same procedure outlined above is used, except that all staining operations are carried out in a sterile hood. Solutions, including antibodies, are filter-sterilized, and Schneider media or Excell 400 is used in place of PBS/BSA. Cells that specifically bound the primary antibody are sorted using a Becton Dickinson cell sorter. Sorted cells ($2-8\times10^5$) are washed once in medium before plating out at a concentration of $2\times10^5$ cells/ml.

F. Loading of Membrane-Bound Empty MHC Molecules by in vitro Incubation with Peptides In order to demonstrate that the human Class I molecules expressed on the surface of the Drosophila cells were empty, the cells were incubated at 37° C. for two hours and the cell surface expression was analyzed by cytofluorimetry. The surface expression of both HLA B27 and A2.1 is greatly reduced if cells are incubated at 37° C. for 2 hours; however, preincubating the cells in HIV peptides known to bind to the Class I molecules affords significant thermal stability to the Class I, while peptides that do not bind have little effect (see FIG. 4). (A 9-amino acid peptide ILKEPVHGV (SEQ ID NO 42) from the POL protein of HIV binds and stabilizes HLA A2.1. A nine-amino-acid peptide from the Vpr protein of HIV binds and stabilizes B27 (FRIGCRHSR; SEQ ID NO 41). These data show that the human Class I molecules expressed on the surface of Drosophila cells are empty and can be stabilized by binding specific HIV peptides.

Figure 4:
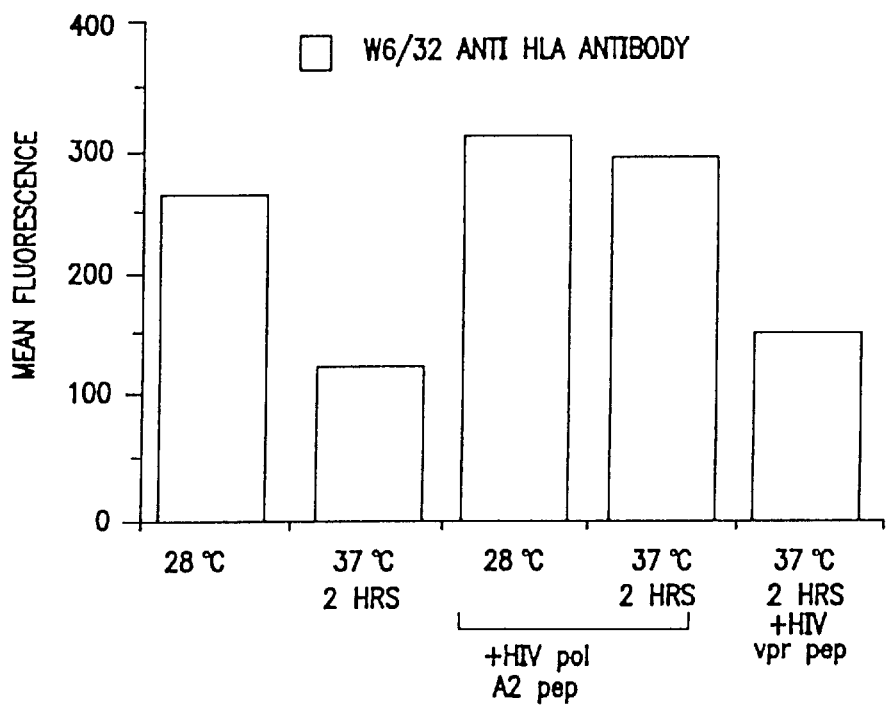
FIGS. 4 and 5 show peptide-induced thermostabilization of HLA B27 and HLA A2.1 expressed on the surface of Drosophila cells by HIV peptides. The mean fluorescence of each cell population is shown plotted against the incubation conditions.
Figure 5:
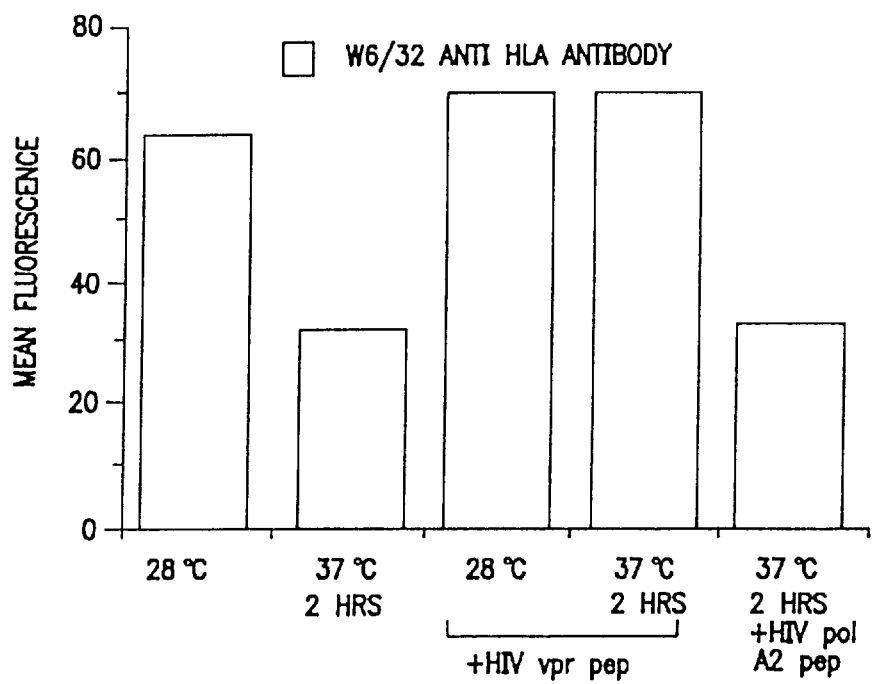

FIGS. 4 and 5 show peptide-induced thermostabilization of HLA B27 and HLA A2.1 expressed on the surface of Drosophila cells by HIV peptides. Drosophila cells expressing either HLA B27 or A2.1 were incubated with peptides where indicated and then either maintained at 28° C. or incubated at 37° C. for two hours prior to analysis of the surface expression of the Class I molecules by use of the antibody W6/32 (from ATCC HB95) and cytofluorimetry. The mean fluorescence of each cell population is shown plotted against the incubation conditions The HIV POL peptide (ILKEPVHGV, SEQ ID NO 42) stabilizes A2.1 but not B27 (FIG. 4), while the HIV Vpr peptide (FRIGCRHSR, SEQ ID NO 41) stabilizes B27, but not A2.1 (FIG. 5).

Example 2
Preparation of Synthetic Antigen-Presenting Cells

A. Osmotic Loading

Osmotic loading of SC2 and 3T3 cells with ovalbumin protein was carried out as described by Moore, et al., *Cell* 54: 777–785 (1988). The assay procedure is as follows. In a 96-well dish, $1\times10^5$ Drosophila cells (with or without peptide/protein loaded) or 3T3 cells were cocultured with $1\times10^5$ B3/CD8 T-cell hybridoma cells in 200 μl of RPMI media supplemented with 10% fetal bovine serum. After 24 hours of incubation, 100 μl of the supernatant from these cultures was added to 100 μl of RPMI containing 5,000 CTLL cells. The cells were cocultured for 24 hours at 37° C. when 1 μCi of $^3$H thymidine (Amersham) was added. After a further incubation of 15 hours at 37° C., the incorporation of radiolabel into the CTLL cells was determined by scintillation counting.

Assays conducted with murine MHC also verified that the insect cells are capable of loading peptide onto the Class I molecules. Cells expressing as few as 200–500 MHC molecules containing a particular antigen can be detected by a T-cell. As the Drosophila cells do not accumulate chromium, an antigen presentation assay based on B3/CD8, a T-cell hybridoma, was used. B3/CD8 is a hybridoma between B3, cytotoxic T-cell specific for ovalbumin peptide 253–276 presented by H-2K$^b$ Class I molecules, and CD8- bearing IL-2-secreting cell line (see Carbone, et al., supra, 1989). Upon antigenic stimulation, B3/CD8 produces IL-2, measured by $^3$H thymidine incorporation in IL-2-dependenT-cell line CTLL (Gillis, et al., *J. Immunol.* 120: 2027 91978)). Thus, by measuring the amount of IL-2 produced, one can assay for T-cell recognition.

In order to provide an intracellular pool of ovalbumin protein from which OVA peptides can be derived, ovalbumin (Sigma Chem. Co., Mo.) was osmotically loaded into the cells as described by Moore, et al, supra (1988). Immediately after loading, the cells were mixed with the T-cell hybridoma. After two days' incubation, the medium was removed and assayed for IL-2. The amount of IL-2 was determined by the ability of the medium to support the growth of the IL-2-dependenT-cell line CTLL (Gillis, et al., supra, 1978), and growth was quantitated by the amount of radioactive thymidine incorporated into the cells.

S2 or 3T3 cells transfected with $K^b/\beta 2$ were incubated with ovalbumin protein (OvPro) or ovalbumin peptide, OVA 24 (OvPep) in isotonic (Iso) or hypertonic (Hyp) media. (Murine cell line BALB/3T3 is available from the ATCC under accession number CCL 163.) After treatment, cells were cocultured with the T cell hybridoma B3/CD8. B3/CD8 is a T cell hybridoma between B3 (Carbone, et al., *J. Exp. Med.* 169: 603–12 (1989)), cytotoxic T cell specific for ovalbumin peptide 253–276 presented by H-2K$^b$ Class I molecules, and CD8- bearing IL-2-secreting cell line. Upon antigenic stimulation, B3/CD8 produces IL-2, measured by $^3$H thymidine incorporation in IL-2-dependent cell line CTLL (Gillis, et al., *J. Immunol.* 120: 2027 91978)). Thus, by measuring the amount of IL-2 produced, one can assay for T cell recognition. The supernatant from the cocultures were analyzed for IL-2 by $^3$H thymidine incorporation by the IL-2-dependent cell line CTLL (ATCC No. TIB 214). The amount of $^3$H thymidine incorporated is plotted against the initial cell treatments.

Figure 6:
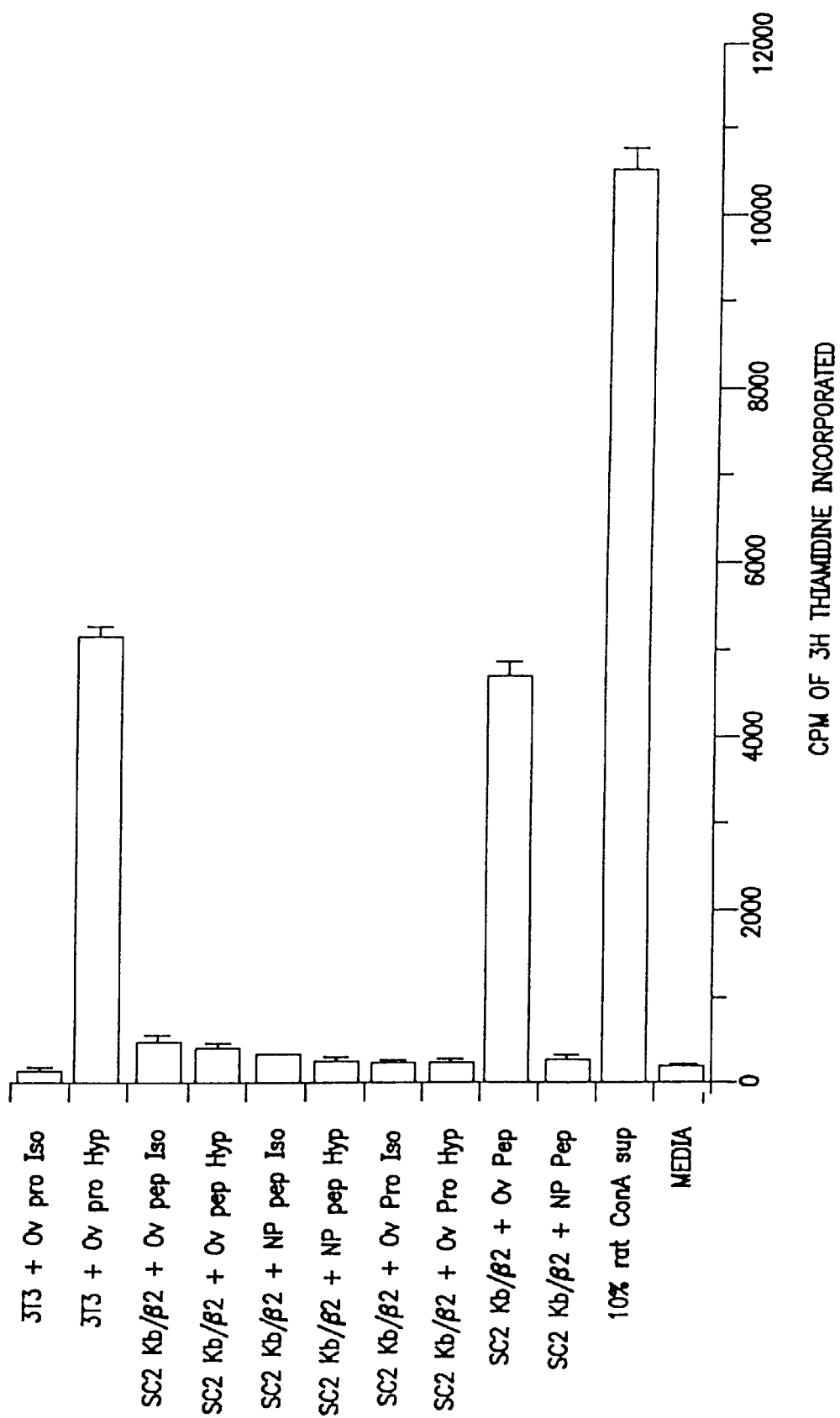
FIG. 6 illustrates data from an experiment designed to determine whether insect cells can process antigen and load it onto the Class I molecules, and whether the latter can present either endogenously or exogenously derived antigen to T cells. Schneider 2 (SC2) or 3T3 cells transfected with $K^b/\beta 2$ were incubated with ovalbumin protein (OvPro) or ovalbumin peptide, OVA 24 (OvPep) in isotonic (Iso) or hypertonic (Hyp) media. (Murine cell line BALB/3T3 is available from the ATCC under accession number CCL 163.) After treatment, cells were cocultured with the T cell hybridoma B3/CD8. B3/CD8 is a T cell hybridoma between B3 (Carbone, et al., *J. Exp. Med.* 169: 603–12 (1989)), cytotoxic T cell specific for ovalbumin peptide 253–276 presented by $H-2K^b$ Class I molecules, and CD8- bearing IL-2-secreting cell line. Upon antigenic stimulation, B3/CD8 produces IL-2, measured by $^3H$ thymidine incorporation in IL-2-dependent cell line CTLL (Gillis, et al., *J. Immunol.* 120: 2027 91978)). Thus, by measuring the amount of IL-2 produced, one can assay for T cell recognition. The supernatant from the cocultures were analyzed for IL-2 by $^3H$ thymidine incorporation by the IL-2-dependent cell line CTLL (ATCC No. TIB 214). The amount of $^3H$ thymidine incorporated is plotted against the initial cell treatments.

It can be seen in FIG. 6 that the T-cells responded well to the Drosophila cells if the ovalbumin peptide was added to the culture medium, but no recognition occurred if the cells were loaded with the ovalbumin protein. The MHC Class I molecules expressed on the cell surface of the insect cell are fully functional in that they can bind peptide if it is added to the culture medium and can present it in the correct context for it to be recognized by a T-cell.

B. Optimization of In Vitro Conditions

For the optimization of in vitro conditions for the generation of specific cytotoxic T-cells, the culture of Drosophila cell stimulator cells is preferably maintained in serum-free medium (e.g. Excell 400). Drosophila cell stimulator cells are preferably incubated with >20 μg/ml peptide. The effector:stimulator ratio (lymphocyte:Drosophila cell ratio) is preferably in the range of about 30:1 to 300:1. The maximum specific CD8 is generally observed after five days of culture. The culture of target cells for killing assay is preferably maintained in a serum-free medium.

Example 3
Stimulation of Proliferation and Differentiation of Armed Effector T-Cells We have found that Drosophila S2 cells transfected with MHC class I molecules and specific assisting molecules are able to stimulate primary responses from T-cells in vitro. We present data below in this example from a mouse model system. In this example, constructs coding for mouse MHC class I ($L^d$) molecules, $\beta 2$ microglobulin, specific assisting molecules and CD8 cells from lymph nodes of T-cell receptor transgenic mice.

Figure 7:
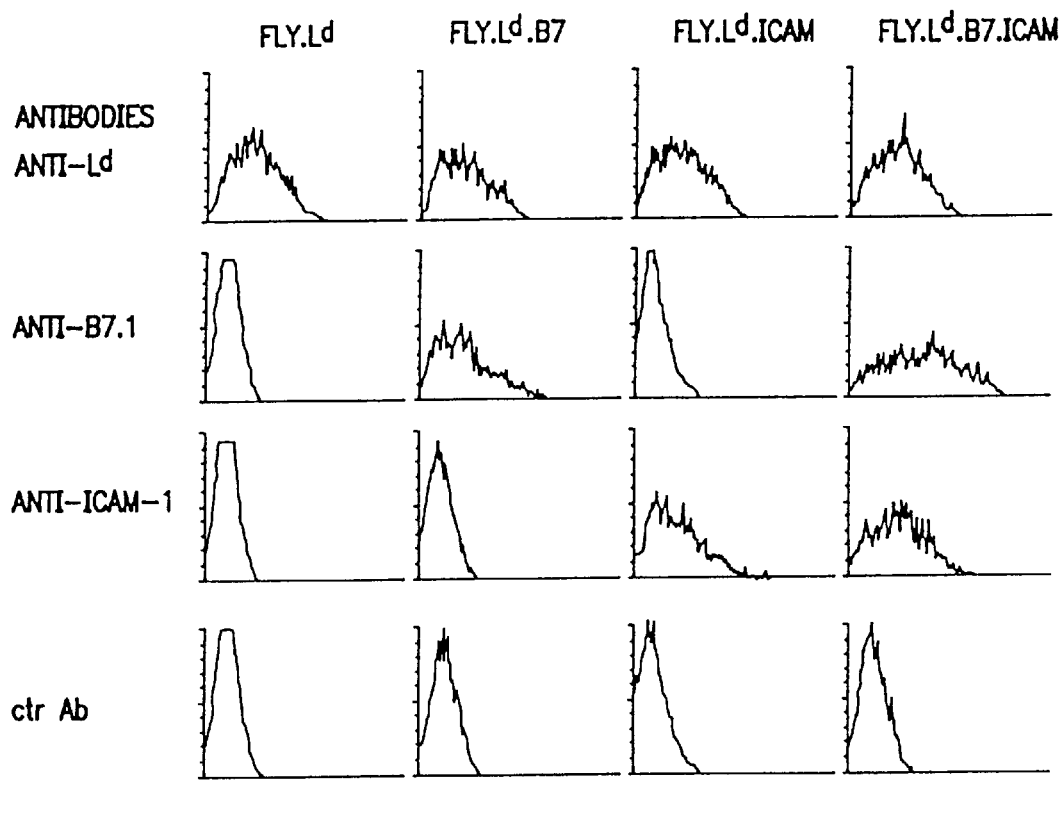
FIG. 7 illustrates the expression of B7.1, ICAM-1 and MHC on the surface of transfected Drosophila (fly) cells according to the present invention.

The data in FIG. 7 provides evidence that the transfected Drosophila S2 cells express the protein products of the transfected murine genes. Flow cytometry using a fluorescence-activated cell sorter (FACS) and fluorescently labelled antibodies were used to demonstrate the expression of class I ($L^d$) and the specific assisting molecules B7.1 (CD80) and ICAM-1 (CD54) molecules by transfected Drosophila S2 cells. Transfected cells were separated with a FACS to obtain cells expressing $L^d$ molecules and were then maintained in vitro.

The transfection of Drosophila S2 cells is summarized in Table 2. The data show $L^d$, B7.1 and ICAM-1 expression measured by flow cytometry on the cell lines after induction with $CuSO_4$. It is apparent that, relative to the control antibody (ctr Ab), all of the transfectants express $L^d$ molecules on the cell surface. Likewise, cells cotransfected with $L^d$ and B7.1 ($L^d$. B7) express B7.1 but not ICAM-1, whereas cells cotransfected with $L^d$ and ICAM-1 ($L^d$.ICAM) express ICAM-1 but not B7.1; triple transfection with $L^d$, B7.1 and ICAM-1 ($L^d$.B7. ICAM) led to expression of all three molecules.

Using a standard tissue culture system (Cai, Z. and Sprent, J. (1994) *J. Exp. Med.* 179: 2005–2015), doses of $5 \times 10^4$ purified CD8+2C lymph node (LN) cells were cultured at 37° C. with doses of $3 \times 10^5$ transfected fly cells±peptides (10 μM final concentration). Peptides were synthesized by R. W. Johnson Pharmaceutical Research Institute (Sykulev, et al. (1994) *Immunity* 1: 15–22. Proliferative responses were measured by adding $^3$HTdR (1 μCi/well) 8 hours prior to harvest. IL-2 production was measured by removing supernatants from the cultures at 48 hours and adding 50 μl supernatant to an IL-2 responsive indicator cell line (CTLL); proliferation of the indicator line was measured by addition of $^3$HTdR. The data shown in Table 2 are the means of triplicate cultures. The transfected Drosophila S2 cells die rapidly at 37° C. and fail to incorporate $^3$HTdR at this temperature.

The data in Table 2 demonstrate that the transfectants are able to stimulate primary responses of mouse T-cells.

Table 2. Capacity of transfected fly cells to stimulate primary proliferative responses and IL-2 production by CD8+lymph node cells from 2C T-cell receptor transgenic mice.

TABLE 2

$^3$HTdR incorporation (cpm x $10^3$) with transfected fly cells expressing:

| Assay | Peptides added | $L^d$ | $L^d$ + B7.1 | $L^d$ + ICAM-1 | $L^d$ + B7.1 + ICAM-1 | $L^d$ + B7.1 combined with $L^d$ + ICAM-1 |
|---|---|---|---|---|---|---|
| Proliferation | — | 0.2 | 0.1 | 0.3 | 0.2 | — |
| (Day 3) | p2Ca | 0.2 | 0.3 | 1.5 | 142.0 | 1.5 |
| | QL9 | 0.2 | 60.9 | 73.9 | 263.7 | 132.9 |
| IL-2 | — | 0.3 | 0.2 | 0.1 | 1.2 | — |
| Production | p2Ca | 0.2 | 0.2 | 0.1 | 64.6 | 0.3 |
| (Day 2) | QL9 | 0.1 | 0.4 | 0.2 | 158.6 | 0.5 |

The 2C T-cell receptor (TCR) is strongly reactive to $L^d$ molecules complexed with certain peptides, e.g. p2Ca or QL9. These two peptides have moderate to high affinity for soluble $L^d$ molecules, $4 \times 10^6$ $M^{-1}$ for p2Ca, and $4 \times 10^9$ $M^{-1}$ for QL9 (Sykulev. et al.). When complexed to soluble $L^d$ molecules, the two peptides also have high binding affinity for soluble 2C TCR molecules. However, in both TCR binding and $L^d$ binding, the QL9 peptide clearly has a higher affinity than the p2Ca peptide.

Table 2 shows that proliferative responses and IL-2 production by the responder 2C cells to the weaker peptide, p2Ca, requires that the stimulator $L^d$-transfected cells coexpress both B7.1 and ICAM-1; a mixture of cells expressing either $L^d$+B7.1 or $L^d$ +ICAM-1 is nonstimulatory. By contrast, with the stronger peptide, QL9, $L^d$.fly cells expressing either B7 or ICAM elicit clearly-significant responses, although combined expression of B7 and ICAM generates much higher responses. In contrast to these findings on T-cell proliferation, IL-2 production in response to the QL9 peptide requires joint expression of B7 and ICAM; expression of these molecules on separate cells is ineffective.

The results show that Drosophila cells transfected with murine class I molecules and costimulatory molecules induce murine T-cells to mount primary proliferative responses and lymphokine (IL-2) production in response to peptide antigens. The system is also applicable to human T-cells and could be used to stimulate unprimed (or primed) T-cells specific for tumor-specific antigens in vitro; in vivo infusion of clonally-expanded T-cells specific for tumor-specific antigens might be therapeutic for patients with cancer. Infusion of T-cells specific for viral antigens would be useful in patients with viral infections, e.g. HIV.

Example 4
Immobilization of Biotinylated MHC Molecules on Avidin-Coated Red Blood Cells NHS-LC-biotin, neutravidin and biotin-BMCC were purchased from Pierce (Rockford, Ill.). Sheep red blood cells were obtained from the Colorado Serum Company (Denver, Colo.). Drosophila S2 cells expressing $L^d$ and recombinant $L^d$ were prepared as described in Examples 1 and 2. Monoclonal antibodies 30.5.7 (anti-$L^d$) and 1B2 (anti-clonotypic antibody to the 2C T cell receptor) were used as hybridoma cell culture supernatants.

The protocol used is described by Muzykantov and Taylor (Anal. Biochem. (1994) 223, 142–148). Briefly, SREC were washed 4 times in phosphate buffered saline (PBS), biotinylated using NHS-LC-biotin, washed again 4 times in PBS, incubated with neutavidin, and finally washed 4 times and stored at 4° C. in PBS containing 3% fetal calf serum and 0.02% sodium azide.

Recombinant $L^d$ was biotinylated using biotin-BMCC, a maleimide-coupled biotin which reacts with thiol groups. $L^d$ displays a free thiol group, the side chain of cystein 121, which is not in the peptide binding site. Biotinylation was performed as recommended by the manufacturer. Unreacted biotin was removed using Centricon 10.

Biotinylated $L^d$ was immobilized by incubation at a final concentration of 0.2 mg/ml with avidin-coated SRBC for 30 minutes followed by washing in DMEM containing 10% fetal calf serum. SRBC with attached $L^d$ were used immediately.

T-cells expressing the 2C TCR transgene from lymph nodes of mice were purified by magnetic depletion. Purified T-cells were consistently 97–98% positive for staining in flow cytofluorometry using the anti-clonotypic antibody 1B2.

Immobilization of biotinylated $L^d$ on avidin-coated SRBC was done as indicated above. Attachment was assessed using flow cytofluorometry using anti-$L^d$ antibody 30.5.7.

Figure 8:
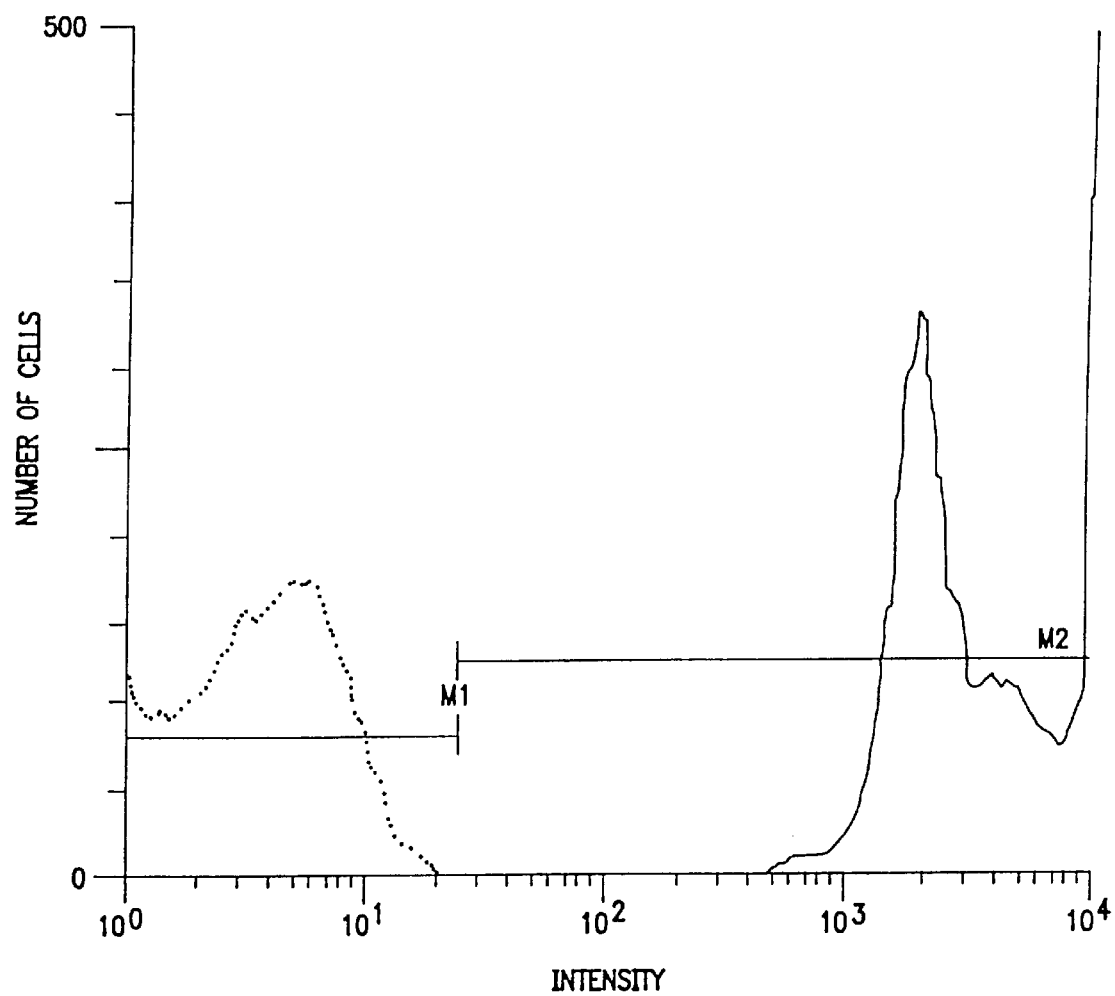
FIG. 8 is a graph showing results of a fluorescence-activated cell sorter experiment using recombinant $L^d$ mouse MHC linked to red blood cells.

A typical experiment is represented in FIG. 8. The negative control (cells minus antibody) is shown in dotted lines. The filled peak comprises cells labeled with fluorescent antibody. 99.78% of the cells were labeled. Fluorescence intensity was in the same range than the highest levels of intensity that we observed for $L^d$ on synthetic antigen presenting cells.

Figure 9:
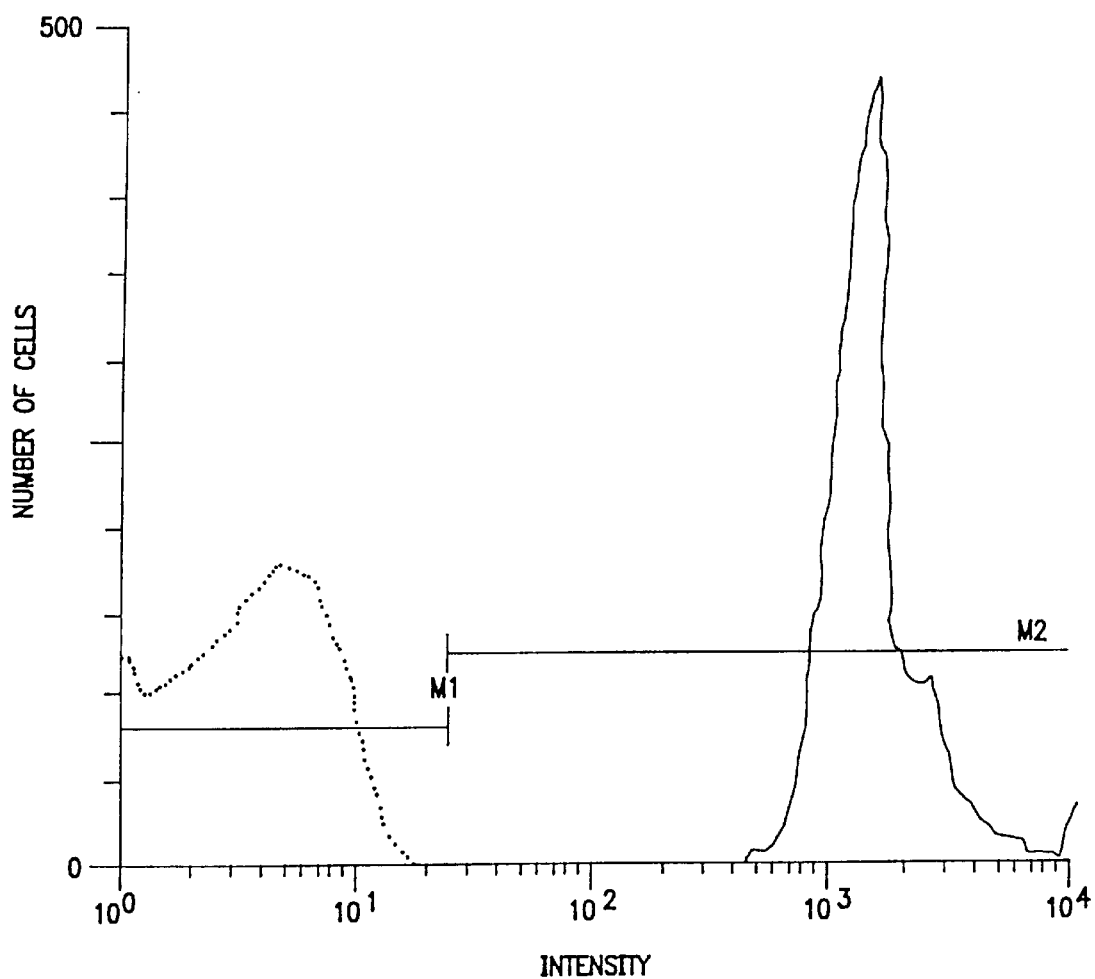
FIG. 9 is a graph showing results of a fluorescence-activated cell sorter experiment using recombinant $K^b$ mouse MHC linked to red blood cells.

$K^b$ was also biotinylated using the same procedure. We could immobilize biotinylated $K^b$ on avidin-coated SRBC as assessed by flow cytofluorometry (FIG. 9). 99.88% of the cells were labeled.

Rosetting experiments verified that the attached MHC molecules interacted functionally with T-cells. Drosophila S2 cells expressing $L^d$, $L^d$-coated SRBC were incubated with QL9 peptide (0.02 mM) or an irrelevant peptide (MCMV, 0.02 mM) for 30 min on ice; 2C+T cells were then added, the proportion being 10 2C+T cells for 1 Drosophila S2 cell, or 10 SRBC for 1 2C+T cell; the mixture was pelleted and kept on ice for at least 30 min. Cells were then carefully resuspended and rosettes were counted, a rosette being a Drosophila S2 cell bound to at least 3 2C+T cells, or a 2C+T cell bound to at least 3 SRBC. Rosettes were observed in all cases. Typically, 30–40% of the lymphocytes were included in rosettes when QL9 peptide was added. No rosette was observed in the presence of the irrelevant peptide, although occasional attachment of a few single cells was observed.

These examples describe a new method to immobilize high amounts of MHC class I molecules on various surfaces (fly cells, red blood cells, latex beads) in native conformation as judged by monoclonal antibody binding and resetting experiments (T cell receptor binding). This method can be extended to other synthetic surfaces including artificial phospholipid membranes. Phosphatidylethanolamine as well as avidin-coupled phospholipids are particularly relevant to our studies. These phospholipids are commercially available from Lipex Biomembrane Inc., Vancouver, BC, Canada.

Example 5
Immobilization of Biotinylated MHC Molecules on Avidin-Coated Latex Beads Six micron diameter latex sulfate beads were purchased from Interfacial Dynamics Corporation (Portland, Oreg.) and biotinylated according to the protocol described in Example 4.

Avidin-coated latex beads were prepared using a 1% suspension of the latex beads incubated in PBS containing lmg/ml of neutravidin for one hour at room temperature. An equal volume of PBS containing 10% fetal calf serum was then added. After one hour of incubation at room temperature, the beads were washed 3 times and used for binding of recombinant biotinylated $L^d$.

Recombinant biotinylated $L^d$ was immobilized by incubation at a final concentration of 0.2 mg/ml with avidin-coated latex beads for 30 minutes followed by washing in DMEM containing 10% fetal calf serum. SRBC with attached $L^d$ were used immediately.

Rosetting experiments verified that the attached MHC molecules on latex beads interacted functionally with T-cells. Drosophila S2 cells expressing recombinant $L^d$ and $L^d$-coated latex beads were incubated with QL9 peptide (0.02 mM) or an irrelevant peptide (MCMV, 0.02 mM) for 30 min on ice; 2C+T cells were then added, the proportion being 10 2C+T cells for 1 Drosophila S2 cell, or $L^d$-coated latex beads for 1 2C+T cell; the mixture was pelleted and kept on ice for at least 30 min. Cells were then carefully resuspended and rosettes were counted, a rosette being a Drosophila S2 cell bound to at least 3 2C+T cells, or a 2C+T cell bound to at least 3 latex beads. Rosettes were observed in all cases. Typically, 30–40% of the lymphocytes were included in rosettes when QL9 peptide was added. No rosette was observed in the presence of the irrelevant peptide, although occasional attachment of a few single cells was observed.

Example 6
Immobilization and Detection of Recombinant Protein Bound to Various Solid SupDorts Such as Plastic Microwell Plates The MHC molecules were immobilized by direct binding to microtiter plates (Corning) and detected as follows:

$K^b$ was diluted to desired concentration in PBS, e.g. 0.001 mg/ml for 100 ng /well. 100 $\mu$l of diluted $K^b$ was added to each well on the plastic microtiter plate. The plate was incubated for 1 hour at room temperature. After incubation, the plate was washed once with PBS and 200 $\mu$l 2% bovine serum albumin (BSA) in PBS+(0.05%) and Tween (PBST) was added, and incubated for another hour at room temperature. The plate was washed three times with PBST and biotinylated anti-$K^b$ mAb was added (1:2500) in 2% BSA in PBS. The plate was incubated another hour at room temperature and washed three times with PBST. Avidin conjugated HRP was added (1:2500) in 2% BSA in PBS. Following another hour of incubation at room temperature, the plate was washed three times with PBST and $H_2O_2$ or thophenyldiamine was added. The reaction was stopped with $H_2SO_4$. Reaction product was detected colorimetrically at 490 nm.

Figure 10:
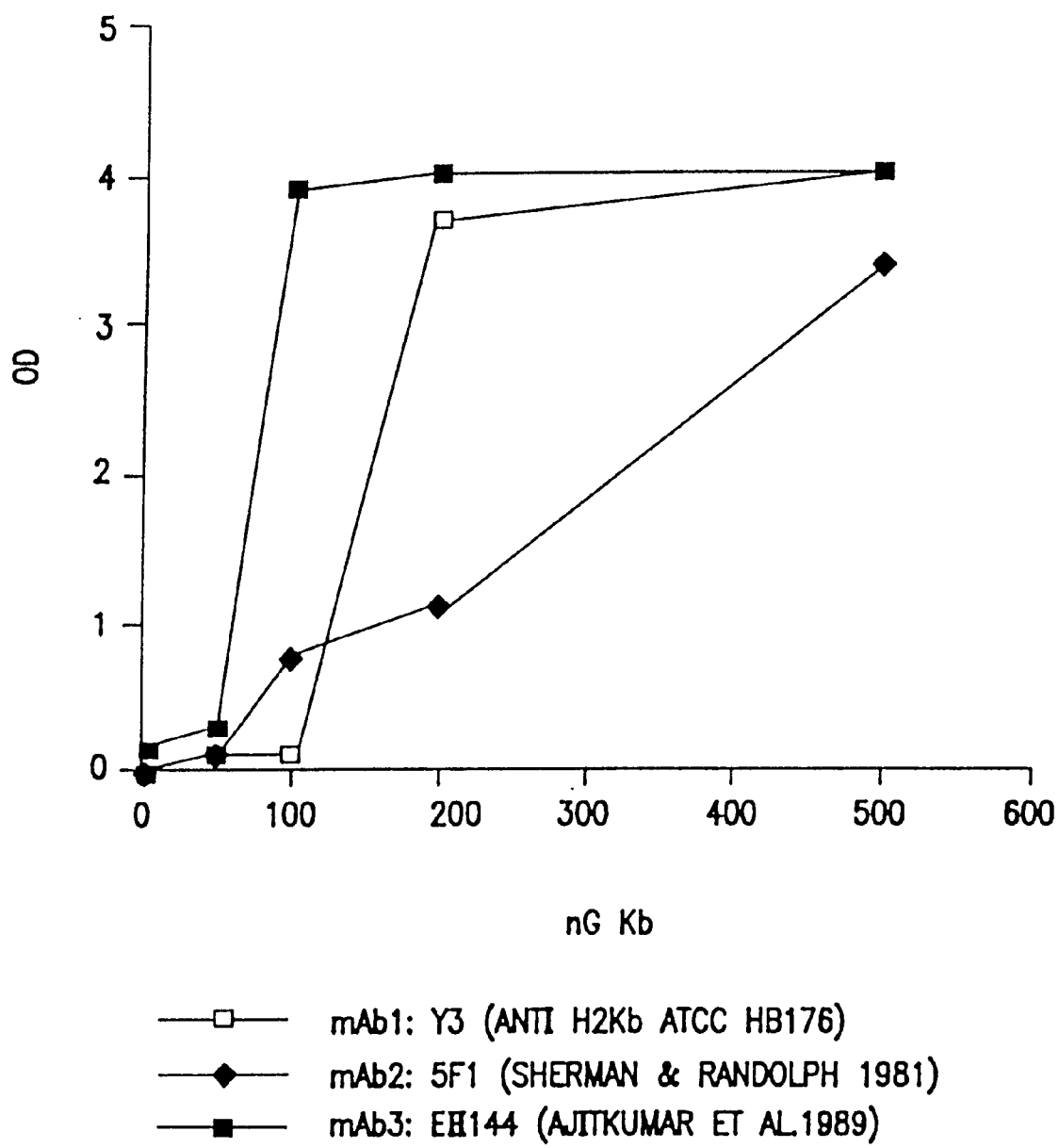
FIG. 10 is a graph demonstrates binding of recombinant $K^b$ to microtiter plates by use of labeled antibodies.

FIG. 10 shows the results of detecting the presence of MHC $K^b$ molecules using three different monoclonal antibodies.

Recombinant MHC $K^b$ molecules can alternatively be bound through biotin-avidin linked interactions with the substrate. In this embodiment, the microwell plates were coated with 100 $\mu$l avidin diluted in PBS to a concentration of 0.001 mg/ml. Excess avidin was removed by a PBS wash. The above procedure for presenting and detecting $K^b$ binding followed.

Recombinant MHC molecules may alternatively be immobilized by a linkage based on a poly-histidine tag added to the MHC interacting with the nickel bound to the substrate.

The above procedure for binding and detection is followed using nickel chelate coated microwell plates (Xenopore) and recombinant MHC molecules with a poly-histidine tag expressed using vector pRmHa/His$_6$ described above.

Example 7
Direct Binding of Peptide to Soluble, Empty Class I MHC Molecules In Vitro A. Procedures H-2$K^b$: prepared as described above in Example 1.B.

H-2$K^b$ Sol: $K^b$ sol cDNA is a derivative of $K^b$, encoding the extracellular portion of the Class I MHC molecule. $K^b$ sol cDNA may be produced by PCR according to known methods, such as those described in Ennis, et al., *PNAS USA* 87: 2833–7 (1990) and Zemmour, et al., *Immunogenetics* 33: 310–20 (1991). Specifically, cDNA encoding a truncated Kb molecule with a stop codon inserted at the end of the alpha 3 domain at amino acid position +275 is excised from the pCMU expression plasmid as a Bam HI fragment and cloned into pRmHa-3 as $K^b$ cDNA. The $K^b$ sol cDNA is a derivative of the complete $K^b$ cDNA (see above) which is used as a template in a PCR reaction using a 5' oligonucleotide that encompassed the Sty I site, and the following 3' oligonucleotide:

5' ATATGGATCCTCACCATCTCAGGGTGAGGGGC 3' (SEQ ID NO 43)

The resulting PCR fragment is blunt-end cloned into the Sma I site of pBS (Stratagene, La Jolla, Calif.), sequenced, and the remaining 5' sequence of $K^b$ cloned into the Sty I site. A cDNA encoding the complete $K^b$sol protein could be obtained as a Bam HI restriction fragment.

H-2$D^b$ and H-2$L^d$ are prepared as discussed in Example 1.B. above.

The cDNAs encoding $K^b$ $\alpha 1 \alpha 2 \alpha 3$ domains (274 residues) and murine $\beta$-2 microglobulin (99 residues) were respectively cloned into the unique Bam HI site of an expression vector harboring the metallothionein promoter pRMHa-3 (Bunch, et al., *Nucleic Acid Res.* 16: 1043–1061 (1988)). Drosophila S2/M3 cells were transformed with these recombinant plasmids in addition to plasmid phshsneo (containing a neomycin-resistance gene) by the calcium-phosphate precipitation method described previously. The transformed cells selected against neomycin-analog antibiotics G418 were grown at 27° C. in serum-free medium and soluble heavy-chain $K^b$ and $\beta$-2 microglobulin were co-expressed by the addition of 0.7 mM $CuSO_4$.

The soluble, assembled heterodimer of $K^b$ was purified from the culture supernatants by affinity chromatography using anti-$K^b$ monoclonal antibody Y3, followed by ion-exchange chromatography on a Pharmacia Mono Q FPLC column according to the instructions of the manufacturer (Pharmacia, Piscataway, N.J.). SDS-polyacrylamide gel electrophoresis (SDS-PAGE) of the $K^b$ preparation followed by staining with Coomassie blue showed only one band of relative molecular mass (Mr) at about 32,000 and one band of Mr at about 12,000 with no detectable impurities. The highly-purified $K^b$ was dialyzed against phosphate-buffered saline (PBS), filter-sterilized, and used for further study. Extinction coefficient of the soluble $K^b$ ("$K^b$sol") protein (43.2 kDa) is 69,200 $M^{-1}$ $cm^{-1}$ at 280 nm.

The purified $K^b$ sol (0.3 $\mu M$) in PBS with or without 1% TX-100 were exposed to varying temperatures (i.e., 4°, 23°, 32°, 37°, 42°, and 47° C.) for one hour. The proteins were then immunoprecipitated by incubating with the monoclonal antibody Y3 and protein A sepharose beads (Pharmacia, Piscataway, N.J.) at 4° C. for two hours, respectively. The samples were analyzed by 12.5% SDS-PAGE, followed by staining with Coomassie blue. The two thick bands on the gel are heavy and light chains of antibody Y3. In another procedure, $K^b$sol (0.3 $\mu M$) were incubated with 50 $\mu M$ of peptides in PBS at 23° C. for two hours to allow for $K^b$sol-peptide complex formation. After the addition of 1% TX-100, the samples were exposed to 12° C., 37° C., or 47° C. temperatures for one hour. The complexes were immunoprecipitated and analyzed by SDS-PAGE as described above. In a third procedure, $K^b$sol (2.7 $\mu M$) were incubated with 50 $\mu M$ of OVA-8, VSV-8 or SEV-9 peptides, respectively, at 23° C. for two hours. The samples were applied on a 5% polyacrylamide IEF gel. IEF was run from pH 5–7 and the gel was stained with silver.

Next, VSV-8 peptide was radioiodinated using the chloramine-T method (Hunter, et al., *Nature* 194: 495–6 (1962)) and free $^{125}I$ was removed by $C_{18}$, column (OPC cartridge, Applied Biosystems, Foster City, Calif.). The labelled peptide was further purified by $C_{18}$ reverse-phase HPLC. After elution, the labelled peptide was lyophilized and resuspended in PBS.

The specific activity of $[^{125}I]$VSV-8 (about 250 Ci/mmole) was determined spectrophotometrically by using extinction coefficient of tyrosine at 274 nm (1420 $M^{-1}$ $cm^{-1}$). First, $K^b$sol (0.5 $\mu M$) was mixed with $[^{125}I]$VSV-8 (1.5 nM) and unlabelled VSV-8 (50 nM) at 23° C. for 16 hours to allow for complex formation. A portion of the sample was analyzed by gel filtration (Superose 12, Pharmacia, Piscataway, N.J.) in PBS. After elution, radioactivity contained in each fraction (0.05 ml) was measured. Protein was monitored by absorbance at 280 nm.

In a second procedure, $[^{125}I]$VSV-8 (0.39 nM) was mixed with various concentrations of $K^b$sol in PBS containing 1% bovine serum albumin (BSA). After incubation at 23° C. for 2–16 hours, $K^b$sol-peptide complexes were separated from free peptide by small gel filtration (Bio-Gel P30, BioRad, Richmond, Calif.) in PBS. P30 gel filtration permitted over 95% separation of bound and free peptide within about 5 minutes. Radioactivity of bound and free peptides was measured and the data were analyzed by linear regression. At maximal levels of $K^b$sol offered, about 65% of the total labelled peptides were bound. This maximal binding capacity of labelled peptide to $K^b$sol protein deteriorated over time, presumably due to radiation by $^{125}I$ bound to VSV-8.

In a third procedure, each sample contained 0.39 nM of $[^{125}I]$VSV-8 (about 18,000 cpm), unlabelled peptides at the indicated concentration, and 30 nM of $K^b$sol that gives about 50% of the $[^{125}I]$VSV-8 binding in the absence of unlabelled peptide at a final volume of 72 $\mu l$. All components were dissolved and diluted in PBS containing 1% BSA. After incubation for 2–16 hours at 23° C., 50 $\mu l$ samples were analyzed by P30 gel filtration as described above. The dissociation constants for unlabelled peptides were determined from molar concentrations of $[125I]$VSV-8 and unlabelled peptides giving 50% inhibition of $[^{125}I]$VSV-8 binding to $K^b$sol as described. (See Muller, et al., *Meth. Enzvmol.* 92: 589–601 (1983).)

$K^b$sol (0.3 $\mu M$) and $[^{125}I]$VSV-8 (0.39 nM) were then incubated at 4° C., 23° C., and 37° C., and the association was determined at various times by P30 gel filtration. Murine $\beta$-2 microglobulin was added, when necessary, before the incubation at the indicated concentration. The murine $\beta$-2 microglobulin was prepared by affinity chromatography using anti-$\beta$-2 microglobulin polyclonal antibody K355 from culture supernatants of the recombinant Drosophila cells. (See also Logdberg, et al., *Molec. Immun.* 14: 577–587 (1979).) In another experiment, $K^b$sol (0.3 $\mu M$ or 1.8 $\mu M$) and $[^{125}I]$VSV-8 (2.4 nM) were incubated at 23° C. for two hours, and the peptide-$K^b$sol complexes were isolated by P30 gel filtration. The samples contained very small amounts of $[^{125}I]$VSV-8 and $K^b$sol complexes (at the maximum, 2.4 nM) and empty $K^b$sol at final concentration of about 50 to 300 nM. To some samples, 3$\mu M$ of $\beta$-2 microglobulin, 3 $\mu M$ of $\beta$-2 microglobulin plus 20 $\mu M$ of unlabelled VSV-8, 20 $\mu M$ of unlabelled VSV-8, or 1% TX-100 were added. The samples were incubated for various times at 37° C. and the degree of dissociation was determined by passage over P30 columns.

B. Discussion

Class I MHC molecules present antigenic peptides to cytotoxic T lymphocytes. Direct binding of peptide to Class I molecules in vitro has been hampered by either the presence of previously bound peptides at the binding site (Chen and Perham, *Nature* 337: 743–5 (1989)) or the lack of binding specificity. (See, e.g., Frelinger, et al., *J. Exp. Med.* 172: 827–34 (1990); Choppin, et al., *J. Exp. Med.* 172: 889–99 (1990); Chen, et al., *J. Exp. Med.* 172: 931–6 (1990).) In vitro analysis of peptide binding to soluble, empty Class I molecules purified from Drosophila cells transformed with truncated H-2$K^b$sol and murine $\beta$-2 microglobulin genes is disclosed herein. The results demonstrate that peptide binding is very rapid and naturally processed peptides (octapeptides; see, e.g., Van Bleek, et al., *Nature* 348: 213–6 (1990); Falk, et al., *Nature* 351: 290–6 (1991)) have the highest affinities to $K^b$sol of the nanomolar range and indicate that $K^b$sol complexed with octapeptides are stable, whereas those complexed with slightly shorter or longer peptides are short-lived. Interactions between free heavy chain and $\beta$-2 microglobulin is basically reversible in the absence of detergent. Peptides spontaneously bind to empty Class I molecules without dissolution of $\beta$-2 microglobulin. However, excess $\beta$-2 microglobulin apparently promotes the binding of peptide to empty Class I as a consequence of reassociation of free heavy chain with β-2 microglobulin under conditions where the heterodimers are unstable.

Soluble H-2K$^b$ molecules (composed of the α1α2α3 domain of heavy chain) and murine β-2 microglobulin, were purified from the culture supernatants of Drosophila cells which were concomitantly transformed with the truncated heavy chain and β-2 microglobulin genes. Preliminary examinations suggested that Drosophila cells express Class I MHC molecules devoid of endogenous peptides on the cell surface. Some of the properties of empty Class I molecules include the observation that they are less stable at 37° C. and their structure is stabilized by the binding of peptide. (See, e.g., Schumacher, et al., *Cell* 62: 563–7 (1990); Ljunggren, et al., *Nature* 346: 476–80 (1990).) To confirm that purified soluble K$^b$ are also empty, their thermal stability in detergent-free solution was examined. Surprisingly, the proteins heated for one hour at 47° C. were well recovered by immunoprecipitation using a conformational antibody, Y3. This unexpected result led us to add detergent, 1% Triton X-100 (polyoxyethylene (9) octyl phenyl ether), to the protein solution, since similar experiments to test the stability of Class I molecules have always been conducted in detergent lysates (See Schumacher, et al., cited supra). The results obtained in the presence of detergent show that the purified K$^b$sol is now unstable at 37° C. This and other lines of evidence suggest that K$^b$sol heterodimer disassembles into the heavy chain and β-2 microglobulin at elevated temperatures and that detergent may prevent β-2 microglobulin from reassociating with dissociated free heavy chain (see below). Second, the possibility of stabilizing purified K$^b$sol with peptides was studied. The results of the first-described examination demonstrated that the proteins can be stabilized only when they are mixed with octapeptide (vesicular stomatitis virus nucleocapsid protein [VSV-8], see Table 3 below) which is shown to be a naturally processed peptide (see Van Bleek, et al., cited supra). These observations are consistent with the characteristics of empty Class I molecules mentioned above.

Independent support that the purified K$^b$sol molecules are empty is provided by isoelectric focusing (IEF) under native conditions (data not shown). The soluble K$^b$ purified from Drosophila cells exhibited a much simpler pattern than HLA-A2 molecules purified from human lymphoblastoid cell lines (see FIG. 3 in Silver, et al., *Nature* 350: 619–22 (1991)). The complicated pattern of HLA-A2 on IEF is presumed to be the result of the presence of heterogeneous peptides bound to the molecules. The simple band of purified K$^b$sol indicates the absence of endogenous peptides. In addition, the incubation of K$^b$sol with antigenic peptides caused the distinct shifts of band on IEF gel, reflecting the change in isoelectric point of K$^b$sol due to the peptide binding. It should be noted that such band-shifting was not observed in HLA-A2 molecules when they were simply mixed with peptides, unless HLA-A2 are incubated with peptides in "reconstituting conditions" after removal of previously bound endogenous peptides. Taken together, these observations on native IEF also indicate that soluble K$^b$ purified from Drosophila cells are empty.

The association of $^{125}$I-labelled VSV-8 with K$^b$sol was demonstrated by gel filtration (not shown). The radioactivity of high molecular weight materials corresponds to peptide-K$^b$sol complexes, while that of low molecular weight materials represents free peptides. Unlabelled VSV and ovalbumin (OVA) peptides could compete with the labelled VSV-8 (see below), arguing that [$^{125}$I]VSV-8 is bound specifically to K$^b$sol molecules. Reversed-phase HPLC revealed that K$^b$-bound [$^{125}$I]VSV-8 has the identical retention time to the input peptide. The binding to K$^b$sol of the labelled VSV-8 was saturable, exhibiting a dissociation constant ($K_D$) of about 33 nM (not shown). From the x-axis of the Scatchard plot, it was noted that about 65% of the labelled VSV-8 is able to bind to K$^b$.

To determine affinities of various peptides to K$^b$, competitive radioimmunoassays (RIA) using [$^{125}$I]VSV-8 were carried out (data not shown). The inhibitory peptides used for the RIA are listed in Table 3. $K_D$ for each peptide is summarized in Table 3 as well.

TABLE 3

Various Antigenic Peptides* Used in Present Studies

| Code | Sequence | $K_D$ (M) |
| --- | --- | --- |
| VSV-7 | GYVYQGL | $5.3 \times 10^{-8}$ |
| VSV-8 | RGYVYQGL | $3.7 \times 10^{-9}$ |
| VSV-9N | LRGYVYQGL | $7.3 \times 10^{-9}$ |
| VSV-10N | DLRGYVYQGL | $3.9 \times 10^{-7}$ |
| VSV-9C | RGYVYQGLK | $6.9 \times 10^{-9}$ |
| VSV-10C | RGYVYQGLKS | $2.1 \times 10^{-8}$ |
| OVA-8 | SIINFEKL | $4.1 \times 10^{-9}$ |
| OVA-9N | ESIINFEKL | $8.9 \times 10^{-8}$ |
| CVA-10N | LESIINFEKL | $2.8 \times 10^{-7}$ |
| CVA-9C | SIINFEKLT | $1.1 \times 10^{-8}$ |
| CVA-10C | SIINFEKLTE | $1.4 \times 10^{-8}$ |
| CVA-24 | EQLESIINFEKLTEWTSSNVMEER | $7.1 \times 10^{-5}$ |
| SEV-9 | FAPGNYPAL | $2.7 \times 10^{-9}$ |

TABLE 3-continued

Various Antigenic Peptides* Used in Present Studies

VSV-8: Vesicular stomatitis virus nucleocapsid protein 52–59 (Van Bleek, et al., Nature 348: 213–216 (1990))
OVA-8: Ovalbumin 257–264 (Carbone, et al., J. Exp. Med. 169: 603–12 (1989));
SEV-9: Sendai virus nucleoprotein 324–332 (Schumacher, et al., Nature 350: 703–706 (1991))
*All peptides were purified by $C_{18}$ reversed-phase HPLC to exclude contaminating shorter peptides with different binding properties. The 3-letter code designations and SEQ ID NO for each peptide are given below.

| | | |
|---|---|---|
| VSV-7 | GlyTyrValTyrGlnGlyLeu | (SEQ ID NO 40, residue nos. 4–10) |
| VSV-8 | ArgGlyTyrValTyrGlnGlyLeu | (SEQ ID NO 40, residue nos. 3–10) |
| VSV-9N | LeuArgGlyTyrValTyrGlnGlyLeu | (SEQ ID NO 40, residue nos. 2–10) |
| VSV-10N | AspLeuArgGlyTyrValTyrGlnGlyLeu | (SEQ ID NO 40) |
| VSV-9C | ArgGlyTyrValTyrGlnGlyLeuLys | (SEQ ID NO 44, residue nos. 1–9) |
| VSV-10C | ArgGlyTyrValTyrGlnGlyLeuLysSer | (SEQ ID NO 44) |
| OVA-8 | SerIleIleAsnPheGluLysLeu | (SEQ ID NO 39, residue nos. 5–12) |
| OVA-9N | GluSerIleIleAsnPheGluLysLeu | (SEQ ID NO 39, residue nos. 4–12) |
| OVA-10N | LeuGluSerIleIleAsnPheGluLysLeu | (SEQ ID NO 39, residue nos. 3–12) |
| OVA-9C | SerIleIleAsnPheGluLysLeuThr | (SEQ ID NC 39, residue nos. 5–13) |
| OVA-10C | SerIleIleAsnPheGluLysLeuThrGlu | (SEQ ID NO 39, residue nos. 5–14) |
| OVA-24 | GluGlnLeuGluSerIleIleAsnPheGluLysLeuThrGlu-TrpThrSerSerAsnValMetGluGluArg | (SEQ ID NO 39) |
| SEV-9 | PheAlaProGlyAsnTyrPraAlaLeu | (SEQ ID NO 45) |

The peptides of naturally processed size (8 mer for VSV and OVA, and 9 mer for sendai virus nucleoprotein [SEV]) had the highest and remarkably similar affinities from the range of 2.7 to 4.1 nM. this exceedingly high affinity of the natural peptides is consistent with recent observations. (See, e.g., Schumacher, et al., *Nature* 350: 703–6 (1991); Christnick, et al., *Nature* 352: 67–70 (1991).) However, peptides that were shorter or longer by as little as one or two residues lowered the affinity by a factor of from 2 to 100. This reduction of the affinity is even more drastic for a much longer peptide; i.e., the affinity of 24 mer peptide (OVA-24) is more than 10,000-fold lower than that of OVA-8. These results help to explain why earlier reports using longer peptides claim the affinity of micromolar range. (See, e.g., Frelinger, et al. and Choppin, et al., both cited supra.) It is of particular interest that the extension of peptides at the carboxyl terminus is much less destructive of the affinity than extension at the amino terminus. According to the three-dimensional structure of HLA-A2, the peptide-binding groove is formed by two long $\alpha$ helices on the antiparallel $\beta$ strands, and the cleft is about 25 angstroms long, which is proposed to accommodate an extended peptide chain of about eight residues (see, e.g., Bjorkman, et al., *Nature* 329: 506–12 (1987)). At one end of the cleft, the $\alpha 1$ and $\alpha 2$ helices come close together tightly, while at the other end, the cleft is fairly open. It is now speculated that both VSV and OVA peptide bind to the cleft in the same orientation *and the carboxyl terminus of the peptides might interact ith the relatively open end of the cleft so that the extension of peptide at the carboxyl terminus does not cause severe steric hindrance.

Examinations were then performed to determine the rate of peptide binding to $K^b$ at 4° C. and 23° C., respectively (not shown). Binding was very rapid, especially at 23° C., with a half-time of about 5 minutes even in extremely low concentrations of labelled peptides (about 0.4 nM). This contrasts with previous observations, which show a half-time of association of about two hours. (See, e.g., Choppin, et al., cited supra.) Again, only 65% of the total labelled peptide was able to bind. The addition of excess $\beta$-2 microglobulin did not affect the peptide-binding kinetics at such low temperatures that $K^b$ heterodimer is stable (remained to be assembled). This implies that exchange of $\beta$-2 microglobulin is not a prerequisite for peptide binding; i.e., peptides can spontaneously bind to empty Class I molecules without dissociation of $\beta$-2 microglobulin. In contrast, excess free $\beta$-2 microglobulin apparently promotes peptide binding at 37° C. (data not shown). As the concentration of added $\beta$-2 microglobulin increased, more peptides bound to $K^b$ molecules. Since empty $K^b$ are unstable at 37° C., a fraction of heterodimers must be dissociated to the heavy chain and β-2 microglobulin and thereby, the heterodimer must be in equilibrium with free heavy chain and free β-2 microglobulin. Then, the addition of β-2 microglobulin should shift the equilibrium toward the formation of heterodimer that can bind peptides. This view is supported by recent observations that there are substantial numbers of Class I free heavy chains on the normal cell surface and exogenously added β-2 microglobulin facilitates peptide binding to empty Class I molecules on cells as a consequence of the reassociation of β-2 microglobulin with free heavy chain. (See, e.g., Rock, et al., *Cell* 65: 611–620 (1991); Kozlowski, et al., *Nature* 349: 74–77 (1991); Vitiello, et al., *Science* 250: 1423–6 (1990).)

The dissociation kinetics of peptide at 37° C. were then observed. Immediately after isolating [$^{125}$I]VSV-8 and $K^b$ complexes by gel filtration, the samples containing either 50 or 300 nM $K^b$ were exposed to 37° C. temperatures. Some samples were supplemented with 3 μM β-2 microglobulin and/or 20 μM unlabelled VSV-8, or 1% TX-100. The dissociation of labelled peptides from $K^b$ was measured at various times (not shown). In the presence of a large excess of unlabelled peptides, the dissociation rate of peptide followed first-order kinetics with a half-time dissociation of about 36 minutes (a dissociation rate constant of $3.2 \times 10^{-4}$ $S^{-1}$). This unexpected, relatively rapid dissociation of labelled peptide does not agree with some current views of stable peptide-Class I complexes. In fact, the results ascertained (not shown) demonstrated that $K^b$ and VSV-8 complexes are stable. This discrepancy must arise from the 10-fold lower affinity of radiolabelled VSV-8 (33 nM) compared with that of unlabelled VSV-8 (3.7 nM).

The first-order kinetics were also observed when the detergent was added instead of unlabelled peptide, indicating that the detergent makes the peptide dissociation process irreversible. In contrast, the peptide dissociation profile did not follow the first-order kinetics in the absence of unlabelled peptide or the detergent. This suggests that the peptide association/dissociation is reversible and the binding of peptide is dependent on the concentration of heterodimer (compare the kinetics between 50 nM and 300 nM of $K^b$). This became more evident when excess β-2 microglobulin was added. These results support the previous argument that interaction between the heavy chain, β-2 microglobulin and peptide are basically reversible at 37° C., if not entirely, in the absence of detergent. It is probable that a detergent such as TX-100 may prevent β-2 microglobulin from reassociating with free heavy chain at 37° C. This could reasonably explain why $K^b$ once heated to elevated temperatures in the absence of detergent can be efficiently immunoprecipitated by conformational antibody (not shown). Interestingly, the addition of β-2 microglobulin did not suppress the peptide dissociation in the presence of excess unlabelled peptides, indicating that labelled peptides are released from the complexes without dissociation of β-2 microglobulin. It should be remembered, however, that the affinity of [$^{125}$I]VSV-8 is about 10-fold lower than that of the natural peptides. Therefore, this is not necessarily the case for the natural peptides.

The study using in vitro peptide-binding assay systems suggests that peptide binding to Class I molecules is a simple mass action-and a ligand-receptor interaction. The approach used herein allows characterization of the peptide binding specificity to Class I molecules and of the interaction of peptide-Class I complexes with the T-cell receptor.

Example 8

Therapeutic Applications

A. Class I Molecule Bank

A reservoir or "bank" of insect cell lines may be established and maintained, with each cell line expressing one of the 50 to 100 most common Class I MHC heavy chain, a β-microglobulin molecule, as well as at least one assisting molecule. cDNAs encoding these proteins may be cloned based on HLA variants obtained from cell lines containing same—e.g., via the olymerase chain reaction (see Ennis, et al., *PNAS USA* 7: 2833–7 (1990))—and inserted into the appropriate vector, such as an insect expression vector, to generate ell lines expressing each HLA variant.

Testing according to the following protocol, or example, can be used to determine which peptides derived from the virus of choice bind the best to the different Class I MHC molecules. The various cultures may appropriately be labeled or catalogued to indicate which Class I MHC molecules are best for use with particular peptides. Alternatively, transient cultures may be established as needed. As discussed herein, after approximately 48 hours' incubation of a culture of insect cells with a vector, that culture is apparently capable of expressing empty MHC molecules which may be loaded with the peptide(s) of choice for the purpose of activating CD8 cells.

B. Preparation of "Special" Cell Lines

After HLA typing, if insect cell lines expressing the preferred HLA are not available, cDNAs encoding the preferred HLA and assisting molecules may be cloned via use of the polymerase chain reaction. The primers disclosed in section B.1. above (SEQ ID NO 1 through SEQ ID NO 12) may be used to amplify the appropriate HLA-A, -B, -C, -E, -F, or -G cDNAs in separate reactions which may then be cloned and sequenced as described in the methods disclosed in Example 1, section 1 above. DNA is then purified from the PCR reaction using a Gene Clean kit (Bio 101, San Diego, Calif.) and ligated directly into the Sma I site of pRmHa-3. Individual clones are isolated, the sequences verified, and stable Drosophila cell lines expressing the HLA established. Alternatively, a bulk population of recombinant plasmids may be grown in large scale and DNA purified by cesium chloride gradients. The purified DNA is then used to transfect S2 cells using calcium phosphate precipitation techniques. After 24 hours, the precipitate is washed off the cells and replaced with fresh Schneider media containing 1 mM $CuSO_4$. Forty-eight hours later, the bulk population of transiently transfected cells is used for in vitro activation of CD8 after incubation with syngeneic peptides or protease digests of specific proteins.

Stable cell lines expressing the cloned HLA may then be established. Alternatively, a population of insect cells transiently expressing a bulk population of cloned recombinant molecules from the PCR reaction may be used for in vitro CD8 activation.

It is also possible to activate haplotype-specific CD8s in vitro using insect cells expressing Class I MHC incubated with peptides where the cell line-expressed MHC is not the expressed element in vivo. This provides a unique opportunity to proliferate CD8 cells which recognize a specific antigen associated with a particular MHC which would not be possible in vivo due to allelic restriction. For example, a peptide (NP) from the nuclear protein of Influenza virus is ordinarily restricted to the $D^b$ molecule; however, we have found that such a peptide can bind to $K^b$ (albeit more weakly than to $D^b$) and can generate a degree of thermal stability to the $K^b$ (see FIG. 3). Furthermore, $K^b$-expressing Drosophila cells preincubated with the NP peptide and cocultured with splenocytes from a B6 mouse results in the in vitro activation of CD8 which specifically recognize the $K^b$ molecule associated with the NP peptide. In addition, the reciprocal experiment using a $K^b$-restricted peptide (OVA) derived from ovalbumin and $D^b$-expressing Drosophila cells results in the proliferation of CD8 which specifically recognize Db containing the OVA peptide. Such CD8s are able to kill cells (EL4 OVA) transfected with cNDA encoding the ovalbumin protein, indicating that in viva, some $D^b$ molecules are loaded with the OVA peptide.

This system therefore provides a unique opportunity to proliferate CD8 against specific antigens presented by a Class I molecule which, in vivo, is not the restriction element for that peptide. Although enough antigen is presented in vivo by said Class I for the cell to be recognized by CD8 and killed, it is not enough to proliferate such CD8s in vivo. By loading empty Class I molecules expressed by Drosophila cells with peptide, we are able to override the in viva restriction by providing an excess of antigenic peptide to the Class I molecule in a non-competitive environment such that enough antigen is presented by the Class I to activate the specific CD8 recognizing this complex.

C. AIDS Treatment

In vitro activated cells may be administered to patients for in vivo therapy. Preferably, the Class I MHC genotype (haplotype) of the individual is first determined. Conventional tissue typing is appropriate for this purpose and may be performed at the treatment center or by some appropriate commercial operation. Once the individual's HLA type(s) is (are) determined, the best combination of peptides and Class I MHC molecules suitable for the individual patient is ascertained and prepared as noted above and the appropriate insect cell lines and peptides are provided. Resting or precursor CD8 (T) cells from the blood of the patient are then stimulated with the appropriate peptide-loaded MHC produced by the insect cell culture. After activation, the CD8 cells are reintroduced into the patient's bloodstream, and the disease process in the patient continues to be monitored. Methods of removing and re-introducing cellular components are known in the art and include procedures such as those exemplified in U.S. Pat. No. 4,844,893 to Honsik, et al. and U.S. Pat. No. 4,690,915 to Rosenberg.

Additional treatments may be administered as necessary until the disease is sufficiently remediated. Similar treatment protocols are appropriate for use with other immunosuppressed individuals, including transplant patients, elderly patients, and the like.

D. Cancer Treatment

In cancer patients, a treatment procedure similar to that described above is utilized. However, in such patients, it should be anticipated that conventional therapy to reduce the tumor mass may precede the immune therapy described herein. Therefore, it is preferred that blood samples from the putative patient be obtained and stored (e.g. via freezing) prior to the commencement of conventional therapy such as radiation or chemotherapy, which tends to destroy immune cells. Since few, if any, forms of cancer arise in direct response to viral infection, target peptides for immune treatment are less readily observed. However, recent studies indicate that mutations in the oncogenes ras, neu, and p53 contribute to cancer in as much as 50% of all cancer cases. Thus, peptides derived from these mutated regions of the molecules are prime candidates as targets for the present therapy. Pursuant to the protocols disclosed herein, the best combination of peptides and Class I molecules for the individual patient may be determined and administered.

For example, many tumors express antigens that are recognized in vitro by CD8 cells derived from the affected individual. Such antigens which are not expressed in normal cells may thus be identified, as well as the HLA type that presents them to the CD8 cells, for precisely targeted immunotherapy using the methods of the present invention. For example, van der Bruggen, et al. have described an antigen whose expression is directed by a specific gene and which antigen appears to be presented by HLA A1 (*Science* 254: 1643–1647 (1991)). As various human tumor antigens are isolated and described, they become good candidates for immunotherapeutic applications as described herein.

In another, alternative therapeutic mode, it may be feasible to administer the in vitro activated CD8 cells of the present invention in conjunction with other immunogens. For example, the Large Multivalent Immunogen disclosed in U.S. Pat. No. 5,045,320 may be administered in conjunction with activated CD8 cells.

It is also possible that cytokines such as IL-2 and IL-4, which mediate differentiation and activation of T-cells, may be administered as well, as cytokines are able to stimulate the T-cell response against tumor cells in vivo. It is believed that IL-2 plays a major role in the growth and differentiation of CD8 precursors and in CD8 proliferation. The administration of IL-2 to cancer patients is frequently associated-.with an improved anti-tumor response which is likely related to induction of tumor-specific T-cells. However, the best therapeutic effects of IL-2 might be obtained by continuous local rather than systemic administration of IL-2, thus minimizing the IL-2 toxicity and prolonging its biological activity. One may achieve 'local delivery via transfecting tumor cells with an IL-2 gene construct.

IL-2 cDNA is constructed as described by Karasuyama and Melchers in *Eur. J. Immunol.* 18: 97–104 (1988). The complete cNDA sequence of IL-2 is obtained as an Xho I fragment from the plasmid pBMGneo IL-2 (see Karasuyama and Melchers, supra) and directly ligated into the Sal I site in pRmHa-3. Recombinant pRmHa-3 plasmid with the insert in the correct orientation (determined via restriction mapping with Hind III) is purified by cesium gradients and used to cotransfect S2 cells using the calcium phosphate technique. (A mixture of plasmid DNA was prepared for this purpose: 10 μg pRmHa-3 containing IL-2 cNDA, 6 μg each of pRmHa-3 plasmid containing MHC Class I heavy chain or β-2 microglobulin and 2 μg of phshsneo DNA.) Stable cell lines which are inducible via $CuSO_4$ to express heavy chain, β-2 microglobulin and IL-2 were obtained by growing the transfectants in G418 medium. These stable cell lines were coated with peptide and used in the in vitro assay as described above. Tumor cells transfected with IL-2 are observed to enhance the CTL (CD8) activity against the parental tumor cells and bypass CD4 and T helper function in the induction of an antitumor or cytotoxic response in vivo. Therefore, increasing the potential of the Drosophila system via cotransfection with the IL-2 gene is suggested herein.

The foregoing is intended to be illustrative of the present invention, but not limiting. Numerous variations and modifications may be effected without departing from the true spirit and scope of the invention.

We claim:

1. A method for activating CD8 T-cells against a selected peptide in vitro, the method comprising:
   a) providing a synthetic antigen presenting cell line suitable for use with T-cell lymphocytes and comprising:
      (i) a nucleotide sequence encoding for a Class I MHC heavy chain operably linked to a first promoter expressing a Class I MHC heavy chain;
      (ii) a nucleotide sequence encoding for a β-2 microglobulin operably linked to a second promoter expressing a β-2 microglobulin that with the MHC heavy chain forms an MHC molecule; and
      (iii) a nucleotide sequence encoding for a for an assisting molecule operably linked to a third promoter for expressing a membrane bound assisting molecule that interacts with a molecule on the T-cell lymphocytes, said assisting molecule selected from the group of molecules consisting of B7.1, B7.2, ICAM-1, ICAM-2, ICAM-3, and LFA-3;
      transformed into an insect host cell, such that the MHC class I molecules and assisting molecules are presented on the surface of the cell in sufficient numbers to activate a population of T lymphocytes specific for said peptide when the peptide is bound to the MHC class I molecules;
   b) culturing the cell line under conditions such that MHC class I molecules are produced on the surface of the cell line that are bound to the selected peptide; and
   c) contacting the cultured cells with the CD8 T-cells against the selected peptide.

2. The method of claim 1 wherein the cell line is a poikilotherm.

3. The method of claim 1 further comprising the step of separating the activated CD8 T-cells from the 10 cell line.

4. The method of claim 3 further comprising the step of adding the activated CD8 T-cells to an acceptable carrier or excipient to form a suspension.

5. An in vitro method for activating a plurality of CD8 T-cells against a selected peptide, the method comprising:
  (i) providing a syntbetic antigen-presenting matrix comprising:
    a) a support comprising a fragment of an insect host cell;
    b) an extracellular portion of a Class I MHC molecule linked to the support, the Class I MHC molecule being produced by said insect host cell and comprising a heavy chain and a β-2 microglobulin;
    c) a selected peptide bound to said extracellular portion of the Class I MHC molecule; and
    d) an extracellular portion of an assisting molecule produced by expression in said insect host cell and operably linked to the support, selected from the group consisting of B7.1, B7.2, ICAM-1, ICAM-2, ICAM-3, and LFA-3; and
  (ii) contacting the CD8 T-cells to be activated with the matrix.

* * * * *

UNITED STATES PATENT AND TRADEMARK OFFICE
CERTIFICATE OF CORRECTION

PATENT NO. : 6,225,042 B1
DATED : May 1, 2001
INVENTOR(S) : Zeling Cai et al.

It is certified that error appears in the above-identified patent and that said Letters Patent is hereby corrected as shown below:

Columns 41-42,
TABLE 3, under the heading "Code":
Line 9, "CVA-10N" should be -- OVA-10N --.
Line 10, "CVA-9C" should be -- OVA-9C --.
Line 11, "CVA-10C" should be -- OVA-10C --.
Line 12, "CVA-24" should be -- OVA-24 --.

Columns 43-44,
TABLE 3-continued, last line, "PheAlaProGlyAsnTyrPraAlaLeu" should be
-- PheAlaProGlyAsnTyrProAlaLeu --.

Column 46,
Line 11, "7: 2833-7" should be -- 87: 2833-7 --.
Line 13, "ell" should be -- cell --.

Column 48,
Lines 28-29, "associated-.with" should be -- associated with --.
Line 34, before "local" delete the apostrophe (').

Column 99,
Line 4, delete "10".

Signed and Sealed this

Fourteenth Day of January, 2003

JAMES E. ROGAN
*Director of the United States Patent and Trademark Office*

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

CCACCATGGC CGTCATGGCG CCC                                 23

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

GGTCACACTT TACAAGCTCT GAG                                 23

(2) INFORMATION FOR SEQ ID NO:3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

CCACCATGCT GGTCATGGCG CCC                                 23

(2) INFORMATION FOR SEQ ID NO:4:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GGACTCGATG TGAGAGACAC ATC                                              23

(2) INFORMATION FOR SEQ ID NO:5:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CCACCATGCG GGTCATGGCG CCC                                              23

(2) INFORMATION FOR SEQ ID NO:6:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GGTCAGGCTT TACAAGCGAT GAG                                              23

(2) INFORMATION FOR SEQ ID NO:7:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

CCACCATGCG GGTAGATGCC CTC                                              23

(2) INFORMATION FOR SEQ ID NO:8:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GGTTACAAGC TGTGAGACTC AGA                                              23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CCACCATGGC GCCCCGAAGC CTC                                  23

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GGTCACACTT TATTAGCTGT GAG                                  23

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

CCACCATGGC GCCCCGAACC CTC                                  23

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

GGTCACAATT TACAAGCCGA GAG                                  23

(2) INFORMATION FOR SEQ ID NO:13:

(i) SEQUENCE CHARACTERISTICS:
    (A) LENGTH: 427 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

```
AATTCGTTGC AGGACAGGAT GTGGTGCCCG ATGTGACTAG CTCTTTGCTG CAGGCCGTCC        60
TATCCTCTGG TTCCGATAAG AGACCCAGAA CTCCGGCCCC CCACCGCCCA CCGCCACCCC       120
CATACATATG TGGTACGCAA GTAAGAGTGC CTGCGCATGC CCCATGTGCC CCACCAAGAG       180
TTTTGCATCC CATACAAGTC CCCAAAGTGG AGAACCGAAC CAATTCTTCG CGGGCAGAAC       240
AAAAGCTTCT GCACACGTCT CCACTCGAAT TTGGAGCCGG CCGGCGTGTG CAAAAGAGGT       300
GAATCGAACG AAAGACCCGT GTGTAAAGCC GCGTTTCCAA AATGTATAAA ACCGAGAGCA       360
TCTGGCCAAT GTGCATCAGT TGTGGTCAGC AGCAAAATCA AGTGAATCAT CTCAGTGCAA       420
CTAAAGG                                                                 427
```

(2) INFORMATION FOR SEQ ID NO:14:

(i) SEQUENCE CHARACTERISTICS:
        (A) LENGTH: 740 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

```
ATTCGATGCA CACTCACATT CTTCTCCTAA TACGATAATA AAACTTTCCA TGAAAAATAT        60
GGAAAAATAT ATGAAAATTG AGAAATCCAA AAAACTGATA AACGCTCTAC TTAATTAAAA       120
TAGATAAATG GGAGCGGCTG GAATGGCGGA GCATGACCAA GTTCCTCCGC CAATCAGTCG       180
TAAAACAGAA GTCGTGGAAA GCGGATAGAA AGAATGTTCG ATTTGACGGG CAAGCATGTC       240
TGCTATGTGG CGGATTGCGG AGGAATTGCA CTGGAGACCA GCAAGGTTCT CATGACCAAG       300
AATATAGCGG TGTGAGTGAG CGGGAAGCTC GGTTTCTGTC CAGATCGAAC TCAAAACTAG       360
TCCAGCCAGT CGCTGTCGAA ACTAATTAAG TTAATGAGTT TTTCATGTTA GTTTCGCGCT       420
GAGCAACAAT TAAGTTTATG TTTCAGTTCG GCTTAGATTT CGCTGAAGGA CTTGCCACTT       480
TCAATCAATA CTTTAGAACA AAATCAAAAC TCATTCTAAT AGCTTGGTGT TCATCTTTTT       540
TTTTAATGAT AAGCATTTTG TCGTTTATAC TTTTTATATT TCGATATTAA ACCACCTATG       600
AAGTTCATTT TAATCGCCAG ATAAGCAATA TATTGTGTAA ATATTTGTAT TCTTTATCAG       660
GAAATTCAGG GAGACGGGGA AGTTACTATC TACTAAAAGC CAAACAATTT CTTACAGTTT       720
TACTCTCTCT ACTCTAGAGT                                                   740
```

(2) INFORMATION FOR SEQ ID NO:15:

(i) SEQUENCE CHARACTERISTICS:
        (A) LENGTH: 60 base pairs (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GCTTGGATCC AGATCTACCA TGTCTCGCTC CGTGGCCTTA GCTGTGCTCG CGCTACTCTC        60

(2) INFORMATION FOR SEQ ID NO:16:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

GGATCCGGAT GGTTACATGT CGCGATCCCA CTTAAC                                  36

(2) INFORMATION FOR SEQ ID NO:17:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

GGAGCCGTGA CTGACTGAG                                                     19

(2) INFORMATION FOR SEQ ID NO:18:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

CCCTCGGCAC TGACTGACTC CTAG                                               24

(2) INFORMATION FOR SEQ ID NO:19:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

GATCCTTATT AGATCTCACC ATCACCATCA CCATTGAG                                38

(2) INFORMATION FOR SEQ ID NO:20:

(i) SEQUENCE CHARACTERISTICS:
              (A) LENGTH: 38 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

TCGACTCAAT GGTGATGGTG ATGGTGAGAT CTAATAAG                                38

(2) INFORMATION FOR SEQ ID NO:21:

(i) SEQUENCE CHARACTERISTICS:
              (A) LENGTH: 3875 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:21:

TTGCAGGACA GGATGTGGTG CCCGATGTGA CTAGCTCTTT GCTGCAGGCC GTCCTATCCT         60

CTGGTTCCGA TAAGAGACCC AGAACTCCGG CCCCCCACCG CCCACCGCCA CCCCCATACA        120

TATGTGGTAC GCAAGTAAGA GTGCCTGCGC ATGCCCCATG TGCCCCACCA AGAGcTTTGC        180

ATCCCATACA AGTCCCCAAA GTGGAGAACC GAACCAATTC TTCGCGGGCA GAACAAAAGC        240

TTCTGCACAC GTCTCCACTC GAATTTGGAG CCGGCCGGCG TGTGCAAAAG AGGTGAATCG        300

AACGAAAGAC CCGTGTGTAA AGCCGCGTTT CCAAAATGTA TAAAACCGAG AGCATCTGGC        360

CAATGTGCAT CAGTTGTGGT CAGCAGCAAA ATCAAGTGAA TCATCTCAGT GCAACTAAAG        420

GGGAATTCGA GCTCGGTACC CGGGGATCCT TATTAGATCT CACCATCACC ATCACCATTG        480

AGTCGACCTG CAGGCATGCA AGCTATTCGA TGCACACTCA CATTCTTCTC CTAATACGAT        540

AATAAAACTT TCCATGAAAA ATATGGAAAA ATATATGAAA ATTGAGAAAT CCAAAAAACT        600

GATAAACGCT CTACTTAATT AAAATAGATA AATGGGAGCG GCAGGAATGG CGGAGCATGG        660

CCAAGTTCCT CCGCCAATCA GTCGTAAAAC AGAAGTCGTG GAAAGCGGAT AGAAAGAATG        720

TTCGATTTGA CGGGCAAGCA TGTCTGCTAT GTGGCGGATT GCGGAGGAAT TGCACTGGAG        780

ACCAGCAAGG TTCTCATGAC CAAGAATATA GCGGTGAGTG AGCGGGAAGC TCGGTTTCTG        840

TCCAGATCGA ACTCAAAACT AGTCCAGCCA GTCGCTGTCG AAACTAATTA AGTtAATGAG        900

TTTTTCATGT TAGTTTCGCG CTGAGCAACA ATTAAGTTTA TGTTTCAGTT CGGCTTAGAT        960

-continued

| | | | | | |
|---|---|---|---|---|---|
| TTCGCTGAAG | GACTTGCCAC | TTTCAATCAA | TACTTTAGAA | CAAAATCAAA | ACTCATTCTA | 1020 |
| ATAGCTTGGT | GTTCATCTTT | TTTTTTAATG | ATAAGCATTT | TGTCGTTTAT | ACTTTTTATA | 1080 |
| TTTCGATATT | AAACCACCTA | TGAAGTctAT | TTTAATCGCC | AGATAAGCAA | TATATTGTGT | 1140 |
| AAATATTTGT | ATTCTTTATC | AGGAAATTCA | GGGAGACGGG | AAGTTACTAT | CTACTAAAAG | 1200 |
| CCAAACAATT | TCTTACAGTT | TTACTCTCTC | TACTCTAGAG | TAGCTTGGCA | CTGGCCGTCG | 1260 |
| TTTTACAACG | TCGTGACTGG | GAAAACCCTG | GCGTTACCCA | ACTTAATCGC | CTTGCAGCAC | 1320 |
| ATCCCCCTTT | CGCCAGCTGG | CGTAATAGCG | AAGAGGCCCG | CACCGATCGC | CCTTCCCAAC | 1380 |
| AGTTGCGCAG | CCTGAATGGC | GAATGGCGCC | TGATGCGGTA | TTTTCTCCTT | ACGCATCTGT | 1440 |
| GCGGTATTTC | ACACCGCATA | TGGTGCACTC | TCAGTACAAT | CTGCTCTGAT | GCCGCATAGT | 1500 |
| TAAGCCAGCC | CCGACACCCG | CCAACACCCG | CTGACGCGCC | CTGACGGGCT | TGTCTGCTCC | 1560 |
| CGGCATCCGC | TTACAGACAA | GCTGTGACCG | TCTCCGGGAG | CTGCATGTGT | CAGAGGTTTT | 1620 |
| CACCGTCATC | ACCGAAACGC | GCGAGACGAA | AGGGCCTCGT | GATACGCCTA | TTTTTATAGG | 1680 |
| TTAATGTCAT | GATAATAATG | GTTTCTTAGA | CGTCAGGTGG | CACTTTTCGG | GGAAATGTGC | 1740 |
| GCGGAACCCC | TATTTGTTTA | TTTTTCTAAA | TACATTCAAA | TATGTATCCG | CTCATGAGAC | 1800 |
| AATAACCCTG | ATAAATGCTT | CAATAATATT | GAAAAAGGAA | GAGTATGAGT | ATTCAACATT | 1860 |
| TCCGTGTCGC | CCTTATTCCC | TTTTTTGCGG | CATTTTGCCT | TCCTGTTTTT | GCTCACCCAG | 1920 |
| AAACGCTGGT | GAAAGTAAAA | GATGCTGAAG | ATCAGTTGGG | TGCACGAGTG | GGTTACATCG | 1980 |
| AACTGGATCT | CAACAGCGGT | AAGATCCTTG | AGAGTTTTCG | CCCCGAAGAA | CGTTTTCCAA | 2040 |
| TGATGAGCAC | TTTTAAAGTT | CTGCTATGTG | GCGCGGTATT | ATCCCGTATT | GACGCCGGGC | 2100 |
| AAGAGCAACT | CGGTCGCCGC | ATACACTATT | CTCAGAATGA | CTTGGTTGAG | TACTCACCAG | 2160 |
| TCACAGAAAA | GCATCTTACG | GATGGCATGA | CAGTAAGAGA | ATTATGCAGT | GCTGCCATAA | 2220 |
| CCATGAGTGA | TAACACTGCG | GCCAACTTAC | TTCTGACAAC | GATCGGAGGA | CCGAAGGAGC | 2280 |
| TAACCGCTTT | TTTGCACAAC | ATGGGGGATC | ATGTAACTCG | CCTTGATCGT | TGGGAACCGG | 2340 |
| AGCTGAATGA | AGCCATACCA | AACGACGAGC | GTGACACCAC | GATGCCTGTA | GCAATGGCAA | 2400 |
| CAACGTTGCG | CAAACTATTA | ACTGGCGAAC | TACTTACTCT | AGCTTCCCGG | CAACAATTAA | 2460 |
| TAGACTGGAT | GGAGGCGGAT | AAAGTTGCAG | GACCACTTCT | GCGCTCGGCC | CTTCCGGCTG | 2520 |
| GCTGGTTTAT | TGCTGATAAA | TCTGGAGCCG | GTGAGCGTGG | GTCTCGCGGT | ATCATTGCAG | 2580 |
| CACTGGGGCC | AGATGGTAAG | CCCTCCCGTA | TCGTAGTTAT | CTACACGACG | GGGAGTCAGG | 2640 |
| CAACTATGGA | TGAACGAAAT | AGACAGATCG | CTGAGATAGG | TGCCTCACTG | ATTAAGCATT | 2700 |
| GGTAACTGTC | AGACCAAGTT | TACTCATATA | TACTTTAGAT | TGATTTAAAA | CTTCATTTTT | 2760 |
| AATTTAAAAG | GATCTAGGTG | AAGATCCTTT | TTGATAATCT | CATGACCAAA | ATCCCTTAAC | 2820 |
| GTGAGTTTTC | GTTCCACTGA | GCGTCAGACC | CCGTAGAAAA | GATCAAAGGA | TCTTCTTGAG | 2880 |
| ATCCTTTTTT | TCTGCGCGTA | ATCTGCTGCT | TGCAAACAAA | AAAACCACCG | CTACCAGCGG | 2940 |
| TGGTTTGTTT | GCCGGATCAA | GAGCTACCAA | CTCTTTTTCC | GAAGGTAACT | GGCTTCAGCA | 3000 |
| GAGCGCAGAT | ACCAAATACT | GTCCTTCTAG | TGTAGCCGTA | GTTAGGCCAC | CACTTCAAGA | 3060 |
| ACTCTGTAGC | ACCGCCTACA | TACCTCGCTC | TGCTAATCCT | GTTACCAGTG | GCTGCTGCCA | 3120 |
| GTGGCGATAA | GTCGTGTCTT | ACCGGGTTGG | ACTCAAGACG | ATAGTTACCG | GATAAGGCGC | 3180 |
| AGCGGTCGGG | CTGAACGGGG | GGTTCGTGCA | CACAGCCCAG | CTTGGAGCGA | ACGACCTACA | 3240 |
| CCGAACTGAG | ATACCTACAG | CGTGAGCATT | GAGAAAGCGC | CACGCTTCCC | GAAGGGAGAA | 3300 |
| AGGCGGACAG | GTATCCGGTA | AGCGGCAGGG | TCGGAACAGG | AGAGCGCACG | AGGGAGCTTC | 3360 |

```
CAGGGGGAAA CGCCTGGTAT CTTTATAGTC CTGTCGGGTT TCGCCACCTC TGACTTGAGC    3420

GTCGATTTTT GTGATGCTCG TCAGGGGGGC GGAGCCTATG GAAAAACGCC AGCAACGCGG    3480

CCTTTTTACG GTCCTGGCCT TTTGCTGGCC TTTTGCTCAC ATGTCTTTCC TGCGTTATCC    3540

CCTGATTCTG TGGATAACCG TATTACCGCC TTTGAGTGAG CTGATACCGC TCGCCGCAGC    3600

CGAACcGACC GAGCGCAGCG AGTCAGTGAG CGAGGAAGCG GAAGAGCGCC CAATACGCAA    3660

ACCGCCTCTC CCCGCGCGTT GGCCGATTCA TTAATGCAGC TGGCACGACA GGTTTCCCGA    3720

CTGGAAAGCG GGCAGTGAGC GCAACGCAAT TAATGTGAGT TAGCTCACTC ATTAGGCACC    3780

CCAGGCTTTA CACTTTATGC TTCCGGCTCG TATGTTGTGT GGAATTGTGA GCGGATAACA    3840

ATTTCACACA GGAAACAGCT ATGACATGAT TACCG                               3875
```

(2) INFORMATION FOR SEQ ID NO:22:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

```
GATCCTTATT AGATCTTACC CATACGACGT CCCAGATTAC GCTCGATCTC ACCATCACCA    60

TCACCATTGA G                                                         71
```

(2) INFORMATION FOR SEQ ID NO:23:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

```
TCGACTCAAT GGTGATGGTG ATGGTGAGAT CGAGCGTAAT CTGGGACGTC GTATGGGTAA    60

GATCTAATAA G                                                         71
```

(2) INFORMATION FOR SEQ ID NO:24:

(i) SEQUENCE CHARACTERISTICS:
        (A) LENGTH: 3908 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:24:

```
TTGCAGGACA GGATGTGGTG CCCGATGTGA CTAGCTCTTT GCTGCAGGCC GTCCTATCCT    60
```

-continued

```
CTGGTTCCGA TAAGAGACCC AGAACTCCGG CCCCCCACCG CCCACCGCCA CCCCCATACA    120

TATGTGGTAC GCAAGTAAGA GTGCCTGCGC ATGCCCCATG TGCCCCACCA AGAGcTTTGC    180

ATCCCATACA AGTCCCCAAA GTGGAGAACC GAACCAATTC TTCGCGGGCA GAACAAAAGC    240

TTCTGCACAC GTCTCCACTC GAATTTGGAG CCGGCCGGCG TGTGCAAAAG AGGTGAATCG    300

AACGAAAGAC CCGTGTGTAA AGCCGCGTTT CCAAAATGTA TAAAACCGAG AGCATCTGGC    360

CAATGTGCAT CAGTTGTGGT CAGCAGCAAA ATCAAGTGAA TCATCTCAGT GCAACTAAAG    420

GGGAATTCGA GCTCGGTACC CGGGGATCCT TATTAGATCT TACCCATACG ACGTCCCAGA    480

TTACGCTCGA TCTCACCATC ACCATCACCA TTGAGTCGAC CTGCAGGCAT GCAAGCTATT    540

CGATGCACAC TCACATTCTT CTCCTAATAC GATAATAAAA CTTTCCATGA AAATATGGA    600

AAAATATATG AAAATTGAGA ATCCAAAAA ACTGATAAAC GCTCTACTTA ATTAAAATAG    660

ATAAATGGGA GCGGCAGGAA TGGCGGAGCA TGGCCAAGTT CCTCCGCCAA TCAGTCGTAA    720

AACAGAAGTC GTGGAAAGCG GATAGAAAGA ATGTTCGATT TGACGGGCAA GCATGTCTGC    780

TATGTGGCGG ATTGCGGAGG AATTGCACTG GAGACCAGCA AGGTTCTCAT GACCAAGAAT    840

ATAGCGGTGA GTGAGCGGGA AGCTCGGTTT CTGTCCAGAT CGAACTCAAA ACTAGTCCAG    900

CCAGTCGCTG TCGAAACTAA TTAAGTtAAT GAGTTTTTCA TGTTAGTTTC GCGCTGAGCA    960

ACAATTAAGT TTATGTTTCA GTTCGGCTTA GATTTCGCTG AAGGACTTGC CACTTTCAAT   1020

CAATACTTTA GAACAAAATC AAAACTCATT CTAATAGCTT GGTGTTCATC TTTTTTTTTA   1080

ATGATAAGCA TTTTGTCGTT TATACTTTTT ATATTTCGAT ATTAAACCAC CTATGAAGTc   1140
tATTTTAATC GCCAGATAAG CAATATATTG TGTAAATATT TGTATTCTTT ATCAGGAAAT   1200

TCAGGGAGAC GGGAAGTTAC TATCTACTAA AAGCCAAACA ATTTCTTACA GTTTTACTCT   1260

CTCTACTCTA GAGTAGCTTG GCACTGGCCG TCGTTTTACA ACGTCGTGAC TGGGAAAACC   1320

CTGGCGTTAC CCAACTTAAT CGCCTTGCAG CACATCCCCC TTTCGCCAGC TGGCGTAATA   1380

GCGAAGAGGC CCGCACCGAT CGCCCTTCCC AACAGTTGCG CAGCCTGAAT GGCGAATGGC   1440

GCCTGATGCG GTATTTTCTC CTTACGCATC TGTGCGGTAT TCACACCGC ATATGGTGCA    1500

CTCTCAGTAC AATCTGCTCT GATGCCGCAT AGTTAAGCCA GCCCCGACAC CGCCAACAC    1560

CCGCTGACGC GCCCTGACGG GCTTGTCTGC TCCCGGCATC CGCTTACAGA CAAGCTGTGA   1620

CCGTCTCCGG GAGCTGCATG TGTCAGAGGT TTTCACCGTC ATCACCGAAA CGCGCGAGAC   1680

GAAAGGGCCT CGTGATACGC CTATTTTTAT AGGTTAATGT CATGATAATA ATGGTTTCTT   1740

AGACGTCAGG TGGCACTTTT CGGGGAAATG TGCGCGGAAC CCCTATTTGT TTATTTTTCT   1800

AAATACATTC AAATATGTAT CCGCTCATGA GACAATAACC CTGATAAATG CTTCAATAAT   1860

ATTGAAAAAG GAAGAGTATG AGTATTCAAC ATTTCCGTGT CGCCCTTATT CCCTTTTTTG   1920

CGGCATTTTG CCTTCCTGTT TTTGCTCACC CAGAAACGCT GGTGAAAGTA AAAGATGCTG   1980

AAGATCAGTT GGGTGCACGA GTGGGTTACA TCGAACTGGA TCTCAACAGC GGTAAGATCC   2040

TTGAGAGTTT TCGCCCCGAA GAACGTTTTC CAATGATGAG CACTTTTAAA GTTCTGCTAT   2100

GTGGCGCGGT ATTATCCCGT ATTGACGCCG GGCAAGAGCA ACTCGGTCGC CGCATACACT   2160

ATTCTCAGAA TGACTTGGTT GAGTACTCAC CAGTCACAGA AAAGCATCTT ACGGATGGCA   2220

TGACAGTAAG AGAATTATGC AGTGCTGCCA TAACCATGAG TGATAACACT GCGGCCAACT   2280

TACTTCTGAC AACGATCGGA GGACCGAAGG AGCTAACCGC TTTTTTGCAC AACATGGGGG   2340

ATCATGTAAC TCGCCTTGAT CGTTGGGAAC CGGAGCTGAA TGAAGCCATA CCAAACGACG   2400
```

```
AGCGTGACAC CACGATGCCT GTAGCAATGG CAACAACGTT GCGCAAACTA TTAACTGGCG      2460

AACTACTTAC TCTAGCTTCC CGGCAACAAT TAATAGACTG GATGGAGGCG GATAAAGTTG      2520

CAGGACCACT TCTGCGCTCG GCCCTTCCGG CTGGCTGGTT TATTGCTGAT AAATCTGGAG      2580

CCGGTGAGCG TGGGTCTCGC GGTATCATTG CAGCACTGGG GCCAGATGGT AAGCCCTCCC      2640

GTATCGTAGT TATCTACACG ACGGGGAGTC AGGCAACTAT GGATGAACGA AATAGACAGA      2700

TCGCTGAGAT AGGTGCCTCA CTGATTAAGC ATTGGTAACT GTCAGACCAA GTTTACTCAT      2760

ATATACTTTA GATTGATTTA AAACTTCATT TTTAATTTAA AAGGATCTAG GTGAAGATCC      2820

TTTTTGATAA TCTCATGACC AAAATCCCTT AACGTGAGTT TTCGTTCCAC TGAGCGTCAG      2880

ACCCCGTAGA AAAGATCAAA GGATCTTCTT GAGATCCTTT TTTTCTGCGC GTAATCTGCT      2940

GCTTGCAAAC AAAAAAACCA CCGCTACCAG CGGTGGTTTG TTTGCCGGAT CAAGAGCTAC      3000

CAACTCTTTT TCCGAAGGTA ACTGGCTTCA GCAGAGCGCA GATACCAAAT ACTGTCCTTC      3060

TAGTGTAGCC GTAGTTAGGC CACCACTTCA AGAACTCTGT AGCACCGCCT ACATACCTCG      3120

CTCTGCTAAT CCTGTTACCA GTGGCTGCTG CCAGTGGCGA TAAGTCGTGT CTTACCGGGT      3180

TGGACTCAAG ACGATAGTTA CCGGATAAGG CGCAGCGGTC GGGCTGAACG GGGGGTTCGT      3240

GCACACAGCC CAGCTTGGAG CGAACGACCT ACACCGAACT GAGATACCTA CAGCGTGAGC      3300

ATTGAGAAAG CGCCACGCTT CCCGAAGGGA GAAAGGCGGA CAGGTATCCG GTAAGCGGCA      3360

GGGTCGGAAC AGGAGAGCGC ACGAGGGAGC TTCCAGGGGG AAACGCCTGG TATCTTTATA      3420

GTCCTGTCGG GTTTCGCCAC CTCTGACTTG AGCGTCGATT TTTGTGATGC TCGTCAGGGG      3480

GGCGGAGCCT ATGGAAAAAC GCCAGCAACG CGGCCTTTTT ACGGTCCTGG CCTTTTGCTG      3540

GCCTTTTGCT CACATGTCTT TCCTGCGTTA TCCCCTGATT CTGTGGATAA CCGTATTACC      3600

GCCTTTGAGT GAGCTGATAC CGCTCGCCGC AGCCGAACCG ACCGAGCGCA GCGAGTCAGT      3660

GAGCGAGGAA GCGGAAGAGC GCCCAATACG CAAACCGCCT CTCCCCGCGC GTTGGCCGAT      3720

TCATTAATGC AGCTGGCACG ACAGGTTTCC CGACTGGAAA GCGGGCAGTG AGCGCAACGC      3780

AATTAATGTG AGTTAGCTCA CTCATTAGGC ACCCCAGGCT TTACACTTTA TGCTTCCGGC      3840

TCGTATGTTG TGTGGAATTG TGAGCGGATA ACAATTTCAC ACAGGAAACA GCTATGACAT      3900

GATTACCG                                                              3908
```

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

```
GATCCTTATT AGATCTCACC ATCACCATCA CCATTGTTGA G                         41
```

(2) INFORMATION FOR SEQ ID NO:26:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

| | |
|---|---|
| TCGACTCAAC AATGGTGATG GTGATGGTGA GATCTAATAA G | 41 |

(2) INFORMATION FOR SEQ ID NO:27:

(i) SEQUENCE CHARACTERISTICS:
        (A) LENGTH: 3878 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:27:

| | |
|---|---|
| TTGCAGGACA GGATGTGGTG CCCGATGTGA CTAGCTCTTT GCTGCAGGCC GTCCTATCCT | 60 |
| CTGGTTCCGA TAAGAGACCC AGAACTCCGG CCCCCCACCG CCCACCGCCA CCCCCATACA | 120 |
| TATGTGGTAC GCAAGTAAGA GTGCCTGCGC ATGCCCCATG TGCCCCACCA AGAGcTTTGC | 180 |
| ATCCCATACA AGTCCCCAAA GTGGAGAACC GAACCAATTC TTCGCGGGCA GAACAAAAGC | 240 |
| TTCTGCACAC GTCTCCACTC GAATTTGGAG CCGGCCGGCG TGTGCAAAAG AGGTGAATCG | 300 |
| AACGAAAGAC CCGTGTGTAA AGCCGCGTTT CCAAAATGTA TAAAACCGAG AGCATCTGGC | 360 |
| CAATGTGCAT CAGTTGTGGT CAGCAGCAAA ATCAAGTGAA TCATCTCAGT GCAACTAAAG | 420 |
| GGGAATTCGA GCTCGGTACC CGGGGATCCT TATTAGATCT CACCATCACC ATCACCATTG | 480 |
| TTGAGTCGAC CTGCAGGCAT GCAAGCTATT CGATGCACAC TCACATTCTT CTCCTAATAC | 540 |
| GATAATAAAA CTTTCCATGA AAATATGGA AAAATATATG AAAATTGAGA ATCCAAAAA | 600 |
| ACTGATAAAC GCTCTACTTA ATTAAAATAG ATAAATGGGA GCGGCAGGAA TGGCGGAGCA | 660 |
| TGGCCAAGTT CCTCCGCCAA TCAGTCGTAA AACAGAAGTC GTGGAAAGCG GATAGAAAGA | 720 |
| ATGTTCGATT TGACGGGCAA GCATGTCTGC TATGTGGCGG ATTGCGGAGG AATTGCACTG | 780 |
| GAGACCAGCA AGGTTCTCAT GACCAAGAAT ATAGCGGTGA GTGAGCGGGA AGCTCGGTTT | 840 |
| CTGTCCAGAT CGAACTCAAA ACTAGTCCAG CCAGTCGCTG TCGAAACTAA TTAAGTtAAT | 900 |
| GAGTTTTTCA TGTTAGTTTC GCGCTGAGCA ACAATTAAGT TTATGTTTCA GTTCGGCTTA | 960 |
| GATTTCGCTG AAGGACTTGC CACTTTCAAT CAATACTTTA GAACAAAATC AAAACTCATT | 1020 |
| CTAATAGCTT GGTGTTCATC TTTTTTTTA ATGATAAGCA TTTTGTCGTT TATACTTTTT | 1080 |
| ATATTTCGAT ATTAAACCAC CTATGAAGTc tATTTTAATC GCCAGATAAG CAATATATTG | 1140 |
| TGTAAATATT TGTATTCTTT ATCAGGAAAT TCAGGGAGAC GGGAAGTTAC TATCTACTAA | 1200 |
| AAGCCAAACA ATTTCTTACA GTTTTACTCT CTCTACTCTA GAGTAGCTTG GCACTGGCCG | 1260 |
| TCGTTTTACA ACGTCGTGAC TGGGAAAACC CTGGCGTTAC CCAACTTAAT CGCCTTGCAG | 1320 |
| CACATCCCCC TTTCGCCAGC TGGCGTAATA GCGAAGAGGC CCGCACCGAT CGCCCTTCCC | 1380 |
| AACAGTTGCG CAGCCTGAAT GGCGAATGGC GCCTGATGCG GTATTTTCTC CTTACGCATC | 1440 |
| TGTGCGGTAT TTCACACCGC ATATGGTGCA CTCTCAGTAC AATCTGCTCT GATGCCGCAT | 1500 |
| AGTTAAGCCA GCCCCGACAC CCGCCAACAC CCGCTGACGC GCCCTGACGG GCTTGTCTGC | 1560 |

-continued

```
TCCCGGCATC CGCTTACAGA CAAGCTGTGA CCGTCTCCGG GAGCTGCATG TGTCAGAGGT    1620

TTTCACCGTC ATCACCGAAA CGCGCGAGAC GAAAGGGCCT CGTGATACGC CTATTTTTAT    1680

AGGTTAATGT CATGATAATA ATGGTTTCTT AGACGTCAGG TGGCACTTTT CGGGGAAATG    1740

TGCGCGGAAC CCCTATTTGT TTATTTTTCT AAATACATTC AAATATGTAT CCGCTCATGA    1800

GACAATAACC CTGATAAATG CTTCAATAAT ATTGAAAAAG GAAGAGTATG AGTATTCAAC    1860

ATTTCCGTGT CGCCCTTATT CCCTTTTTTG CGGCATTTTG CCTTCCTGTT TTTGCTCACC    1920

CAGAAACGCT GGTGAAAGTA AAAGATGCTG AAGATCAGTT GGGTGCACGA GTGGGTTACA    1980

TCGAACTGGA TCTCAACAGC GGTAAGATCC TTGAGAGTTT TCGCCCCGAA GAACGTTTTC    2040

CAATGATGAG CACTTTTAAA GTTCTGCTAT GTGGCGCGGT ATTATCCCGT ATTGACGCCG    2100

GGCAAGAGCA ACTCGGTCGC CGCATACACT ATTCTCAGAA TGACTTGGTT GAGTACTCAC    2160

CAGTCACAGA AAAGCATCTT ACGGATGGCA TGACAGTAAG AGAATTATGC AGTGCTGCCA    2220

TAACCATGAG TGATAACACT GCGGCCAACT TACTTCTGAC AACGATCGGA GGACCGAAGG    2280

AGCTAACCGC TTTTTTGCAC AACATGGGGG ATCATGTAAC TCGCCTTGAT CGTTGGGAAC    2340

CGGAGCTGAA TGAAGCCATA CCAAACGACG AGCGTGACAC CACGATGCCT GTAGCAATGG    2400

CAACAACGTT GCGCAAACTA TTAACTGGCG AACTACTTAC TCTAGCTTCC CGGCAACAAT    2460

TAATAGACTG GATGGAGGCG GATAAAGTTG CAGGACCACT TCTGCGCTCG GCCCTTCCGG    2520

CTGGCTGGTT TATTGCTGAT AAATCTGGAG CCGGTGAGCG TGGGTCTCGC GGTATCATTG    2580

CAGCACTGGG GCCAGATGGT AAGCCCTCCC GTATCGTAGT TATCTACACG ACGGGGAGTC    2640

AGGCAACTAT GGATGAACGA AATAGACAGA TCGCTGAGAT AGGTGCCTCA CTGATTAAGC    2700

ATTGGTAACT GTCAGACCAA GTTTACTCAT ATATACTTTA GATTGATTTA AAACTTCATT    2760

TTTAATTTAA AAGGATCTAG GTGAAGATCC TTTTTGATAA TCTCATGACC AAAATCCCTT    2820

AACGTGAGTT TTCGTTCCAC TGAGCGTCAG ACCCCGTAGA AAAGATCAAA GGATCTTCTT    2880

GAGATCCTTT TTTTCTGCGC GTAATCTGCT GCTTGCAAAC AAAAAAACCA CCGCTACCAG    2940

CGGTGGTTTG TTTGCCGGAT CAAGAGCTAC CAACTCTTTT TCCGAAGGTA ACTGGCTTCA    3000

GCAGAGCGCA GATACCAAAT ACTGTCCTTC TAGTGTAGCC GTAGTTAGGC CACCACTTCA    3060

AGAACTCTGT AGCACCGCCT ACATACCTCG CTCTGCTAAT CCTGTTACCA GTGGCTGCTG    3120

CCAGTGGCGA TAAGTCGTGT CTTACCGGGT TGGACTCAAG ACGATAGTTA CCGGATAAGG    3180

CGCAGCGGTC GGGCTGAACG GGGGGTTCGT GCACACAGCC CAGCTTGGAG CGAACGACCT    3240

ACACCGAACT GAGATACCTA CAGCGTGAGC ATTGAGAAAG CGCCACGCTT CCCGAAGGGA    3300

GAAAGGCGGA CAGGTATCCG GTAAGCGGCA GGGTCGGAAC AGGAGAGCGC ACGAGGGAGC    3360

TTCCAGGGGG AAACGCCTGG TATCTTTATA GTCCTGTCGG GTTTCGCCAC CTCTGACTTG    3420

AGCGTCGATT TTTGTGATGC TCGTCAGGGG GGCGGAGCCT ATGGAAAAAC GCCAGCAACG    3480

CGGCCTTTTT ACGGTCCTGG CCTTTTGCTG GCCTTTTGCT CACATGTCTT CCTGCGTTA    3540

TCCCCTGATT CTGTGGATAA CCGTATTACC GCCTTTGAGT GAGCTGATAC CGCTCGCCGC    3600

AGCCGAACcG ACCGAGCGCA GCGAGTCAGT GAGCGAGGAA GCGGAAGAGC GCCCAATACG    3660

CAAACCGCCT CTCCCCGCGC GTTGGCCGAT TCATTAATGC AGCTGGCACG ACAGGTTTCC    3720

CGACTGGAAA GCGGGCAGTG AGCGCAACGC AATTAATGTG AGTTAGCTCA CTCATTAGGC    3780

ACCCCAGGCT TTACACTTTA TGCTTCCGGC TCGTATGTTG TGTGGAATTG TGAGCGGATA    3840

ACAATTTCAC ACAGGAAACA GCTATGACAT GATTACCG                           3878
```

(2) INFORMATION FOR SEQ ID NO:28:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

```
GATCCTTATT AGATCTGCTT GGCGCCATCC TCAATTTGGG GGTTGAG                47
```

(2) INFORMATION FOR SEQ ID NO:29:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

```
TCGACTCAAC CCCCAAATTG AGGATGGCGC CAAGCAGATC TAATAAG                47
```

(2) INFORMATION FOR SEQ ID NO:30:

(i) SEQUENCE CHARACTERISTICS:
        (A) LENGTH: 3883 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:30:

```
TTGCAGGACA GGATGTGGTG CCCGATGTGA CTAGCTCTTT GCTGCAGGCC GTCCTATCCT    60

TGGTTCCGAT AAGAGACCCA GAACTCCGGC CCCCCACCGC CCACCGCCAC CCCCATACAT   120

ATGTGGTACG CAAGTAAGAG TGCCTGCGCA TGCCCCATGT GCCCCACCAA GAGcTTTGCA   180

TCCCATACAA GTCCCCAAAG TGGAGAACCG AACCAATTCT TCGCGGGCAG AACAAAAGCT   240

TCTGCACACG TCTCCACTCG AATTTGGAGC CGGCCGGCGT GTGCAAAAGA GGTGAATCGA   300

ACGAAAGACC CGTGTGTAAA GCCGCGTTTC CAAAATGTAT AAAACCGAGA GCATCTGGCC   360

AATGTGCATC AGTTGTGGTC AGCAGCAAAA TCAAGTGAAT CATCTCAGTG CAACTAAAGG   420

GGAATTCGAG CTCGGTACCC GGGGATCCTT ATTAGATCTG CTTGGCGCCA TCCTCAATTT   480

GGGGGTTGAG TCGACCTGCA GGCATGCAAG CTATTCGATG CACACTCACA TTCTTCTCCT   540

AATACGATAA TAAAACTTTC CATGAAAAAT ATGGAAAAAT ATATGAAAAT TGAGAAATCC   600

AAAAAACTGA TAAACGCTCT ACTTAATTAA AATAGATAAA TGGGAGCGGC AGGAATGGCG   660

GAGCATGGCC AAGTTCCTCC GCCAATCAGT CGTAAAACAG AAGTCGTGGA AAGCGGATAG   720
```

```
AAAGAATGTT CGATTTGACG GGCAAGCATG TCTGCTATGT GGCGGATTGC GGAGGAATTG    780

CACTGGAGAC CAGCAAGGTT CTCATGACCA AGAATATAGC GGTGAGTGAG CGGGAAGCTC    840

GGTTTCTGTC CAGATCGAAC TCAAAACTAG TCCAGCCAGT CGCTGTCGAA ACTAATTAAG    900

TtAATGAGTT TTTCATGTTA GTTTCGCGCT GAGCAACAAT TAAGTTTATG TTTCAGTTCG    960

GCTTAGATTT CGCTGAAGGA CTTGCCACTT TCAATCAATA CTTTAGAACA AAATCAAAAC   1020

TCATTCTAAT AGCTTGGTGT TCATCTTTTT TTTTAATGAT AAGCATTTTG TCGTTTATAC   1080

TTTTTATATT TCGATATTAA ACCACCTATG AAGTctATTT TAATCGCCAG ATAAGCAATA   1140

TATTGTGTAA ATATTTGTAT TCTTTATCAG GAAATTCAGG GAGACGGGAA GTTACTATCT   1200

ACTAAAAGCC AAACAATTTC TTACAGTTTT ACTCTCTCTA CTCTAGAGTA GCTTGGCACT   1260

GGCCGTCGTT TTACAACGTC GTGACTGGGA AAACCCTGGC GTTACCCAAC TTAATCGCCT   1320

TGCAGCACAT CCCCCTTTCG CCAGCTGGCG TAATAGCGAA GAGGCCCGCA CCGATCGCCC   1380

TTCCCAACAG TTGCGCAGCC TGAATGGCGA ATGGCGCCTG ATGCGGTATT TTCTCCTTAC   1440

GCATCTGTGC GGTATTTCAC ACCGCATATG GTGCACTCTC AGTACAATCT GCTCTGATGC   1500

CGCATAGTTA AGCCAGCCCC GACACCCGCC AACACCCGCT GACGCGCCCT GACGGGCTTG   1560

TCTGCTCCCG GCATCCGCTT ACAGACAAGC TGTGACCGTC TCCGGGAGCT GCATGTGTCA   1620

GAGGTTTTCA CCGTCATCAC CGAAACGCGC GAGACGAAAG GGCCTCGTGA TACGCCTATT   1680

TTTATAGGTT AATGTCATGA TAATAATGGT TTCTTAGACG TCAGGTGGCA CTTTTCGGGG   1740

AAATGTGCGC GGAACCCCTA TTTGTTTATT TTTCTAAATA CATTCAAATA TGTATCCGCT   1800

CATGAGACAA TAACCCTGAT AAATGCTTCA ATAATATTGA AAAGGAAGA GTATGAGTAT   1860

TCAACATTTC CGTGTCGCCC TTATTCCCTT TTTTGCGGCA TTTTGCCTTC CTGTTTTTGC   1920

TCACCCAGAA ACGCTGGTGA AAGTAAAAGA TGCTGAAGAT CAGTTGGGTG CACGAGTGGG   1980

TTACATCGAA CTGGATCTCA ACAGCGGTAA GATCCTTGAG AGTTTTCGCC CCGAAGAACG   2040

TTTTCCAATG ATGAGCACTT TTAAAGTTCT GCTATGTGGC GCGGTATTAT CCCGTATTGA   2100

CGCCGGGCAA GAGCAACTCG GTCGCCGCAT ACACTATTCT CAGAATGACT TGGTTGAGTA   2160

CTCACCAGTC ACAGAAAAGC ATCTTACGGA TGGCATGACA GTAAGAGAAT TATGCAGTGC   2220

TGCCATAACC ATGAGTGATA ACACTGCGGC CAACTTACTT CTGACAACGA TCGGAGGACC   2280

GAAGGAGCTA ACCGCTTTTT TGCACAACAT GGGGGATCAT GTAACTCGCC TTGATCGTTG   2340

GGAACCGGAG CTGAATGAAG CCATACCAAA CGACGAGCGT GACACCACGA TGCCTGTAGC   2400

AATGGCAACA ACGTTGCGCA AACTATTAAC TGGCGAACTA CTTACTCTAG CTTCCCGGCA   2460

ACAATTAATA GACTGGATGG AGGCGGATAA AGTTGCAGGA CCACTTCTGC GCTCGGCCCT   2520

TCCGGCTGGC TGGTTTATTG CTGATAAATC TGGAGCCGGT GAGCGTGGGT CTCGCGGTAT   2580

CATTGCAGCA CTGGGGCCAG ATGGTAAGCC CTCCCGTATC GTAGTTATCT ACACGACGGG   2640

GAGTCAGGCA ACTATGGATG AACGAAATAG ACAGATCGCT GAGATAGGTG CCTCACTGAT   2700

TAAGCATTGG TAACTGTCAG ACCAAGTTTA CTCATATATA CTTTAGATTG ATTTAAAACT   2760

TCATTTTTAA TTTAAAAGGA TCTAGGTGAA GATCCTTTTT GATAATCTCA TGACCAAAAT   2820

CCCTTAACGT GAGTTTTCGT TCCACTGAGC GTCAGACCCC GTAGAAAAGA TCAAAGGATC   2880

TTCTTGAGAT CCTTTTTTTC TGCGCGTAAT CTGCTGCTTG CAAACAAAAA AACCACCGCT   2940

ACCAGCGGTG GTTTGTTTGC CGGATCAAGA GCTACCAACT CTTTTTCCGA AGGTAACTGG   3000

CTTCAGCAGA GCGCAGATAC CAAATACTGT CCTTCTAGTG TAGCCGTAGT TAGGCCACCA   3060

CTTCAAGAAC TCTGTAGCAC CGCCTACATA CCTCGCTCTG CTAATCCTGT TACCAGTGGC   3120
```

```
TGCTGCCAGT GGCGATAAGT CGTGTCTTAC CGGGTTGGAC TCAAGACGAT AGTTACCGGA      3180

TAAGGCGCAG CGGTCGGGCT GAACGGGGGG TTCGTGCACA CAGCCCAGCT TGGAGCGAAC      3240

GACCTACACC GAACTGAGAT ACCTACAGCG TGAGCATTGA GAAAGCGCCA CGCTTCCCGA      3300

AGGGAGAAAG GCGGACAGGT ATCCGGTAAG CGGCAGGGTC GGAACAGGAG AGCGCACGAG      3360

GGAGCTTCCA GGGGGAAACG CCTGGTATCT TTATAGTCCT GTCGGGTTTC GCCACCTCTG      3420

ACTTGAGCGT CGATTTTTGT GATGCTCGTC AGGGGGCGG AGCCTATGGA AAAACGCCAG       3480

CAACGCGGCC TTTTTACGGT CCTGGCCTTT TGCTGGCCTT TTGCTCACAT GTCTTTCCTG      3540

CGTTATCCCC TGATTCTGTG GATAACCGTA TTACCGCCTT TGAGTGAGCT GATACCGCTC      3600

GCCGCAGCCG AACCGACCGA GCGCAGCGAG TCAGTGAGCG AGGAAGCGGA AGAGCGCCCA      3660

ATACGCAAAC CGCCTCTCCC CGCGCGTTGG CCGATTCATT AATGCAGCTG GCACGACAGG      3720

TTTCCCGACT GGAAAGCGGG CAGTGAGCGC AACGCAATTA ATGTGAGTTA GCTCACTCAT      3780

TAGGCACCCC AGGCTTTACA CTTTATGCTT CCGGCTCGTA TGTTGTGTGG AATTGTGAGC      3840

GGATAACAAT TTCACACAGG AAACAGCTAT GACATGATTA CCG                       3883

(2) INFORMATION FOR SEQ ID NO:31:

(i) SEQUENCE CHARACTERISTICS:
        (A) LENGTH: 879 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:31:

GAATTCATGG GCCACACACG GAGGCAGGGA ACATCACCAT CCAAGTGTCC ATACCTCAAT       60

TTCTTTCAGC TCTTGGTGCT GGCTGGTCTT TCTCACTTCT GTTCAGGTGT TATCCACGTG      120

ACCAAGGAAG TGAAAGAAGT GGCAACGCTG TCCTGTGGTC ACAATGTTTC TGTTGAAGAG      180

CTGGCACAAA CTCGCATCTA CTGGCAAAAG GAGAAGAAAA TGGTGCTGAC TATGATGTCT      240

GGGGACATGA ATATATGGCC CGAGTACAAG AACCGGACCA TCTTTGATAT CACTAATAAC      300

CTCTCCATTG TGATCCTGGC TCTGCGCCCA TCTGACGAGG GCACATACGA GTGTGTTGTT      360

CTGAAGTATG AAAAAGACGC TTTCAAGCGG GAACACCTGG CTGAAGTGAC GTTATCAGTC      420

AAAGCTGACT TCCCTACACC TAGTATATCT GACTTTGAAA TTCCAACTTC TAATATTAGA      480

AGGATAATTT GCTCAACCTC TGGAGGTTTT CCAGAGCCTC ACCTCTCCTG GTTGGAAAAT      540

GGAGAAGAAT TAAATGCCAT CAACACAACA GTTTCCCAAG ATCCTGAAAC TGAGCTCTAT      600

GCTGTTAGCA GCAAACTGGA TTTCAATATG ACAACCAACC ACAGCTTCAT GTGTCTCATC      660

AAGTATGGAC ATTTAAGAGT GAATCAGACC TTCAACTGGA ATACAACCAA GCAAGAGCAT      720

TTTCCTGATA ACCTGCTCCC ATCCTGGGCC ATTACCTTAA TCTCAGTAAA TGGAATTTTT      780

GTGATATGCT GCCTGACCTA CTGCTTTGCC CCAAGATGCA GAGAGAGAAG GAGGAATGAG      840

AGATTGAGAA GGGAAAGTGT ACGCCCTGTA TAAGGATTC                            879

(2) INFORMATION FOR SEQ ID NO:32:

(i) SEQUENCE CHARACTERISTICS:
        (A) LENGTH: 738 base pairs
```

(B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:32:

| | | | | | |
|---|---|---|---|---|---|
| GAATTCATGG | GCCACACACG | GAGGCAGGGA | ACATCACCAT | CCAAGTGTCC | ATACCTCAAT | 60 |
| TTCTTTCAGC | TCTTGGTGCT | GGCTGGTCTT | TCTCACTTCT | GTTCAGGTGT | TATCCACGTG | 120 |
| ACCAAGGAAG | TGAAAGAAGT | GGCAACGCTG | TCCTGTGGTC | ACAATGTTTC | TGTTGAAGAG | 180 |
| CTGGCACAAA | CTCGCATCTA | CTGGCAAAAG | GAGAAGAAAA | TGGTGCTGAC | TATGATGTCT | 240 |
| GGGGACATGA | ATATATGGCC | CGAGTACAAG | AACCGGACCA | TCTTTGATAT | CACTAATAAC | 300 |
| CTCTCCATTG | TGATCCTGGC | TCTGCGCCCA | TCTGACGAGG | GCACATACGA | GTGTGTTGTT | 360 |
| CTGAAGTATG | AAAAAGACGC | TTTCAAGCGG | AACACCTGG | CTGAAGTGAC | GTTATCAGTC | 420 |
| AAAGCTGACT | TCCCTACACC | TAGTATATCT | GACTTTGAAA | TTCCAACTTC | TAATATTAGA | 480 |
| AGGATAATTT | GCTCAACCTC | TGGAGGTTTT | CCAGAGCCTC | ACCTCTCCTG | GTTGGAAAAT | 540 |
| GGAGAAGAAT | TAAATGCCAT | CAACACAACA | GTTTCCCAAG | ATCCTGAAAC | TGAGCTCTAT | 600 |
| GCTGTTAGCA | GCAAACTGGA | TTTCAATATG | ACAACCAACC | ACAGCTTCAT | GTGTCTCATC | 660 |
| AAGTATGGAC | ATTTAAGAGT | GAATCAGACC | TTCAACTGGA | ATACAACCAA | GCAAGAGCAT | 720 |
| TTTCCTGATA | ACGGATTC | | | | | 738 |

(2) INFORMATION FOR SEQ ID NO:33:

(i) SEQUENCE CHARACTERISTICS:
        (A) LENGTH: 1002 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

| | | | | | |
|---|---|---|---|---|---|
| GAGCTCATGG | ATCCCCAGTG | CACTATGGGA | CTGAGTAACA | TTCTCTTTGT | GATGGCCTTC | 60 |
| CTGCTCTCTG | GTGCTGCTCC | TCTGAAGATT | CAAGCTTATT | TCAATGAGAC | TGCAGACCTG | 120 |
| CCATGCCAAT | TTGCAAACTC | TCAAAACCAA | AGCCTGAGTG | AGCTAGTAGT | ATTTTGGCAG | 180 |
| GACCAGGAAA | ACTTGGTTCT | GAATGAGGTA | TACTTAGGCA | AAGAGAAATT | TGACAGTGTT | 240 |
| CATTCCAAGT | ATATGGGCCG | CACAAGTTTT | GATTCGGACA | GTTGGACCCT | GAGACTTCAC | 300 |
| AATCTTCAGA | TCAAGGACAA | GGGCTTGTAT | CAATGTATCA | TCCATCACAA | AAAGCCCACA | 360 |
| GGAATGATTC | GCATCCACCA | GATGAATTCT | GAACTGTCAG | TGCTTGCTAA | CTTCAGTCAA | 420 |
| CCTGAAATAG | TACCAATTTC | TAATATAACA | GAAAATGTGT | ACATAAATTT | GACCTGCTCA | 480 |
| TCTATACACG | GTTACCCAGA | ACCTAAGAAG | ATGAGTGTTT | TGCTAAGAAC | CAAGAATTCA | 540 |
| ACTATCGAGT | ATGATGGTAT | TATGCAGAAA | TCTCAAGATA | ATGTCACAGA | ACTGTACGAC | 600 |
| GTTTCCATCA | GCTTGTCTGT | TTCATTCCCT | GATGTTACGA | GCAATATGAC | CATCTTCTGT | 660 |
| ATTCTGGAAA | CTGACAAGAC | GCGGCTTTTA | TCTTCACCTT | TCTCTATAGA | GCTTGAGGAC | 720 |

```
CCTCAGCCTC CCCCAGACCA CATTCCTTGG ATTACAGCTG TACTTCCAAC AGTTATTATA    780

TGTGTGATGG TTTTCTGTCT AATTCTATGG AAATGGAAGA AGAAGAAGCG GCCTCGCAAC    840

TCTTATAAAT GTGGAACCAA CACAATGGAG AGGGAAGAGA GTGAACAGAC CAAGAAAAGA    900

GAAAAAATCC ATATACCTGA AGATCTGAT GAAGCCCAGC GTGTTTTAA AAGTTCGAAG     960

ACATCTTCAT GCGACAAAAG TGATACATGT TTTTAAGGGC CC                     1002
```

(2) INFORMATION FOR SEQ ID NO:34:

(i) SEQUENCE CHARACTERISTICS:
        (A) LENGTH: 751 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

```
GAGCTCATGG ATCCCCAGTG CACTATGGGA CTGAGTAACA TTCTCTTTGT GATGGCCTTC     60

CTGCTCTCTG GTGCTGCTCC TCTGAAGATT CAAGCTTATT TCAATGAGAC TGCAGACCTG    120

CCATGCCAAT TTGCAAACTC TCAAAACCAA AGCCTGAGTG AGCTAGTAGT ATTTTGGCAG    180

GACCAGGAAA ACTTGGTTCT GAATGAGGTA TACTTAGGCA AAGAGAAATT TGACAGTGTT    240

CATTCCAAGT ATATGGGCCG CACAAGTTTT GATTCGGACA GTTGGACCCT GAGACTTCAC    300

AATCTTCAGA TCAAGGACAA GGGCTTGTAT CAATGTATCA TCCATCACAA AAAGCCCACA    360

GGAATGATTC GCATCCACCA GATGAATTCT GAACTGTCAG TGCTTGCTAA CTTCAGTCAA    420

CCTGAAATAG TACCAATTTC TAATATAACA GAAAATGTGT ACATAAATTT GACCTGCTCA    480

TCTATACACG GTTACCCAGA ACCTAAGAAG ATGAGTGTTT TGCTAAGAAC CAAGAATTCA    540

ACTATCGAGT ATGATGGTAT TATGCAGAAA TCTCAAGATA ATGTCACAGA ACTGTACGAC    600

GTTTCCATCA GCTTGTCTGT TTCATTCCCT GATGTTACGA GCAATATGAC CATCTTCTGT    660

ATTCTGGAAA CTGACAAGAC GCGGCTTTTA TCTTCACCTT TCTCTATAGA GCTTGAGGAC    720

CCTCAGCCTC CCCCAGACCA CATTGGGGCC C                                  751
```

(2) INFORMATION FOR SEQ ID NO:35:

(i) SEQUENCE CHARACTERISTICS:
        (A) LENGTH: 1611 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

```
GAATTCATGG CTCCCAGCAG CCCCCGGCCC GCGCTGCCCG CACTCCTGGT CCTGCTCGGG     60

GCTCTGTTCC CAGGACCTGG CAATGCCCAG ACATCTGTGT CCCCCTCAAA AGTCATCCTG    120

CCCCGGGGAG GCTCCGTGCT GGTGACATGC AGCACCTCCT GTGACCAGCC CAAGTTGTTG    180

GGCATAGAGA CCCCGTTGCC TAAAAAGGAG TTGCTCCTGC CTGGGAACAA CCGGAAGGTG    240

TATGAACTGA GCAATGTGCA AGAAGATAGC CAACCAATGT GCTATTCAAA CTGCCCTGAT    300
```

-continued

```
GGGCAGTCAA CAGCTAAAAC CTTCCTCACC GTGTACTGGA CTCCAGAACG GGTGGAACTG      360

GCACCCCTCC CCTCTTGGCA GCCAGTGGGC AAGAACCTTA CCCTACGCTG CCAGGTGGAG      420

GGTGGGGCAC CCCGGGCCAA CCTCACCGTG GTGCTGCTCC GTGGGGAGAA GGAGCTGAAA      480

CGGGAGCCAG CTGTGGGGA GCCCGCTGAG GTCACGACCA CGGTGCTGGT GAGGAGAGAT       540

CACCATGGAG CCAATTTCTC GTGCCGCACT GAACTGGACC TGCGGCCCCA AGGGCTGGAG      600

CTGTTTGAGA CACCTCGGC CCCCTACCAG CTCCAGACCT TTGTCCTGCC AGCGACTCCC       660

CCACAACTTG TCAGCCCCCG GGTCCTAGAG GTGGACACGC AGGGGACCGT GGTCTGTTCC      720

CTGGACGGGC TGTTCCCAGT CTCGGAGGCC CAGGTCCACC TGGCACTGGG GGACCAGAGG     780

TTGAACCCCA CAGTCACCTA TGGCAACGAC TCCTTCTCGG CCAAGGCCTC AGTCAGTGTG      840

ACCGCAGAGG ACGAGGGCAC CCAGCGGCTG ACGTGTGCAG TAATACTGGG GAACCAGAGC      900

CAGGAGACAC TGCAGACAGT GACCATCTAC AGCTTTCCGG CGCCCAACGT GATTCTGACG      960

AAGCCAGAGG TCTCAGAAGG GACCGAGGTG ACAGTGAAGT GTGAGGCCCA CCCTAGAGCC     1020

AAGGTGACGC TGAATGGGGT TCCAGCCCAG CCACTGGGCC CGAGGGCCCA GCTCCTGCTG     1080

AAGGCCACCC CAGAGGACAA CGGGCGCAGC TTCTCCTGCT CTGCAACCCT GGAGGTGGCC     1140

GGCCAGCTTA TACACAAGAA CCAGACCCGG GAGCTTCGTG TCCTGTATGG CCCCCGACTG     1200

GACGAGAGGG ATTGTCCGGG AAACTGGACG TGGCCAGAAA ATTCCCAGCA GACTCCAATG     1260

TGCCAGGCTT GGGGGAACCC ATTGCCCGAG CTCAAGTGTC TAAAGGATGG CACTTTCCCA     1320

CTGCCCATCG GGGAATCAGT GACTGTCACT CGAGATCTTG AGGGCACCTA CCTCTGTCGG     1380

GCCAGGAGCA CTCAAGGGGA GGTCACCCGC GAGGTGACCG TGAATGTGCT CTCCCCCCGG     1440

TATGAGATTG TCATCATCAC TGTGGTAGCA GCCGCAGTCA TAATGGGCAC TGCAGGCCTC     1500

AGCACGTACC TCTATAACCG CCAGCGGAAG ATCAAGAAAT ACAGACTACA ACAGGCCCAA     1560

AAAGGGACCC CCATGAAACC GAACACACAA GCCACGCCTC CCTGAGGATC C              1611
```

(2) INFORMATION FOR SEQ ID NO:36:

(i) SEQUENCE CHARACTERISTICS:
        (A) LENGTH: 1452 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:36:

```
GAATTCATGG CTCCCAGCAG CCCCCGGCCC GCGCTGCCCG CACTCCTGGT CCTGCTCGGG       60

GCTCTGTTCC CAGGACCTGG CAATGCCCAG ACATCTGTGT CCCCCTCAAA AGTCATCCTG      120

CCCCGGGGAG GCTCCGTGCT GGTGACATGC AGCACCTCCT GTGACCAGCC CAAGTTGTTG      180

GGCATAGAGA CCCCGTTGCC TAAAAAGGAG TTGCTCCTGC CTGGGAACAA CCGGAAGGTG      240

TATGAACTGA GCAATGTGCA AGAAGATAGC CAACCAATGT GCTATTCAAA CTGCCCTGAT      300

GGGCAGTCAA CAGCTAAAAC CTTCCTCACC GTGTACTGGA CTCCAGAACG GGTGGAACTG      360

GCACCCCTCC CCTCTTGGCA GCCAGTGGGC AAGAACCTTA CCCTACGCTG CCAGGTGGAG      420

GGTGGGGCAC CCCGGGCCAA CCTCACCGTG GTGCTGCTCC GTGGGGAGAA GGAGCTGAAA      480

CGGGAGCCAG CTGTGGGGA GCCCGCTGAG GTCACGACCA CGGTGCTGGT GAGGAGAGAT       540
```

```
CACCATGGAG CCAATTTCTC GTGCCGCACT GAACTGGACC TGCGGCCCCA AGGGCTGGAG      600

CTGTTTGAGA ACACCTCGGC CCCCTACCAG CTCCAGACCT TTGTCCTGCC AGCGACTCCC      660

CCACAACTTG TCAGCCCCCG GGTCCTAGAG GTGGACACGC AGGGGACCGT GGTCTGTTCC      720

CTGGACGGGC TGTTCCCAGT CTCGGAGGCC CAGGTCCACC TGGCACTGGG GGACCAGAGG      780

TTGAACCCCA CAGTCACCTA TGGCAACGAC TCCTTCTCGG CCAAGGCCTC AGTCAGTGTG      840

ACCGCAGAGG ACGAGGGCAC CCAGCGGCTG ACGTGTGCAG TAATACTGGG GAACCAGAGC      900

CAGGAGACAC TGCAGACAGT GACCATCTAC AGCTTTCCGG CGCCCAACGT GATTCTGACG      960

AAGCCAGAGG TCTCAGAAGG GACCGAGGTG ACAGTGAAGT GTGAGGCCCA CCCTAGAGCC     1020

AAGGTGACGC TGAATGGGGT TCCAGCCCAG CCACTGGGCC CGAGGGCCCA GCTCCTGCTG     1080

AAGGCCACCC CAGAGGACAA CGGGCGCAGC TTCTCCTGCT CTGCAACCCT GGAGGTGGCC     1140

GGCCAGCTTA TACACAAGAA CCAGACCCGG GAGCTTCGTG TCCTGTATGG CCCCCGACTG     1200

GACGAGAGGG ATTGTCCGGG AAACTGGACG TGGCCAGAAA ATTCCCAGCA GACTCCAATG     1260

TGCCAGGCTT GGGGGAACCC ATTGCCCGAG CTCAAGTGTC TAAAGGATGG CACTTTCCCA     1320

CTGCCCATCG GGAATCAGT GACTGTCACT CGAGATCTTG AGGGCACCTA CCTCTGTCGG      1380

GCCAGGAGCA CTCAAGGGGA GGTCACCCGC GAGGTGACCG TGAATGTGCT CTCCCCCCGG     1440

TATGAGGGAT CC                                                        1452

(2) INFORMATION FOR SEQ ID NO:37:

(i) SEQUENCE CHARACTERISTICS:
        (A) LENGTH: 726 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:37:

GAGCTCATGG TTGCTGGGAG CGACGCGGGG CGGGCCCTGG GGGTCCTCAG CGTGGTCTGC       60

CTGCTGCACT GCTTTGGTTT CATCAGCTGT TTTTCCCAAC AAATATATGG TGTTGTGTAT      120

GGGAATGTAA CTTTCCATGT ACCAAGCAAT GTGCCTTTAA AAGAGGTCCT ATGGAAAAAA      180

CAAAAGGATA AAGTTGCAGA ACTGGAAAAT TCTGAATTCA GAGCTTTCTC ATCTTTTAAA      240

AATAGGGTTT ATTTAGACAC TGTGTCAGGT AGCCTCACTA TCTACAACTT AACATCATCA      300

GATGAAGATG AGTATGAAAT GGAATCGCCA AATATTACTG ATACCATGAA GTTCTTTCTT      360

TATGTGCTTG AGTCTCTTCC ATCTCCCACA CTAACTTGTG CATTGACTAA TGGAAGCATT      420

GAAGTCCAAT GCATGATACC AGAGCATTAC AACAGCCATC GAGGACTTAT AATGTACTCA      480

TGGGATTGTC CTATGGAGCA ATGTAAACGT AACTCAACCA GTATATATTT TAAGATGGAA      540

AATGATCTTC CACAAAAAAT ACAGTGTACT CTTAGCAATC CATTATTTAA TACAACATCA      600

TCAATCATTT TGACAACCTG TATCCCAAGC AGCGGTCATT CAAGACACAG ATATGCACTT      660

ATACCCATAC CATTAGCAGT AATTACAACA TGTATTGTGC TGTATATGAA TGTTCTTTAA      720

GGATCC                                                                726

(2) INFORMATION FOR SEQ ID NO:38:

(i) SEQUENCE CHARACTERISTICS:
```

(A) LENGTH: 657 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:38:

```
GAGCTCATGG TTGCTGGGAG CGACGCGGGG CGGGCCCTGG GGGTCCTCAG CGTGGTCTGC      60

CTGCTGCACT GCTTTGGTTT CATCAGCTGT TTTTCCCAAC AAATATATGG TGTTGTGTAT     120

GGGAATGTAA CTTTCCATGT ACCAAGCAAT GTGCCTTTAA AAGAGGTCCT ATGGAAAAAA     180

CAAAAGGATA AAGTTGCAGA ACTGGAAAAT TCTGAATTCA GAGCTTTCTC ATCTTTTAAA     240

AATAGGGTTT ATTTAGACAC TGTGTCAGGT AGCCTCACTA TCTACAACTT AACATCATCA     300

GATGAAGATG AGTATGAAAT GGAATCGCCA AATATTACTG ATACCATGAA GTTCTTTCTT     360

TATGTGCTTG AGTCTCTTCC ATCTCCCACA CTAACTTGTG CATTGACTAA TGGAAGCATT     420

GAAGTCCAAT GCATGATACC AGAGCATTAC AACAGCCATC GAGGACTTAT AATGTACTCA     480

TGGGATTGTC CTATGGAGCA ATGTAAACGT AACTCAACCA GTATATATTT TAAGATGGAA     540

AATGATCTTC CACAAAAAAT ACAGTGTACT CTTAGCAATC CATTATTTAA TACAACATCA     600

TCAATCATTT TGACAACCTG TATCCCAAGC AGCGGTCATT CAAGACACAG AGGATCC        657
```

(2) INFORMATION FOR SEQ ID NO:39:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:39:

```
Glu Gln Leu Glu Ser Ile Ile Asn Phe Glu Lys Leu Thr Glu Trp Thr
1               5                   10                  15

Ser Ser Asn Val Met Glu Glu Arg
            20
```

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:40:

```
Asp Leu Arg Gly Tyr Val Tyr Gln Gly Leu
1               5                   10
```

(2) INFORMATION FOR SEQ ID NO:41:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:41:

```
Phe Arg Ile Gly Cys Arg His Ser Arg
1               5
```

(2) INFORMATION FOR SEQ ID NO:42:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:42:

```
Ile Leu Lys Glu Pro Val His Gly Val
1               5
```

(2) INFORMATION FOR SEQ ID NO:43:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

```
ATATGGATCC TCACCATCTC AGGGTGAGGG GC                              32
```

(2) INFORMATION FOR SEQ ID NO:44:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:44:

Arg Gly Tyr Val Tyr Gln Gly Leu Lys Ser
1               5                   10

(2) INFORMATION FOR SEQ ID NO:45:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:45:

Phe Ala Pro Gly Asn Tyr Pro Ala Leu
1               5

(2) INFORMATION FOR SEQ ID NO:46:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

TTTAGAATTC ACCATGGCTT CAACCCGTGC CAAG                                34

(2) INFORMATION FOR SEQ ID NO:47:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

TTTAGTCGAC TCAGGGAGGT GGGGCTTGTC C                                   31

(2) INFORMATION FOR SEQ ID NO:48:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:48:

TTTAGAATTC ACCATGGCTT GCAATTGTCA GTTG        34

(2) INFORMATION FOR SEQ ID NO:49:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

TTTAGTCGAC CTAAAGGAAG ACGGTCTGTT C        31

(2) INFORMATION FOR SEQ ID NO:50:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:50:

TTTAGAATTC ACCATGGACC CCAGATGCAC CATGGG        36

(2) INFORMATION FOR SEQ ID NO:51:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:51:

TTTAGTCGAC TCACTCTGCA TTTGGTTTTG CTGA        34

(2) INFORMATION FOR SEQ ID NO:52:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:52:

ACCCTTGAAT CCATGGGCCA CACACGGAGG CAG                          33

(2) INFORMATION FOR SEQ ID NO:53:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:53:

ATTACCGGAT CCTTATACAG GGCGTACACT TTCCCTTCT                    39

(2) INFORMATION FOR SEQ ID NO:54:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:54:

ACCCTTGAGC TCATGGATCC CCAGTGCACT ATG                          33

(2) INFORMATION FOR SEQ ID NO:55:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:55:

ATTACCCCCG GGTTAAAAAC ATGTATCACT TTTGTCGCAT GA                42

(2) INFORMATION FOR SEQ ID NO:56:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

```
ACCCTTGAGC TCATGGTTGC TGGGAGCGAC GCGGGG                                    36

(2) INFORMATION FOR SEQ ID NO:57:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:57:

ATTACCGGAT CCTTAAAGAA CATTCATATA CAGCACAATA CA                             42

(2) INFORMATION FOR SEQ ID NO:58:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:58:

ACCCTTGAAT TCATGGCTCC CAGCAGCCCC CGGCCC                                    36

(2) INFORMATION FOR SEQ ID NO:59:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:59:

ATTACCGGAT CCTCAGGGAG GCGTGGCTTG TGTGTTCGG                                 39
```